(12) United States Patent
Hochstrasser et al.

(10) Patent No.: US 7,955,804 B2
(45) Date of Patent: *Jun. 7, 2011

(54) DIAGNOSTIC METHOD FOR BRAIN DAMAGE-RELATED DISORDERS

(75) Inventors: Denis F. Hochstrasser, Geneva (CH); Jean-Charles Sanchez, Geneva (CH); Pierre Lescuyer, Annemasse (FR); Laure Allard, Gaillard (FR)

(73) Assignee: Electrophoretics Limited (GB)

( * ) Notice: Subject to any disclaimer, the term of this patent is extended or adjusted under 35 U.S.C. 154(b) by 164 days.

This patent is subject to a terminal disclaimer.

(21) Appl. No.: 11/154,911

(22) Filed: Jun. 16, 2005

(65) Prior Publication Data

US 2007/0042425 A1 Feb. 22, 2007

Related U.S. Application Data

(63) Continuation of application No. PCT/GB2004/050012, filed on Sep. 20, 2004.

(30) Foreign Application Priority Data

Sep. 20, 2003 (GB) .................................. 0322063.9
Jun. 23, 2004 (GB) .................................. 0414089.3
Aug. 27, 2004 (GB) .................................. 0419068.2

(51) Int. Cl.
*G01N 33/48* (2006.01)
*G01N 33/49* (2006.01)
*G01N 33/50* (2006.01)
*G01N 33/68* (2006.01)
*G01N 33/96* (2006.01)

(52) U.S. Cl. .......................... 435/7.1; 435/7.95; 436/501

(58) Field of Classification Search ........................ None
See application file for complete search history.

(56) References Cited

U.S. PATENT DOCUMENTS

2004/0253637 A1* 12/2004 Buechler et al. ............... 435/7.1
2005/0255484 A1 11/2005 Valkirs et al. .................... 435/6

OTHER PUBLICATIONS

Gok et al., Clinical Chemica Acta, 338(1-2):33-43, Dec. 2003.*
Wilson et al., FASEB, 14(5):791-796, 2000.*
Ishii, J. et al., Clin. Chem. 43:1372-1378, 1997.*
[abstract only] Tsuji, R. et al., Int. J. Cardiol. 41:209-217, 1993.*
Glatz, J. F. et al., Br. Heart J. 71:135-140, 1994.*
Hayashida et al., Jpn Circ J, 64:18-22, Jan. 2000.*
Ramaswamy et al., Pediatric Neurology, 40(3):215-226, Mar. 2009.*
Vaagenes P, Urdal P, Melvoll R, Valnes K: Enzyme level changes in the cerebrospinal fluid of patients with acute stroke. Arch Neurol 1986;43:357-362.
Matias-Guiu J, Martinez-Vazquez J, Ruibal A, Colomer R, Boada M, Codina A: Myelin basic protein and creatine kinase BB isoenzyme as CSF markers of intracranial tumors and stroke. Acta Neurol Scand 1986;73:461-465.
Persson L, Hardemark HG, Gustafsson J, Rundstrom G, Mendel-Hartvig I, Esscher T, Pahlman S: S-100 protein and neuron-specific enolase in cerebrospinal fluid and serum: markers of cell damage in human central nervous system. Stroke 1987;18:911-918.
Hochstrasser DF Merril CR: 'Catalysts' for polyacrylamide gel polymerization and detection of proteins by silver staining. Appl Theor Electrophor 1988;1:35-40.
Lampl Y, Paniri Y, Eshel Y, Sarova-Pinhas I: Cerebrospinal fluid lactate dehydrogenase levels in early stroke and transient ischemic attacks. Stroke 1990;21:854-857.
Cunningham RT, Young IS, Winder J, O'Kane MJ, McKinstry S, Johnston CF, Dolan OM, Hawkins SA, Buchanan KD: Serum neurone specific enolase (NSE) levels as an indicator of neuronal damage in patients with cerebral infarction. Eur J Clin Invest 1991;21:497-500.
Hochstrasser DF, Frutiger S, Paquet N, Bairoch A, Ravier F, Pasquali C, Sanchez JC, Tissot JD, Bjellqvist B, Vargas R, et al.: Human liver protein map: a reference database established by microsequencing and gel comparison. Electrophoresis 1992;13:992-1001.
Watson MAScott MG: Clinical utility of biochemical analysis of cerebrospinal fluid. Clin Chem 1995;41:343-360.
Appel RD, Palagi PM, Walther D, Vargas JR, Sanchez JC, Ravier F, Pasquali C, Hochstrasser DF: Melanie II—a third-generation software package for analysis of two-dimensional electrophoresis images: I. Features and user interface. Electrophoresis 1997;18:2724-2734.
Herrmann M, Vos P, Wunderlich MT, de Bruijn CH, Lamers KJ: Release of glial tissue-specific proteins after acute stroke: A comparative analysis of serum concentrations of protein S-100B and glial fibrillary acidic protein. Stroke 2000;31:2670-2677.
Sanchez J-C, Chiappe D, Converset V, Hoogland C, Binz P-A, Paesano S, Appel RD, Wang S, Sennitt M, Nolan A, Cawthorne MA, Hochstrasser DF: The mouse SWISS-2D PAGE database: a tool for proteomics study of diabetes and obesity. Proteomics 2001;1:136-163.
Bitsch A, Horn C, Kemmling Y, Seipelt M, Hellenbrand U, Stiefel M, Ciesielczyk B, Cepek L, Bahn E, Ratzka P, Prange H, Otto M: Serum tau protein level as a marker of axonal damage in acute ischemic stroke. Eur Neurol 2002;47:45-51.
N. Turck et al., "GSTP-1 and UFD-1 as Early Blood Markers of Acute Stroke," Eurostroke (2006).
A. Hainard et al., "A Combined CXCL10, CXCL8 and H-FABP Panel for the Staging of Human African Trypanosomiasis Patients," PLOS 3(6):e459 (2009).
Turck et al., "A multiparameter panel method for outcome prediction following aneurismal subarachnoid hemorrhage" Intensive Care Med (Sep. 17, 2009).
Zimmerman et al., "Fatty acid binding protein as a serum marker for the early diagnosis of stroke: a pilot study" MCP Papers in Press (Manuscript M300066-MCP200) (Oct. 26, 2003).
Allard et al., "PARK7 and Nucleoside Diphosphate Kinase A as Plasma Markers for the early Diagnosis of Stroke" Clinical Chemistry 51:11 (2005).
Turck et al, "Blood GST-π Predicts Stroke Severity and Outcome", unpublished manuscript prepared Dec. 2009, in Geneva, Switzerland.

* cited by examiner

*Primary Examiner* — Lorraine Spector
*Assistant Examiner* — Stacey MacFarlane
(74) *Attorney, Agent, or Firm* — Arent Fox LLP

(57) ABSTRACT

A brain damage-related disorder is diagnosed in a subject by detecting at least one polypeptide, or a variant or mutant thereof, selected from A-FABP, E-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A) in a sample of body fluid taken from the subject.

4 Claims, 40 Drawing Sheets

Figure 6: ELISA intensity signal obtained for UFD1, RNA-BP and NDK A
stroke patients matched age/sex with control patients

STROKE PATIENTS (between 0-24h arrival at emergency hospital)

| Patient number | Diagnostic | Sex | year of birth | time onset of symptoms | UFD1 (RFU signal) CO=9047 | RNA-BP (RFU signal) CO=7441 | NDK A (RFU signal) CO=12500 |
|---|---|---|---|---|---|---|---|
| 186 | Ic | M | 1931 | 30 min | 7127 | 10844 | 13,639 |
| 253 | Irr | F | 1975 | 45min | 39636 | 14367 | 19,907 |
| 245 | Ic | M | 1925 | 1h15 | 10900 | 11444 | 38,160 |
| 243 | H | M | 1938 | 1h18 | 21008 | 22046 | 25,508 |
| 239 | TIA | M | 1923 | 1h40 | 17122 | 7471 | 37,548 |
| 202 | H | M | 1949 | 1h15 | 12225 | 8379 | 66,554 |
| 229 | H | M | 1932 | 2h05 | 9237 | 14931 | |
| 271 | Irr | M | 1913 | 2h07 | 11658 | 27199 | 22,313 |
| 256 | TIA | F | 1935 | 3h00 | 17727 | 23110 | 20,671 |
| 267 | Ic | M | 1928 | 3h00 | 25665 | 11309 | 69,539 |
| 208 | Irr | F | 1945 | 8h00 | 12617 | 20467 | 13,080 |
| 212 | Irr | M | 1934 | 10h30 | 27326 | 11986 | 17,216 |
| 258 | Ic | M | 1920 | 1 d | 16814 | 9392 | 26,118 |
| 234 | TIA | M | 1914 | 2 d | 22273 | 13278 | 78,373 |
| 246 | Ic | M | 1920 | 2 d | 10374 | 10083 | 27,109 |
| 250 | Ic | M | 1908 | 4 d | 32857 | 5702 | 122,914 |
| 240 | Irr | M | 1926 | 5 d | 9796 | 17691 | 12,817 |
| 254 | Irr | F | 1960 | ? | 21142 | 10078 | 29,784 |
| 249 | | | | | | | 32,639 |

STROKE PATIENTS (after 72h arrival at emergency hospital)

| Patient number | Diagnostic | Sex | year of birth | time onset of symptoms | UFD1 (RFU signal) CO=9047 | RNA-BP (RFU signal) CO=7441 | NDK A (RFU signal) CO=12500 |
|---|---|---|---|---|---|---|---|
| 239 | TIA | M | 1923 | 1h40 | 11517 | 7169 | 19918 |
| 202 | H | M | 1949 | 1h15 | 5764 | 7706 | 27685 |
| 299 | Ic | | | | 16357 | 11919 | 21931 |

NEGATIVE CONTROL PATIENTS

| Patient number | sex | year of birth | UFD1 (RFU signal) | RNA-BP (RFU signal) | NDK A (RFU signal) CO=12500 |
|---|---|---|---|---|---|
| 368 | M | 1931 | 10365 | 12267 | 75,072 |
| 401 | F | 1972 | 1306 | 1209 | 2,398 |
| 404 | M | 1925 | 3564 | 4525 | 7,425 |
| 388 | M | 1938 | 2643 | 3867 | 11,877 |
| 464 | M | 1923 | 2957 | 5775 | 6,292 |
| 305 | M | 1949 | 37188 | 4587 | 5,449 |
| 317 | M | 1931 | 8857 | 13370 | 7,183 |
| 439 | M | 1913 | 4248 | 4348 | 11,884 |
| 378 | F | 1935 | 3512 | 4420 | 7,546 |
| 339 | M | 1929 | 2455 | 3784 | 5,086 |
| 349 | F | 1946 | 4076 | 4103 | 5,166 |
| 379 | M | 1934 | 8791 | 8751 | 10,497 |
| 400 | M | 1922 | 4919 | 7411 | 5,920 |
| 322 | M | 1915 | 5373 | 5757 | 12,112 |
| 443 | M | 1919 | 11589 | 13479 | 13,797 |
| 450 | M | 1909 | 17357 | 12344 | 47,866 |
| 430 | M | 1926 | 2660 | 4505 | 7,542 |
| 354 | F | 1955 | 3711 | 3647 | 6,360 |

Ic: established stroke
Irr: Ischemic rapidly resolved
TIA: transient Ischemic attack
H: Hemorrhagic
M: Male
F: Female
RFU: Relative Fluorescence Unit (excitation wavelength 444nm, emission wavelength 555nm)

positive plasma (/ cutoff)

patient tested between 0-24h AND after 72h 25,508 patient (Hemorrhagic) n°273 age/sex matched with the control instead of n° 243

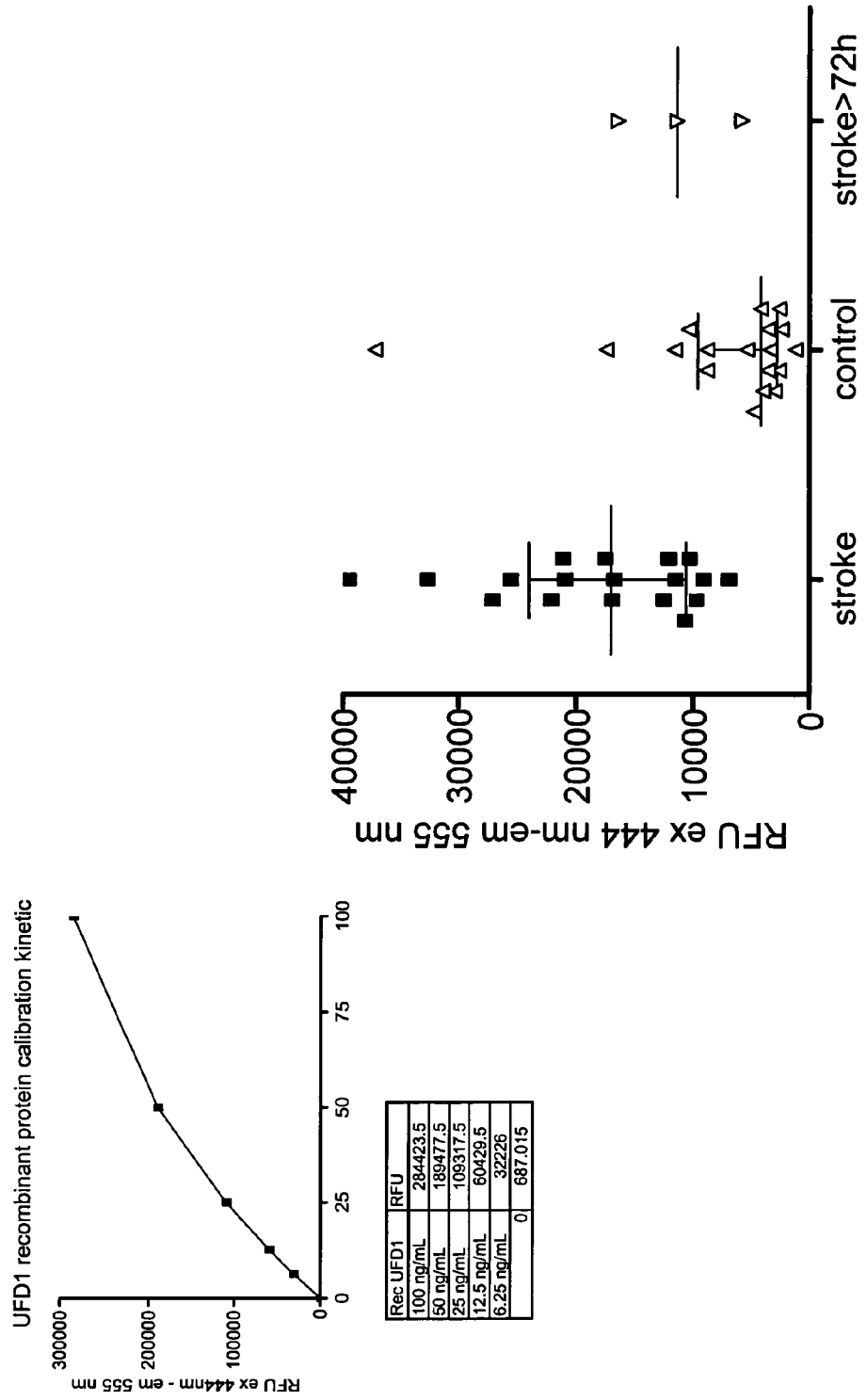
Figure 7. UFD1 detection in new plasma samples 2 fold diluted. Antibodies sandwich immunofluorescent ELISA. Crude values kinetic mode. Controls/stroke matched age/sex

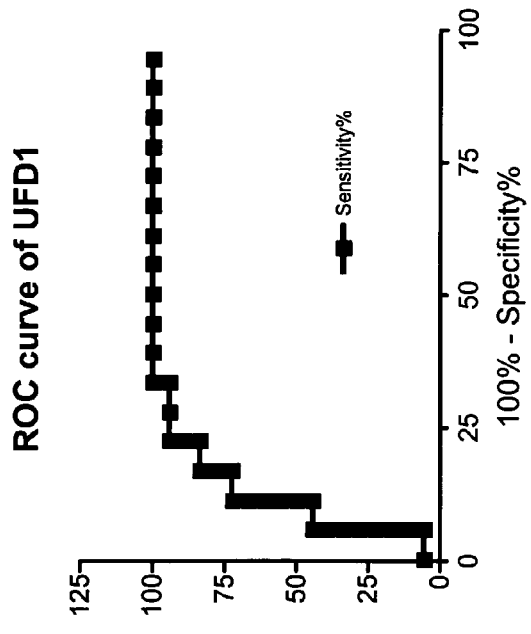
Figure 8. ROC curve of UFD1
UFD1 best cutoff value to differentiate stroke vs control. Determination of sensitivity and specificity
|  | cutoff | P (Mann et Whitney) | SE | SP |
|---|---|---|---|---|
| S vs. C | 9047 | <0.0001 | 94.4% | 77.8% |

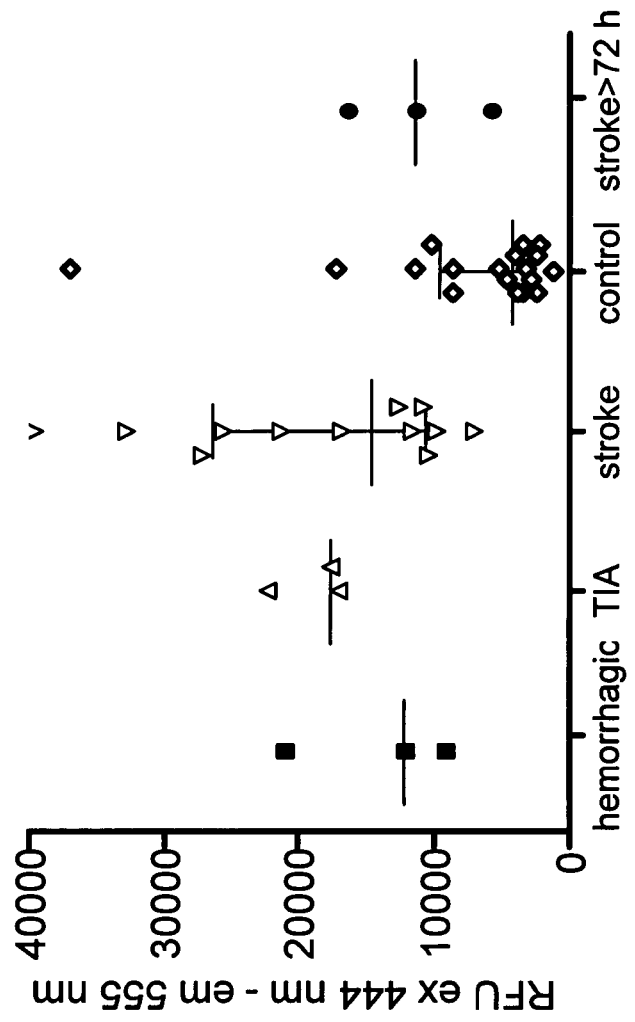
Figure 9. UFD1 detection in new plasma samples 2 fold diluted. Antibodies sandwich immunofluorescent ELISA. Crude values kinetic mode. Controls/stroke matched age/sex

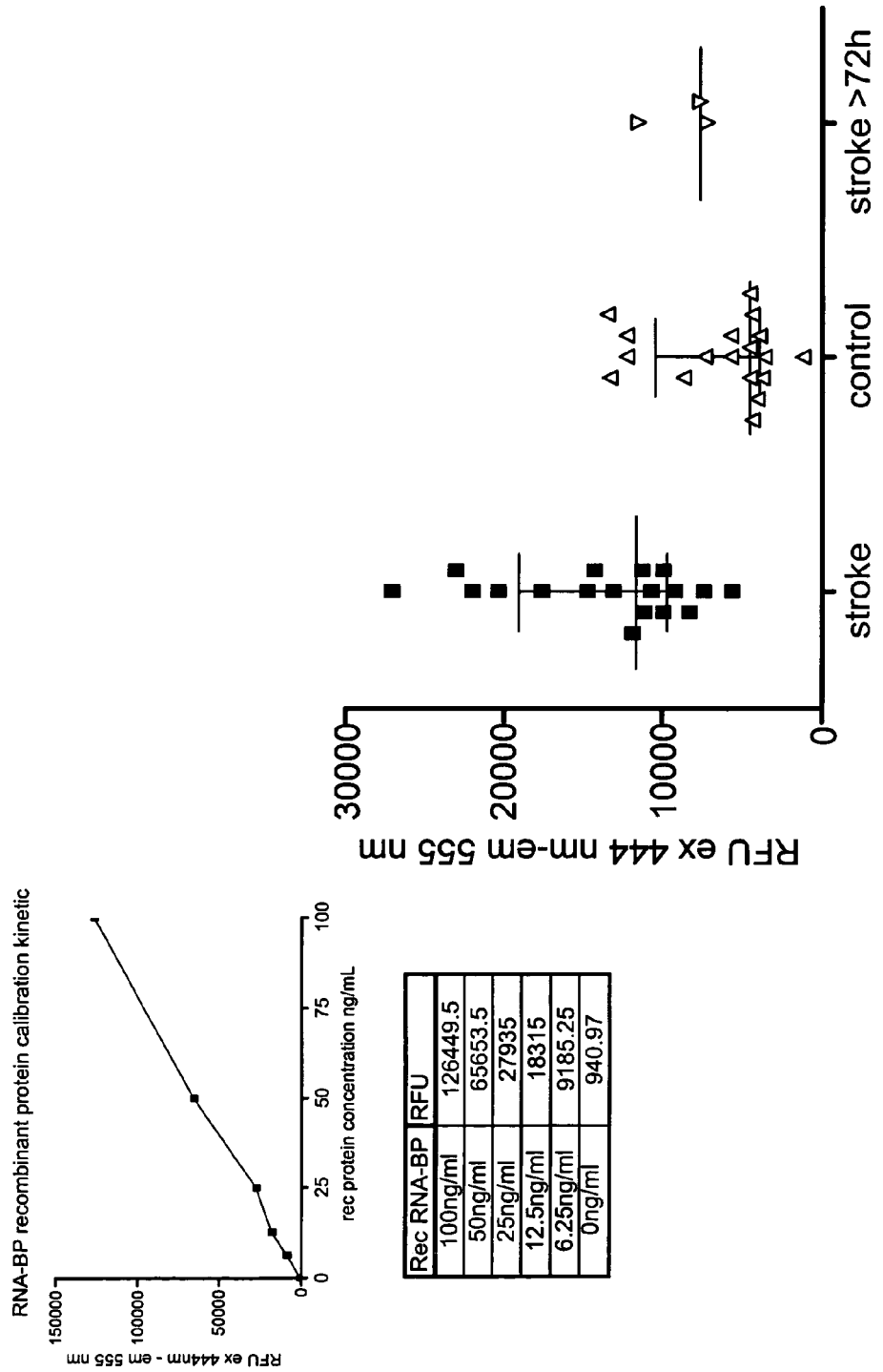
Figure 10. RNA-BP detection in new plasma samples 2 fold diluted. Antibodies sandwich immunofluorescent ELISA. Crude values kinetic mode. Controls/stroke matched age/sex Figure 11. ROC curve of RNA-BP
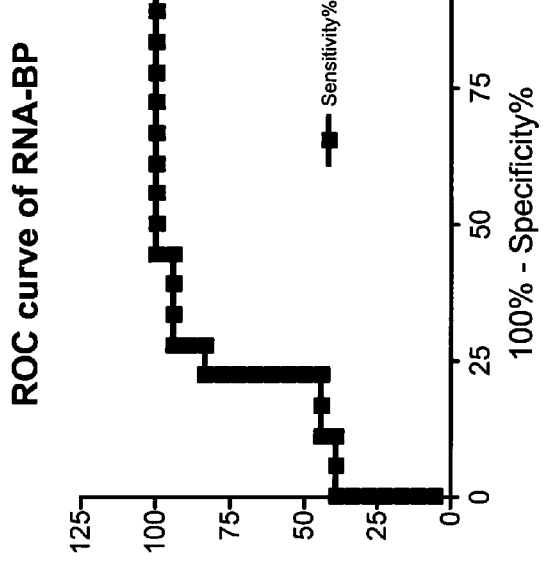
RNA-BP best cutoff value to differentiate stroke vs control. Determination of sensitivity and specificity
|  | cutoff | P (Mann et Whitney) | SE | SP |
|---|---|---|---|---|
| S vs. C | 7441 | 0.0003 | 94.4% | 72.2% |

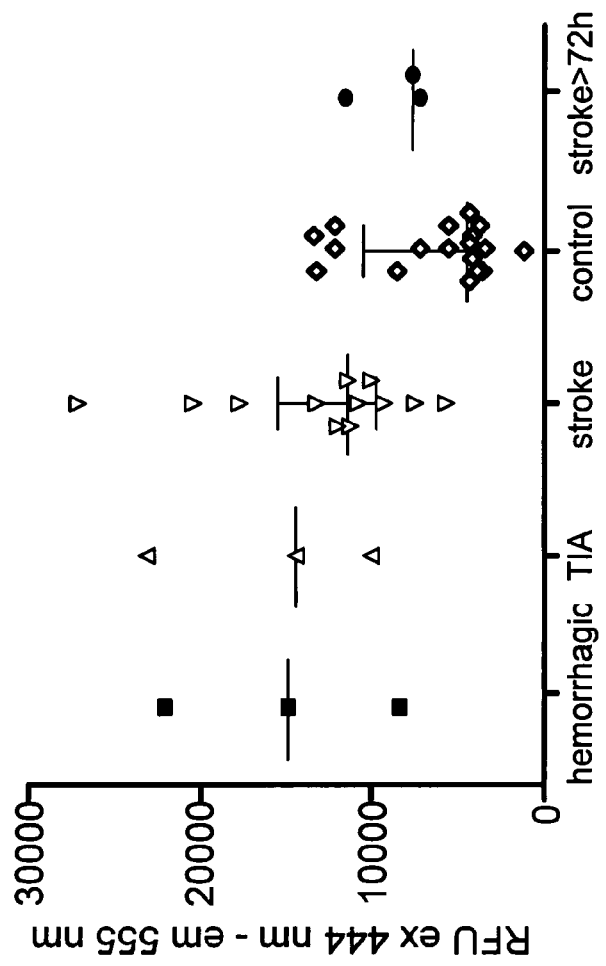
Figure 12. RNA-BP detection in new plasma samples 2 fold diluted. Antibodies sandwich immunofluorescent ELISA. Crude values kinetic mode. Controls/stroke matched age/sex

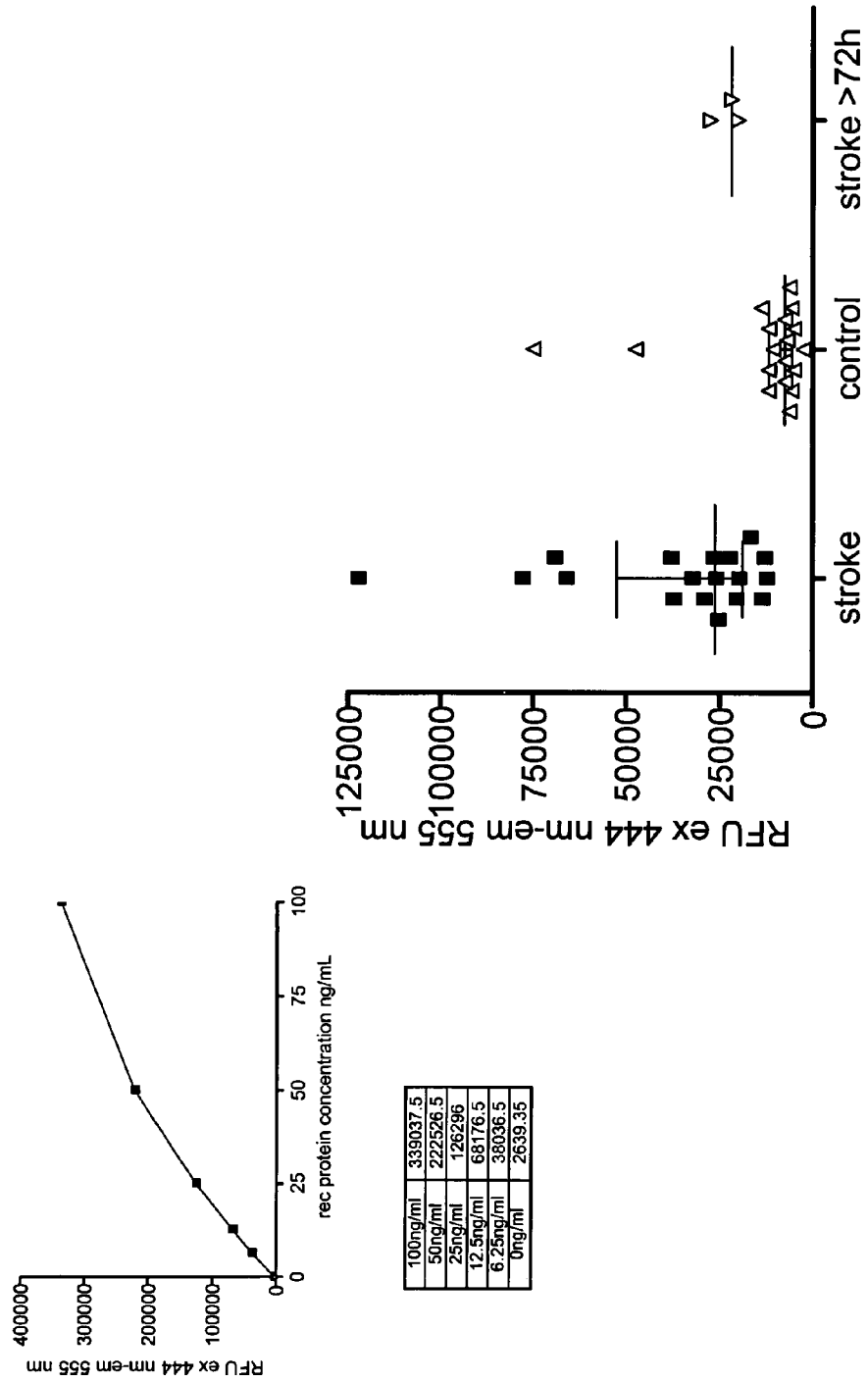
Figure 13. NDK A detection in new plasma samples non diluted. Antibodies sandwich immunofluorescent ELISA. Crude values kinetic mode. Controls/stroke matched age/sex Figure 14. ROC curve of NDK A
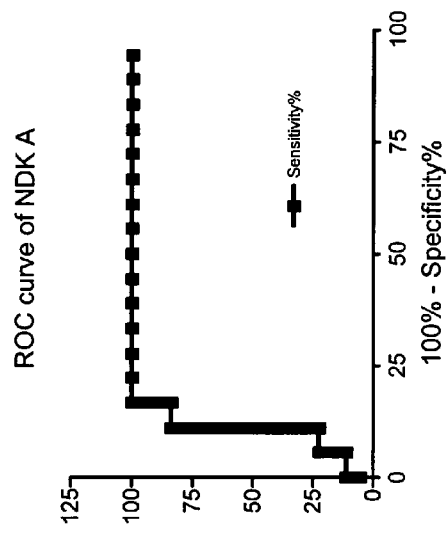
NDK A best cutoff value to differentiate stroke vs control. Determination of sensitivity and specificity
| | cutoff | P (Mann et Whitney) | SE | SP |
|---|---|---|---|---|
| S vs. C | 12464 | <0.0001 | 100% | 83.3% |

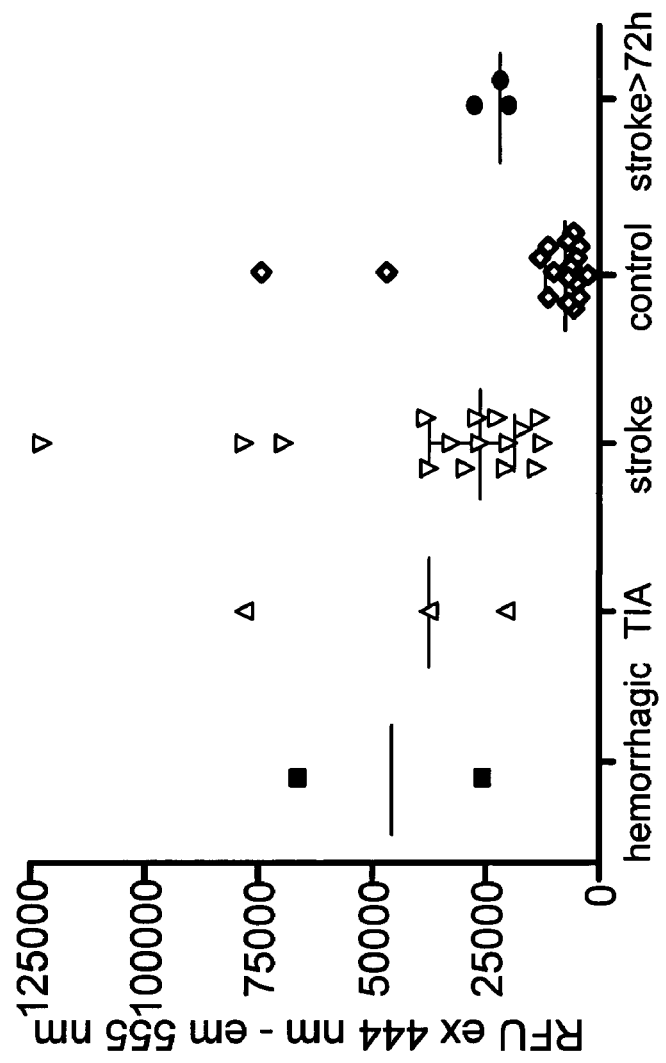
Figure 15. NDK A detection in new plasma samples non diluted. Antibodies sandwich immunofluorescent ELISA. Crude values kinetic mode. Controls/stroke matched age/sex

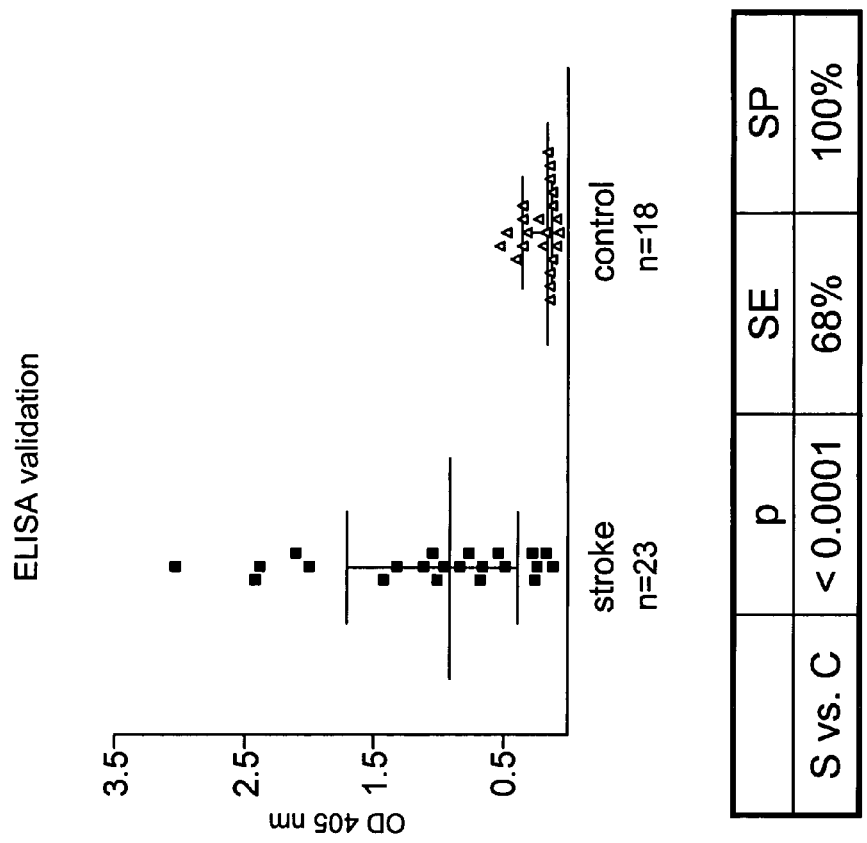
Figure 18 - Heart-Fatty Acid Binding Protein (H-FABP)

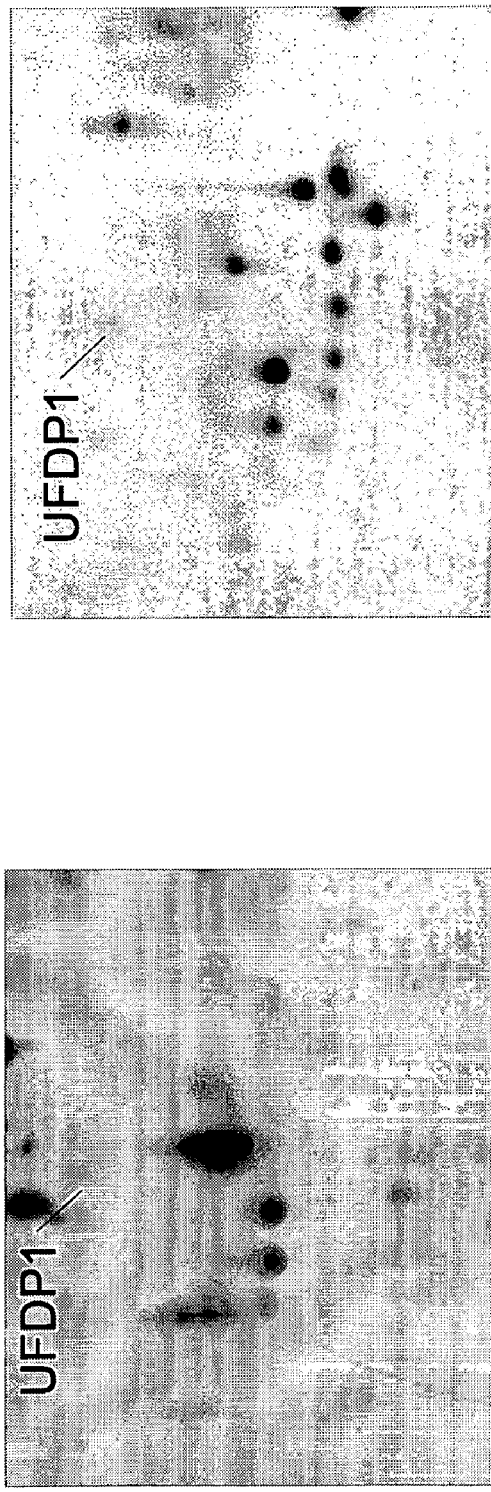
Figure 19 - UFDP-1 discovery in post-mortem CSF

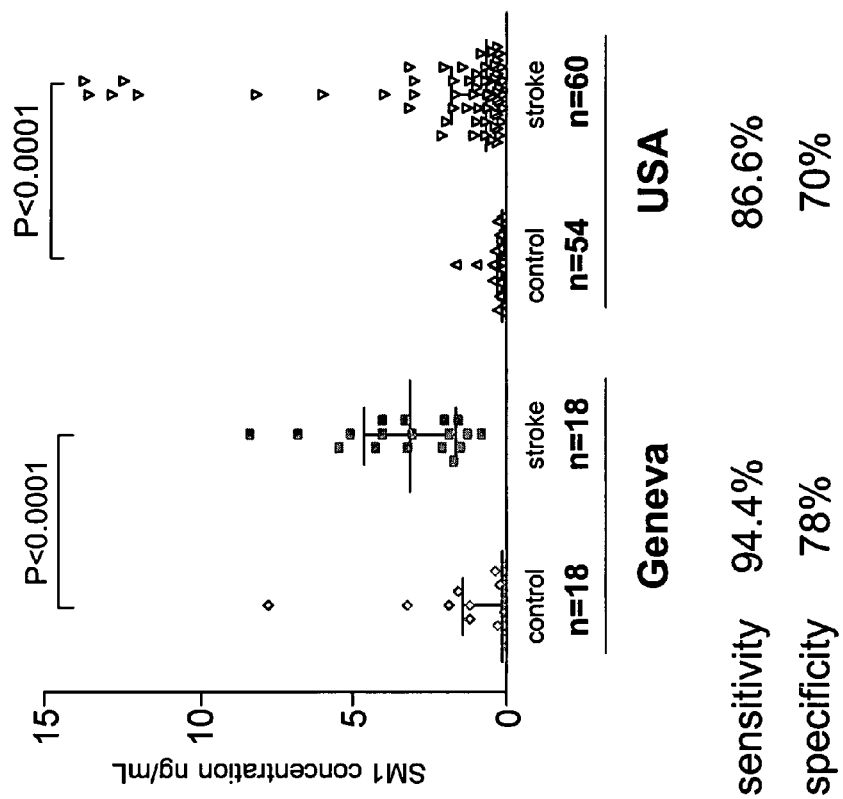
Figure 20 - UFDP1 plasma concentration: ELISA

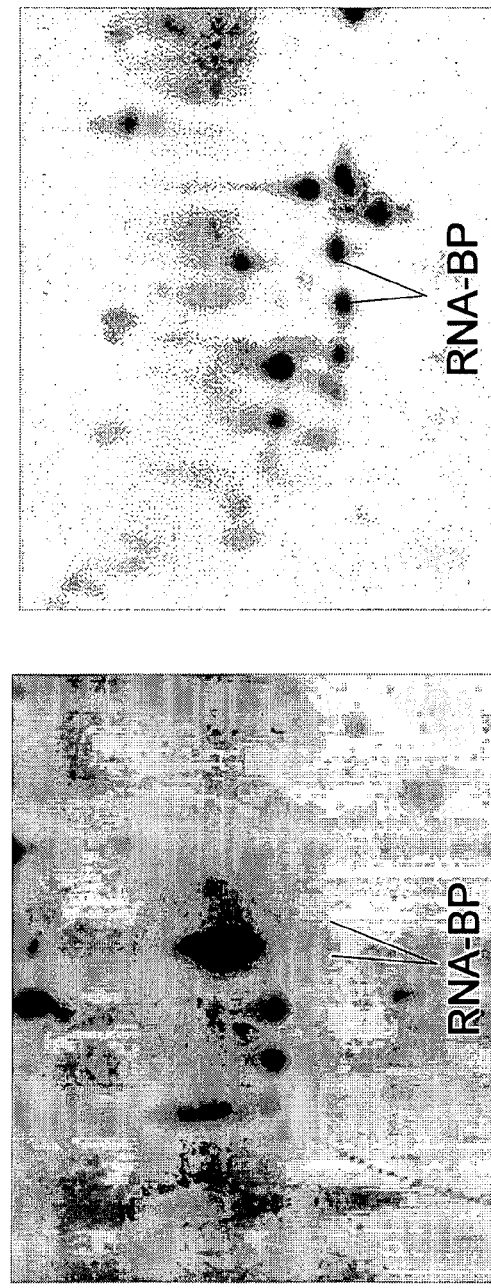
Figure 21 - RNA-BP discovery in post-mortem CSF

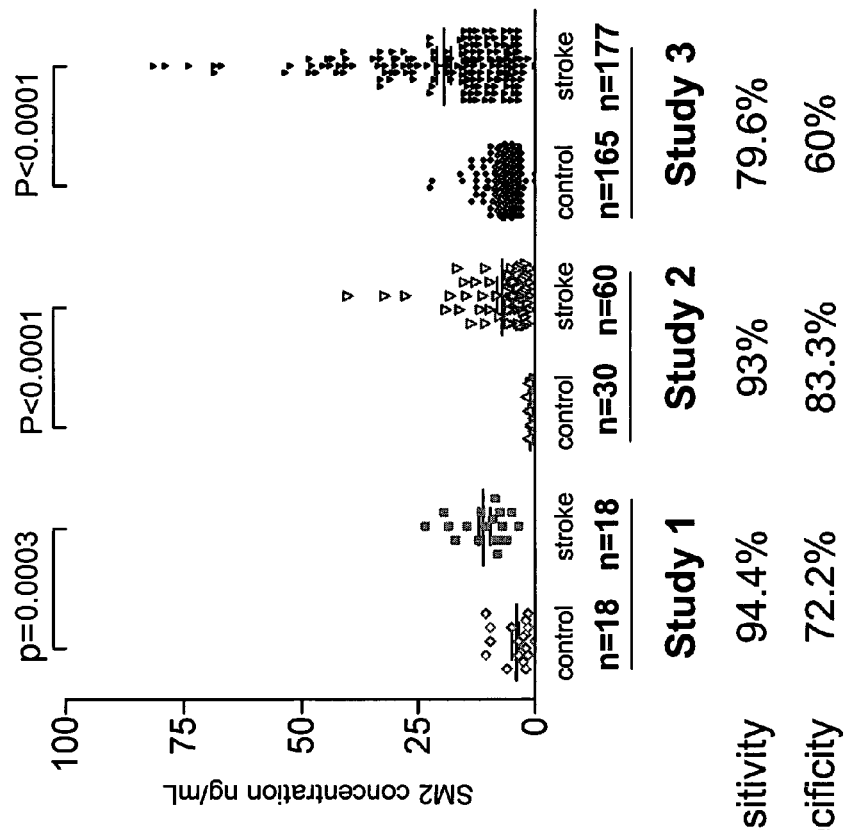
Figure 22 - RNA-BP plasma concentration: ELISA

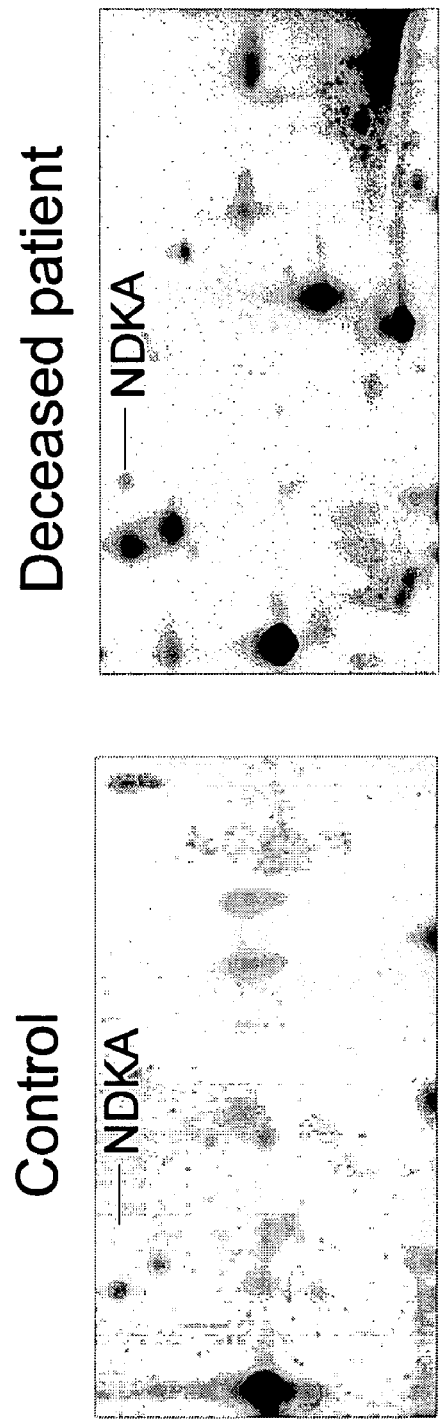
Figure 23 - NDKA discovery in post-mortem CSF

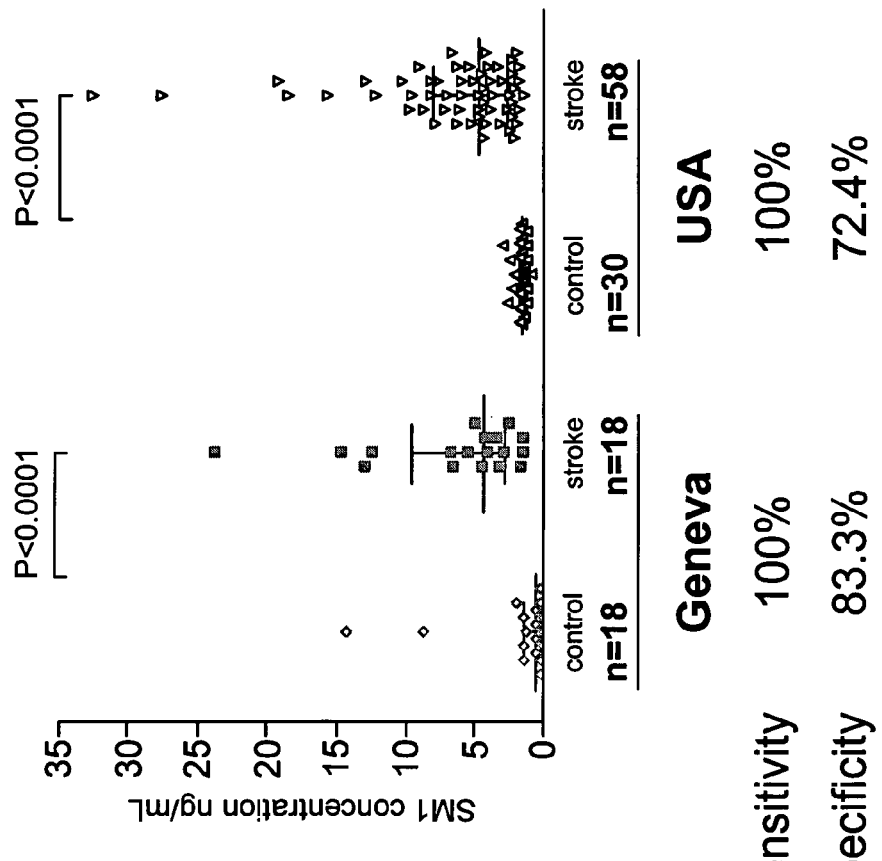
Figure 24 - NDKA plasma concentration: ELISA

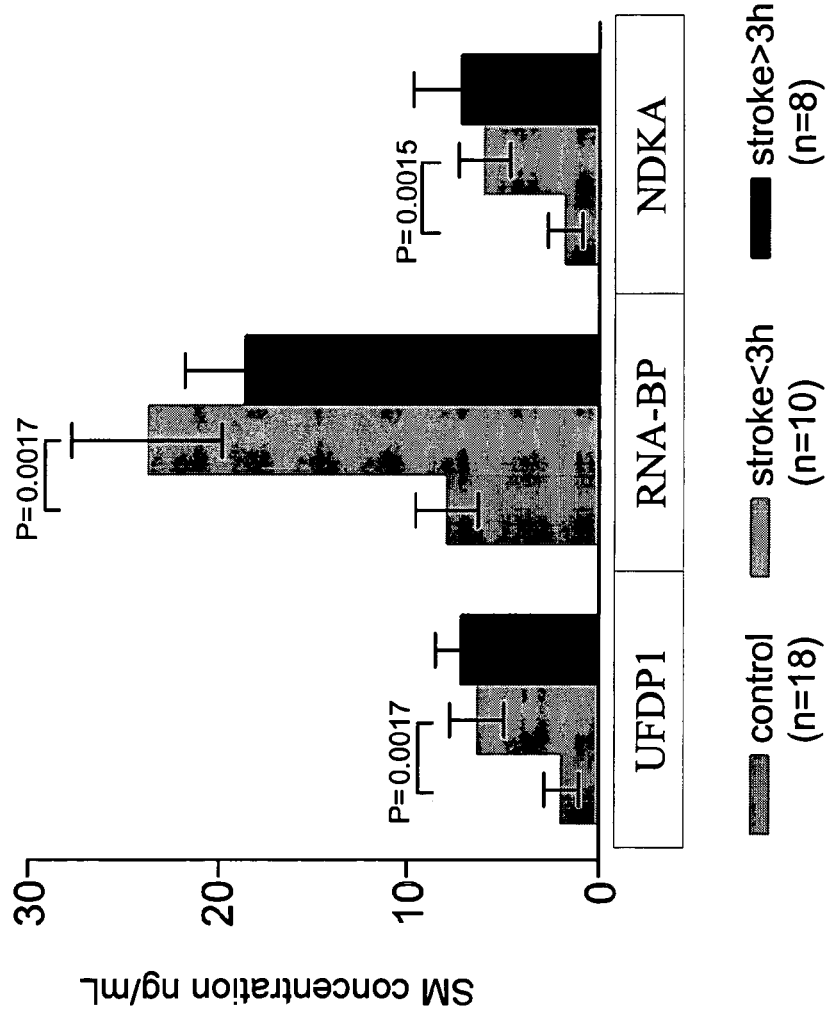
Figure 25a - Time onset of symptoms

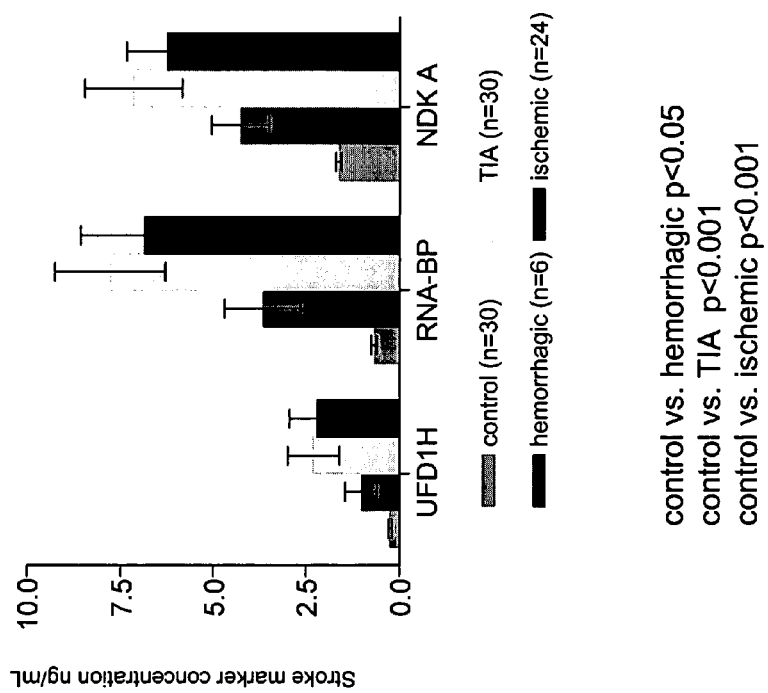
Figure 25b - Type of stroke

Figure 26 - PANEL of early plasmatic markers of stroke

| Protein | Marker type | Sensitivity % | Specificity % |
|---|---|---|---|
| H-FABP | Early diagnosis marker of stroke | 68 | 100 |
| UFDP1 | Early diagnosis marker of stroke | 94 | 78 |
| RNA-BP | Early diagnosis marker of stroke | 94 | 72 |
| NDKA | Early diagnosis marker of stroke | 100 | 83 |

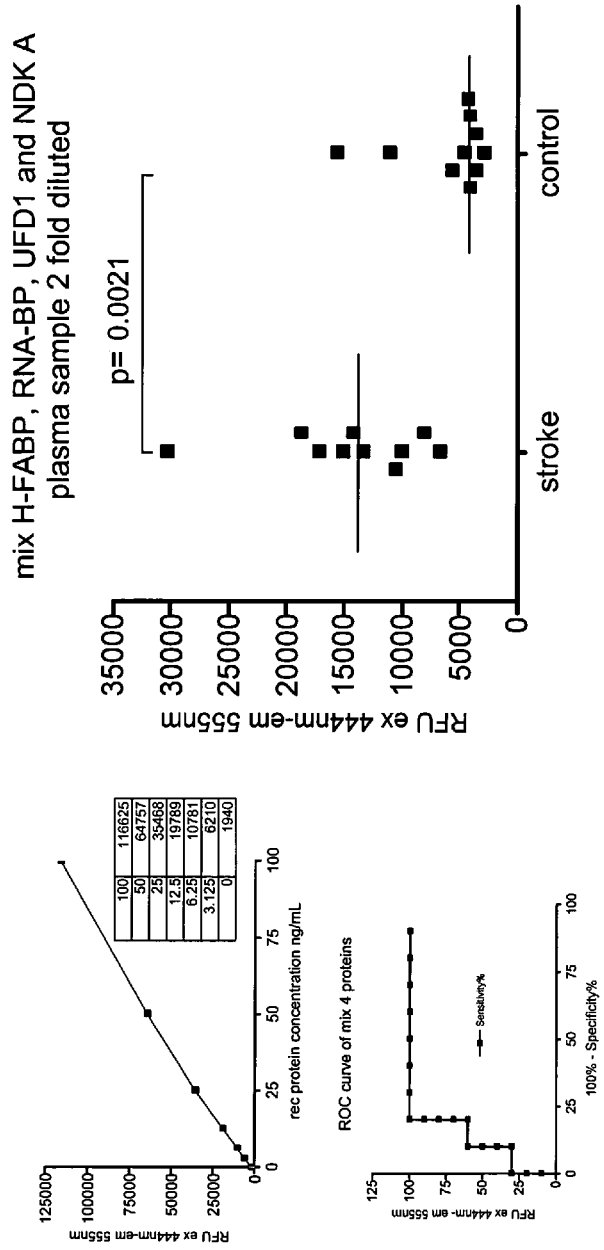
Figure 27. Mix of UFD1, RNA-BP, NDK A and H-FABP in the same well. Detection of the total signal generated by all the proteins in new plasma samples 2 fold diluted. Antibodies sandwich immunofluorescent ELISA. Crude values kinetic fluorescent mode. Controls/stroke matched age/sex

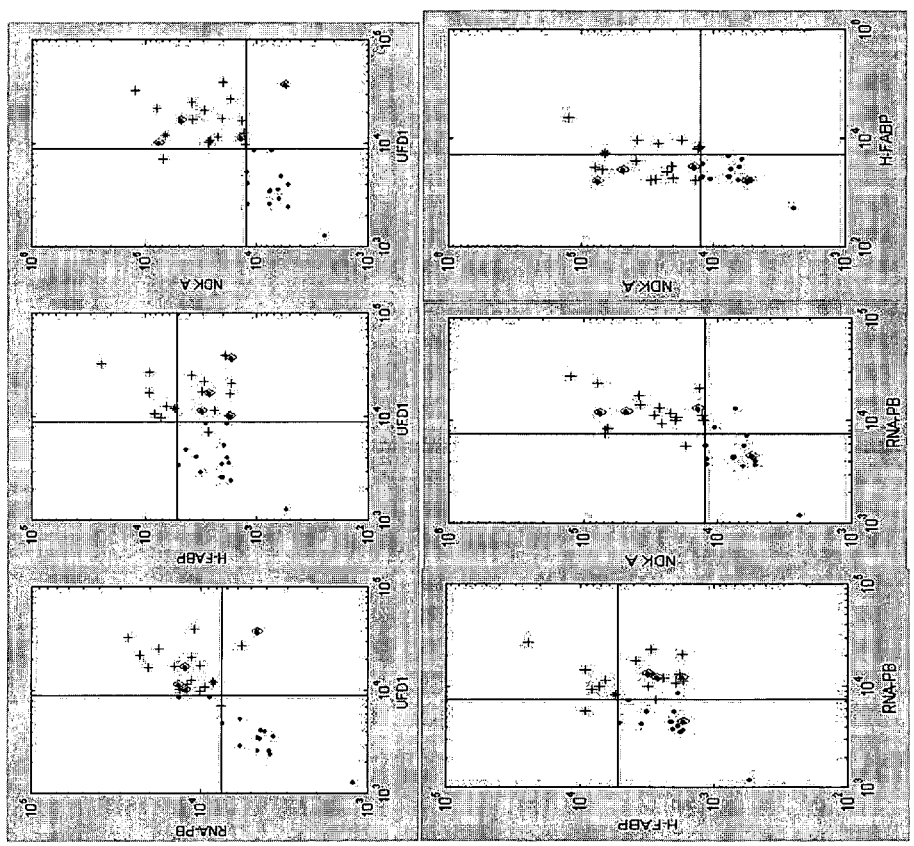
Figure 28. Graphic representation of combination of 2 out the 4 biomarkers of interest. Indicated cut-off (horizontal and vertical lines) are the ones given by us. Dot: negative controls, cross, stroke patients, dots in diamonds: false positive control samples.

FIGURE 29A

| Patient number | Diag | Sex | year of birth (year) | time onset of symptoms (min) | UFD1 (ng/mL) | RNA-BP (ng/mL) | NDK A (ng/mL) |
|---|---|---|---|---|---|---|---|
| 186 | I | M | 1931 | 30 | 1.67 | 9.58 | 1.73 |
| 253 | I | F | 1975 | 45 | 16.76 | 15.84 | 3.01 |
| 245 | I | M | 1925 | 75 | 3.42 | 13.14 | 6.73 |
| 243 | H | M | 1938 | 78 | 8.11 | 36.64 | 4.15 |
| 239 | TIA | M | 1923 | 100 | 6.31 | 22.38 | 6.60 |
| 202 | H | M | 1949 | 75 | 4.04 | 11.26 | 12.52 |
| 229 | H | M | 1932 | 125 | 2.65 | 23.43 | NAN |
| 271 | I | M | 1913 | 127 | 3.77 | 17.96 | 3.50 |
| 256 | TIA | F | 1935 | 180 | 6.59 | 14.43 | 3.16 |
| 267 | I | M | 1928 | 180 | 10.27 | 28.55 | 13.13 |
| 208 | I | F | 1945 | 480 | 4.22 | 16.95 | 1.61 |
| 212 | I | M | 1934 | 630 | 11.04 | 6.29 | 2.46 |
| 258 | I | M | 1920 | 1440 | 6.17 | 33.71 | 4.27 |
| 234 | TIA | M | 1914 | 2880 | 8.70 | 38.62 | 14.93 |
| 246 | I | M | 1920 | 2880 | 3.18 | 20.36 | 4.47 |
| 250 | I | M | 1908 | 5760 | 13.61 | 46.21 | 24.02 |
| 240 | I | M | 1926 | 7200 | 2.91 | 14.42 | 1.56 |
| 254 | I | F | 1960 | NAN | 8.18 | 16.70 | 5.02 |
| 249 | I | M | 1931 | 720 | NAN | NAN | 5.60 |
| 255 | I | M | 1910 | 2880 | 7.31 | 47.38 | 4.41 |
| 298 | I | M | 1910 | 225 | 7.58 | 55.55 | 32.84 |
| 154 | I | F | 1910 | 165 | 6.72 | 13.22 | 7.73 |
| 179 | I | F | 1912 | 150 | 6.74 | 13.62 | 4.08 |
| 248 | TIA | F | 1912 | 150 | 10.72 | 19.00 | 4.59 |
| 225 | I | M | 1915 | 1440 | 4.35 | 13.74 | 12.98 |
| 156 | I | F | 1919 | 650 | 1.87 | 4.87 | 0.84 |
| 173 | I | M | 1920 | 2880 | 7.00 | 13.00 | 5.92 |
| 205 | I | M | 1920 | 2880 | 10.94 | 14.83 | 6.12 |
| 299 | I | F | 1923 | 2880 | 7.19 | 26.47 | 31.49 |
| 245 | I | M | 1925 | 75 | 2.83 | 9.61 | 7.00 |
| 189 | TIA | M | 1926 | 360 | 2.07 | 8.68 | 2.54 |
| 181 | TIA | M | 1930 | 70 | 1.60 | 3.98 | 0.95 |
| 176 | I | M | 1932 | 2880 | 5.34 | 10.88 | 2.24 |
| 135 | I | F | 1933 | 275 | 14.85 | 18.60 | 6.38 |
| 161 | I | M | 1936 | 135 | 1.83 | 11.60 | NAN |
| 285 | I | M | 1938 | 240 | 2.48 | 9.92 | NAN |
| 215 | TIA | M | 1933 | 715 | 1.54 | 6.05 | NAN |
| 235 | I | M | 1970 | 195 | 5.12 | 16.09 | NAN |
| 368 | ctrl | M | 1931 | NAN | 3.17 | 18.48 | 14.26 |
| 401 | ctrl | F | 1972 | NAN | 0.00 | 0.00 | 0.00 |
| 404 | ctrl | M | 1925 | NAN | 0.02 | 4.10 | 0.46 |
| 388 | ctrl | M | 1938 | NAN | 0.00 | 2.88 | 1.37 |
| 464 | ctrl | M | 1923 | NAN | 0.00 | 6.42 | 0.23 |
| 305 | ctrl | M | 1949 | NAN | 15.62 | 4.22 | 0.06 |
| 317 | ctrl | M | 1931 | NAN | 2.47 | 20.53 | 0.41 |

FIGURE 29B

| Patient number | Diag | Sex | year of birth (year) | time onset of symptoms (min) | UFD1 (ng/mL) | RNA-BP (ng/mL) | NDK A (ng/mL) |
|---|---|---|---|---|---|---|---|
| 439 | ctrl | M | 1913 | NAN | 0.34 | 3.78 | 1.37 |
| 378 | ctrl | F | 1935 | NAN | 0.00 | 3.91 | 0.48 |
| 339 | ctrl | M | 1929 | NAN | 0.00 | 2.73 | -0.02 |
| 349 | ctrl | F | 1946 | NAN | 0.26 | 3.32 | 0.00 |
| 379 | ctrl | M | 1934 | NAN | 2.44 | 11.95 | 1.09 |
| 400 | ctrl | M | 1922 | NAN | 0.65 | 9.46 | 0.15 |
| 322 | ctrl | M | 1915 | NAN | 0.86 | 6.39 | 1.42 |
| 443 | ctrl | M | 1919 | NAN | 3.74 | 20.73 | 1.76 |
| 450 | ctrl | M | 1909 | NAN | 6.42 | 18.62 | 8.71 |
| 430 | ctrl | M | 1926 | NAN | 0.00 | 4.07 | 0.48 |
| 354 | ctrl | F | 1955 | NAN | 0.09 | 2.47 | 0.24 |
| 389 | ctrl | M | 1909 | NAN | 2.78 | 9.08 | 3.02 |
| 371 | ctrl | M | 1910 | NAN | 1.30 | 4.70 | 0.00 |
| 352 | ctrl | F | 1911 | NAN | 1.46 | 5.54 | 0.01 |
| 376 | ctrl | F | 1912 | NAN | 0.00 | 2.58 | 0.00 |
| 429 | ctrl | F | 1912 | NAN | 2.45 | 5.68 | 0.00 |
| 399 | ctrl | M | 1916 | NAN | 0.46 | 6.28 | 0.61 |
| 434 | ctrl | F | 1919 | NAN | 2.22 | 5.94 | 0.25 |
| 459 | ctrl | M | 1921 | NAN | 0.88 | 3.75 | 0.43 |
| 462 | ctrl | M | 1921 | NAN | 0.41 | 2.16 | 0.00 |
| 444 | ctrl | F | 1922 | NAN | 4.13 | 5.52 | 0.14 |
| 468 | ctrl | M | 1923 | NAN | 1.80 | 5.14 | 2.22 |
| 386 | ctrl | M | 1927 | NAN | 0.98 | 2.96 | 0.39 |
| 397 | ctrl | M | 1931 | NAN | 2.30 | 16.58 | 0.12 |
| 402 | ctrl | M | 1933 | NAN | 3.86 | 7.32 | 0.15 |
| 416 | ctrl | F | 1934 | NAN | 0.00 | 2.13 | 0.45 |
| 307 | ctrl | M | 1936 | NAN | 0.19 | 3.08 | NAN |
| 321 | ctrl | M | 1938 | NAN | 0.23 | 2.07 | NAN |
| 417 | ctrl | M | 1943 | NAN | 1.83 | 10.41 | NAN |
| 377 | ctrl | M | 1966 | NAN | 1.05 | 8.59 | NAN |

NAN : not tested

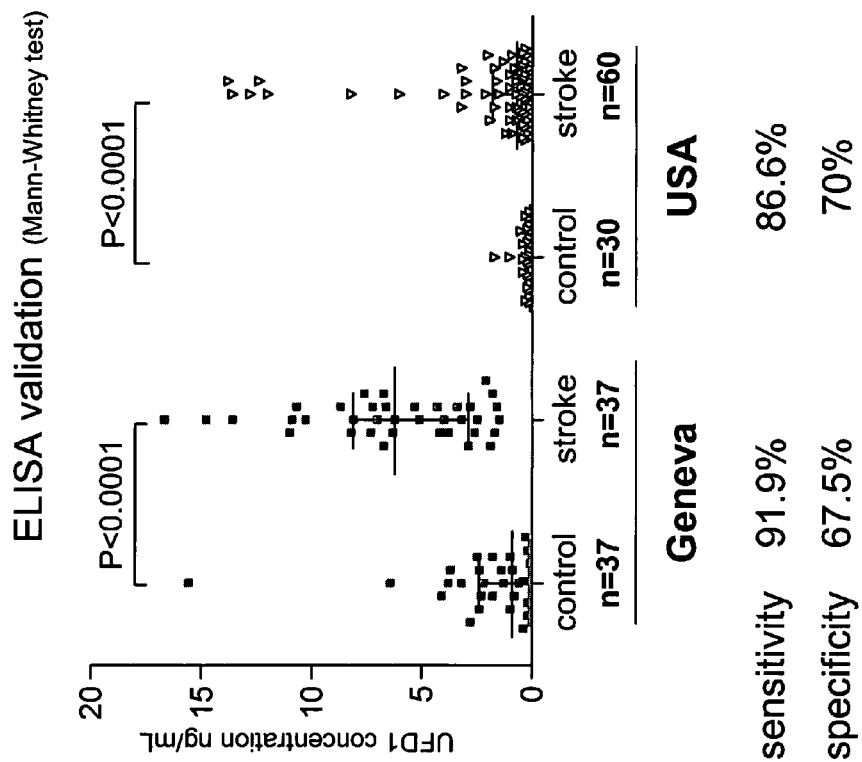
Figure 30: Ubiquitin Fusion Degradation Protein

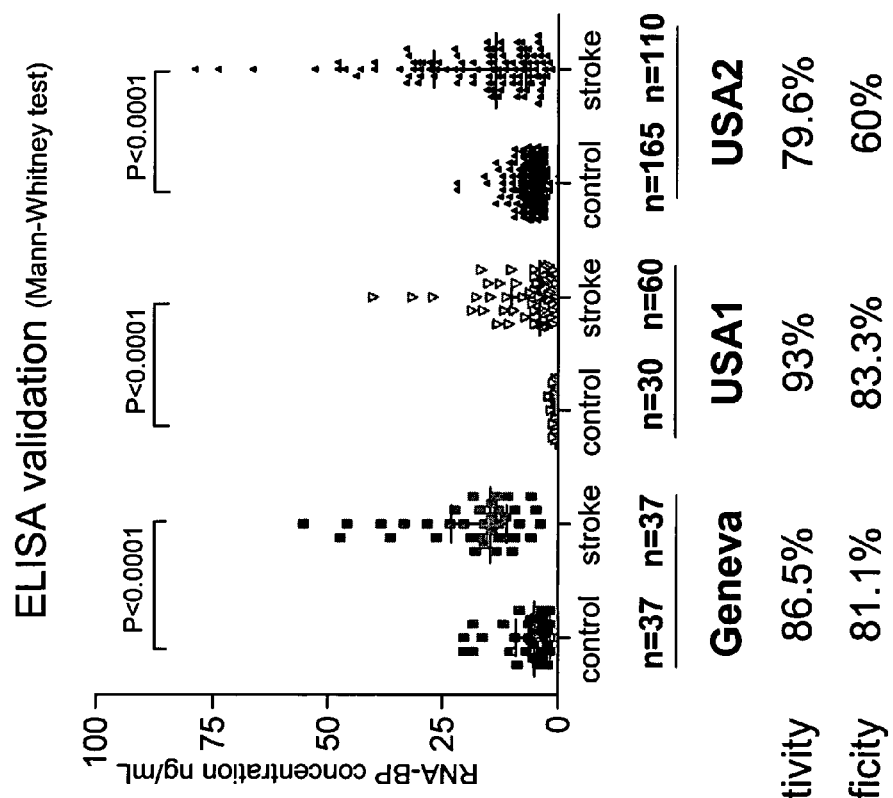
Figure 31: RNA-Binding Protein in plasma

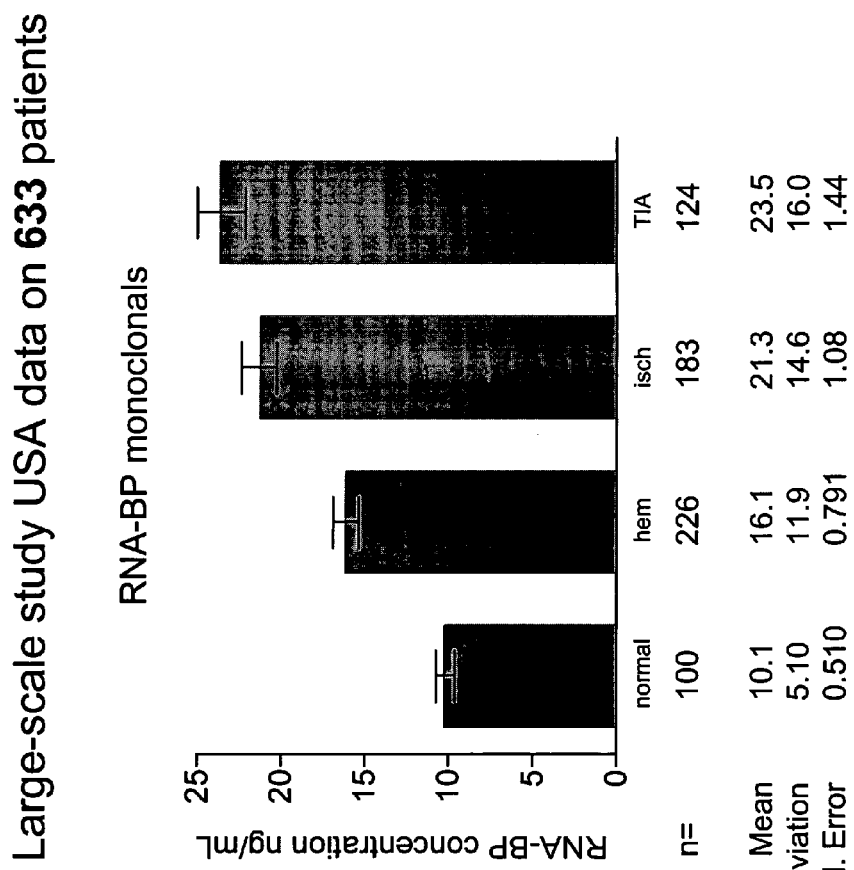
Figure 32: RNA-binding protein in plasma (USA-3)

Figure 33: RNA-binding protein in plasma (USA-3)

| Kruskal-Wallis statistic | 79.78 | | | |
|---|---|---|---|---|
| Dunn's Multiple Comparison Test | P value | CO | SE | SP |
| normal vs hem | P < 0.001 | 9.5 | 68 | 62 |
| normal vs isch | P < 0.001 | 9.5 | 77.6 | 62 |
| normal vs TIA | P < 0.001 | 9.5 | 81.4 | 62 |
| hem vs isch | P < 0.01 | 13.5 | 60 | 54.9 |
| hem vs TIA | P < 0.001 | 15.95 | 64.5 | 63.7 |
| isch vs TIA | P > 0.05 | | | |

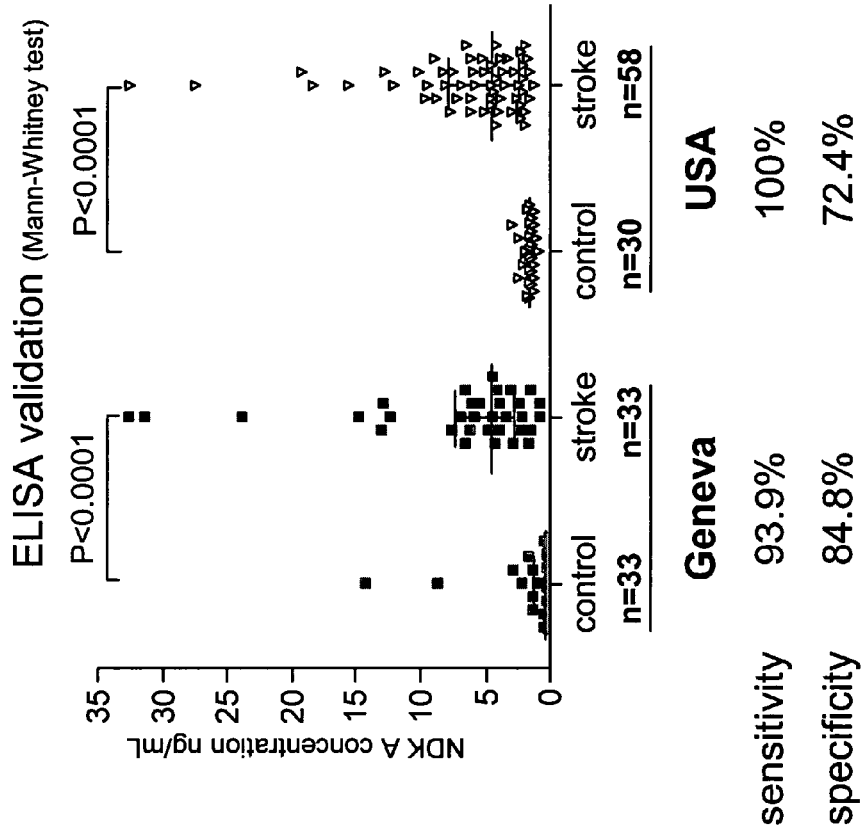
Figure 34: Nucleoside Diphosphate Kinase A

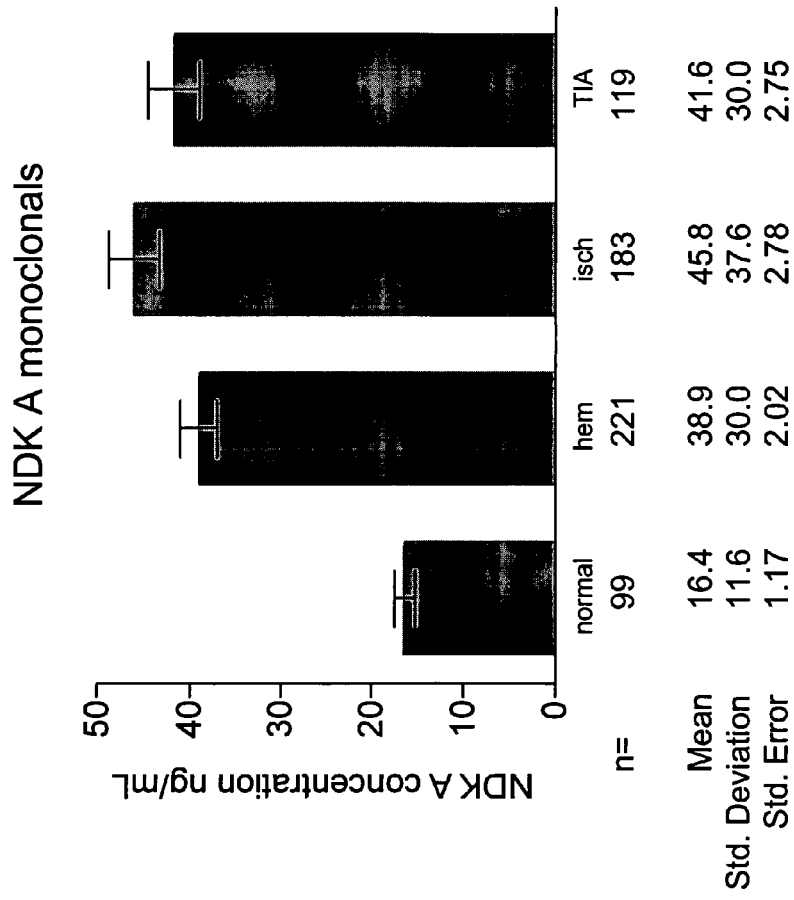
Figure 35: Nucleoside diphosphate kinase A (USA-3)

Figure 36: Nucleoside diphosphate kinase A (USA-3)

| Kruskal-Wallis statistic 109.9 | | | | |
|---|---|---|---|---|
| Dunn's Multiple Comparison Test | P value | CO | SE% | SP% |
| normal vs hem | P < 0.001 | 18 | 81 | 76.7 |
| normal vs isch | P < 0.001 | 18 | 74.8 | 76.7 |
| normal vs TIA | P < 0.001 | 18 | 81.5 | 76.7 |
| hem vs isch | P > 0.05 | | | |
| hem vs TIA | P > 0.05 | | | |
| isch vs TIA | P > 0.05 | | | |

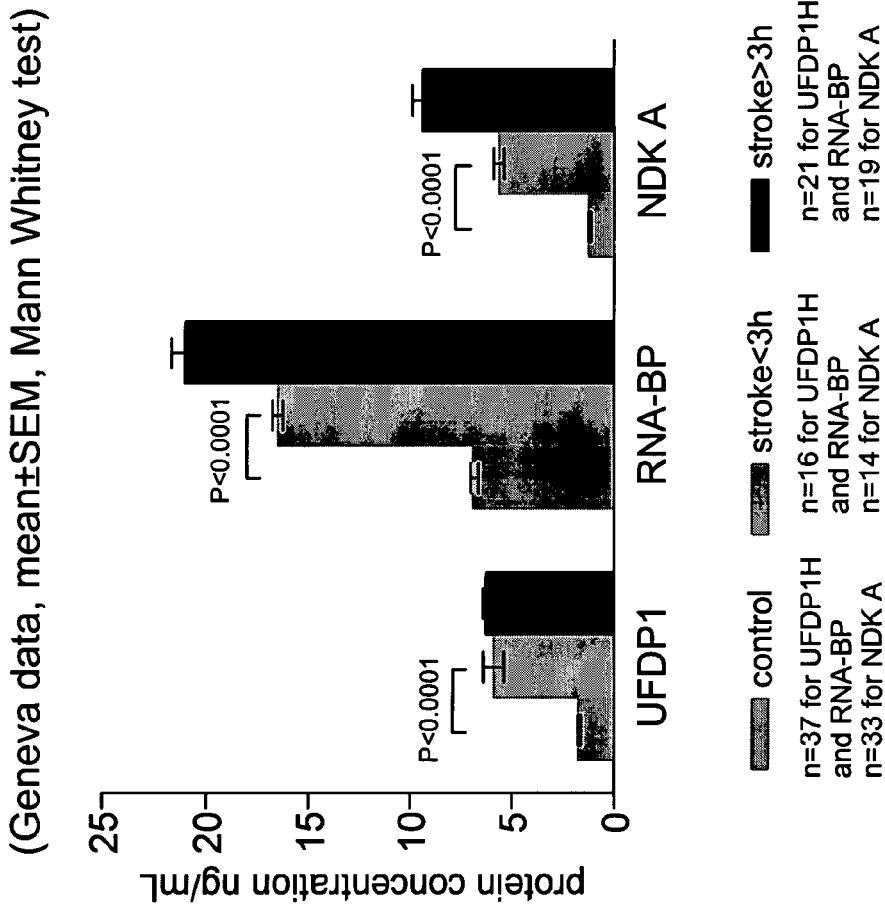
Figure 37: Time onset of symptoms

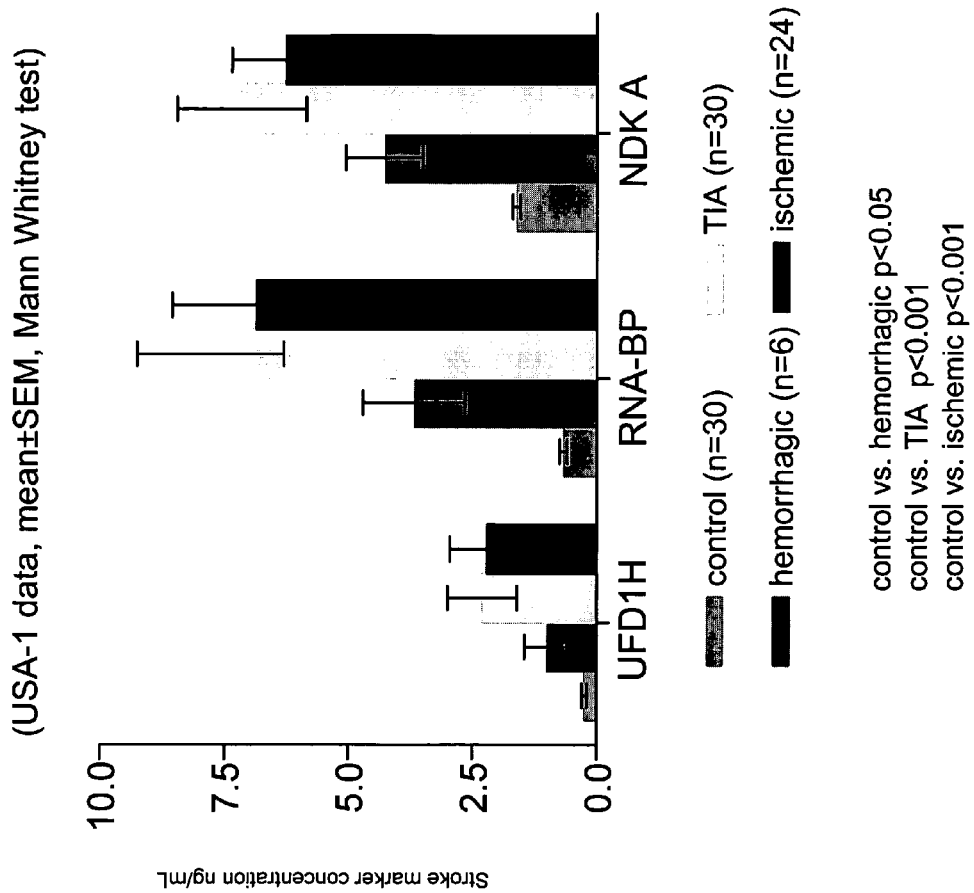
Figure 38: Type of stroke

US 7,955,804 B2

DIAGNOSTIC METHOD FOR BRAIN DAMAGE-RELATED DISORDERS

CROSS-REFERENCE TO RELATED APPLICATION

This application is a continuation of Great Britain Patent Application No. PCT/GB2004/050012 filed Sep. 20, 2004, the entire specification claims and drawings of which are incorporated herewith by reference.

BACKGROUND OF THE INVENTION

1 Field of the Invention

This invention relates to a diagnostic method for brain damage-related disorders. No biological marker is currently available for the routine diagnosis of brain damage-related disorders including cerebrovascular, dementia and neurodegenerative diseases. This invention relates to the use of cerebrospinal fluid from deceased patients as a model for the discovery of brain damage-related disorder markers, and to the use of such markers in diagnosis.

2. Description of the Related Art

Over the last two decades, a number of biological markers (biomarkers) have been studied in the cerebrospinal fluid (CSF) and serum of patients with brain damage-related disorders, including creatine kinase-BB [1], lactate dehydrogenase [2], myelin basic protein [3], S100 protein [4], neuron-specific enolase (NSE) [5], glial fibrillary acidic protein [6] and tau [7]. Most of them have not proved useful indicators of the extent of brain damage and accurate predictors of clinical status and functional outcome. In fact, the diagnostic value of biomarkers for brain damage-related disorders has been hampered by their late appearance and a delayed peak after the damage event, their poor sensitivity and specificity, and the limited understanding of the mechanisms governing the release of these molecules into the CSF and ultimately in the blood. As a result of these limitations, the use of brain damage-related disorder biomarkers is currently limited to research settings and none has been recommended for routine assessment [8].

WO 01/42793 relates to a diagnostic assay for stroke in which the concentration of heart or brain fatty acid binding protein (H-FABP or B-FABP) is determined in a sample of body fluid.

SUMMARY OF THE INVENTION

Ideally, a biomarker for the diagnosis, monitoring and prognosis of brain damage-related disorders should include at least the following characteristics: (1) it should be brain-specific; (2) because of obvious difficulties to obtain CSF samples in patients, detection in serum is highly desirable; (3) it should appear very early; (4) its peak level, alternatively the area under the curve of sequential concentrations, should reflect the extent of brain damage; finally (5) it should be indicative of functional outcome. We demonstrate here new brain damage-related disorder biomarkers and provide a comparison with S100 and NSE, the two molecules, which have been most extensively assessed for this purpose.

We describe how proteins have been identified as new diagnostic biomarkers for brain damage-related disorders using a proteomics-based analysis of CSF from deceased patients as a model of massive brain damage. And we report as an example on results obtained after serum FABP levels have been sequentially determined using an ELISA assay in patients with acute stroke, as compared to S100 and NSE. A diagnostic assay for stroke using FABP has been described in WO 01/42793. Use of the polypeptides according to the present invention can be validated in a similar way.

According to a first object of the invention, compositions are provided which comprise polypeptides for which the level was found increased in the cerebrospinal fluid from deceased patients compared to cerebrospinal fluid from healthy donors. According to this same object, compositions are disclosed which comprise antibodies which are derived from the above polypeptides According to a second object of the invention, methods are provided which utilize the inventive compositions in the diagnosis and prognosis of brain damage-related disorders including cerebrovascular, dementia and neurodegenerative diseases.

The present invention provides the following:

1. A method of diagnosis of a brain damage-related disorder or the possibility thereof in a subject suspected of suffering therefrom, which comprises detecting at least one polypeptide, or a variant or mutant thereof, selected from A-FABP, E-FABP, H-FABP, B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A) in a sample of body fluid taken from the subject.

2. A method according to 1, in which the polypeptide is differentially contained in the body fluid of brain damage-related disorder-affected subjects and non-brain damage-related disorder-affected subjects, and the method includes determining whether the concentration of polypeptide in the sample is consistent with a diagnosis of brain damage-related disorder.

3. A method according to 1 or 2, in which an antibody to the polypeptide is used in the detection or the determination of the concentration.

4. A method according to any of 1 to 3, in which the body fluid is cerebrospinal fluid, plasma, serum, blood, tears, urine or saliva.

5. A method according to any of 1 to 4, in which the polypeptide is present in the body fluid of brain damage-related disorder-affected subjects and not present in the body fluid of non-brain damage-related disorder-affected subjects, whereby the presence of the polypeptide in a body fluid sample is indicative of brain damage-related disorder.

6. A method according to any of 1 to 4, in which the polypeptide is not present in the body fluid of brain damage-related disorder-affected subjects and present in the body fluid of non-brain damage-related disorder-affected subjects, whereby the non-presence of the polypeptide in a body fluid sample is indicative of brain damage-related disorder.

7. A method according to any of 1 to 6, in which a plurality of peptides is determined in the sample.

8. A method according to any of 1 to 7, in which the polypeptide is differentially subject to post-translational modification in the body fluid of brain damage-related disorder-affected subjects and non-brain damage-related disorder-affected subjects, and the method includes detecting the post-translational modification of the polypeptide in the sample and determining whether this is consistent with a diagnosis of a brain damage-related disorder.

9. A method according to 8, in which the post-translational modification comprises N-glycosylation.

10. A method according to any of 1 to 9, in which the brain damage-related disorder is stroke and the polypeptide is Ubiquitin fusion degradation protein 1 homolog.

11. A method according to any of 1 to 9, in which the brain damage-related disorder is stroke and the polypeptide is RNA binding regulatory subunit.

12. A method according to any of 1 to 9, in which the brain damage-related disorder is stroke and the polypeptide is Nucleoside diphosphate kinase A.

13. A method according to any of 10 to 12, in which two or more markers selected from antibodies to Ubiquitin fusion degradation protein 1 homolog, RNA binding regulatory subunit, Nucleoside diphosphate kinase A and H-FABP are used in a single well of an ELISA microtiter plate.

14. A method according to 13, in which all four markers are used in a single well.

15. A method according to any of 10 to 12, in which two or more polypeptides selected from Ubiquitin fusion degradation protein 1 homolog, RNA binding regulatory subunit, Nucleoside diphosphate kinase A and H-FABP are separately assayed, and a predictive algorithm is used for diagnosis.

16. Use of a polypeptide, or a variant or mutant thereof, selected from A-FABP, E-FABP, H-FABP, B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A), or a combination of such polypeptides, for diagnostic, prognostic and therapeutic applications relating to brain damage-related disorders.

17. Use according to 16, in which the polypeptide is differentially contained in a body fluid of brain damage-related disorder-affected subjects and non-brain damage-related disorder-affected subjects.

18. Use for diagnostic, prognostic and therapeutic applications, relating to brain damage-related disorders, of a material which recognises, binds to or has affinity for a polypeptide, or a variant or mutant thereof, selected from A-FABP, E-FABP, H-FABP, B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A).

19. Use according to 18 of a combination of materials, each of which respectively recognises, binds to or has affinity for a polypeptide, or a variant or mutant thereof, selected from A-FABP, E-FABP, H-FABP, B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A).

20. Use according to 18 or 19, in which the or each material is an antibody or antibody chip.

21. Use according to 20, in which the material is an antibody to A-FABP.

22. Use according to 20, in which the material is an antibody to E-FABP.

23. Use according to 20, in which the material is an antibody to PGP 9.5.

24. Use according to 20, in which the material is an antibody to GFAP.

25. Use according to 20, in which the material is an antibody to Prostaglandin D synthase.

26. Use according to 20, in which the material is an antibody to Neuromodulin.

27. Use according to 20, in which the material is an antibody to Neurofilament L.

28. Use according to 20, in which the material is an antibody to Calcyphosine.

29. Use according to 20, in which the material is an antibody to RNA binding regulatory subunit.

30. Use according to 20, in which the material is an antibody to Ubiquitin fusion degradation protein 1 homolog.

31. Use according to 20, in which the material is an antibody to Nucleoside diphosphate kinase A.

32. Use according to 20, in which the material is an antibody to Glutathione S tranferase P.

33. Use according to 20, in which the material is an antibody to Cathepsin D.

34. Use according to 20, in which the material is an antibody to DJ-1 protein.

35. Use according to 20, in which the material is an antibody to Peroxiredoxin 5.

36. Use according to 20, in which the material is an antibody to Peptidyl-prolyl cis-trans isomerase A (Cyclophilin A).

37. An assay device for use in the diagnosis of brain damage-related disorders, which comprises a solid substrate having a location containing a material which recognizes, binds to or has affinity for a polypeptide, or a variant or mutant thereof, selected from A-FABP, E-FABP, H-FABP, B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A).

38. An assay device according to 37, in which the solid substrate has a plurality of locations each respectively containing a material which recognizes, binds to or has affinity for a polypeptide, or a variant or mutant thereof, selected from A-FABP, E-FABP, H-FABP, B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A).

39. An assay device according to 37 or 38, in which the material is an antibody or antibody chip.

40. An assay device according to 39, which has a unique addressable location for each antibody, thereby to permit an assay readout for each individual polypeptide or for any combination of polypeptides.

41. An assay device according to any of 37 to 40, including an antibody to A-FABP.

42. An assay device according to any of 37 to 40, including an antibody to E-FABP.

43. An assay device according to any of 37 to 40, including an antibody to PGP 9.5.

44. An assay device according to any of 37 to 40, including an antibody to GFAP.

45. An assay device according to any of 37 to 40, including an antibody to Prostaglandin D synthase.

46. An assay device according to any of 37 to 40, including an antibody to Neuromodulin.

47. An assay device according to any of 37 to 40, including an antibody to Neurofilament L.

48. An assay device according to any of 37 to 40, including an antibody to Calcyphosine.

49. An assay device according to any of 37 to 40, including an antibody to RNA binding regulatory subunit.

50. An assay device according to any of 37 to 40, including an antibody to Ubiquitin fusion degradation protein 1 homolog.

51. An assay device according to any of 37 to 40, including an antibody to Nucleoside diphosphate kinase A.

52. An assay device according to any of 37 to 40, including an antibody to Glutathione S tranferase P.

53. An assay device according to any of 37 to 40, including an antibody to Cathepsin D.

54. An assay device according to any of 37 to 40, including an antibody to DJ-1 protein.

55. An assay device according to any of 37 to 40, including an antibody to Peroxiredoxin 5.

56. An assay device according to any of 37 to 40, including an antibody to Peptidyl-prolyl cis-trans isomerase A (Cyclophilin A).

57. A kit for use in the diagnosis of brain damage-related disorders, comprising an assay device according to any of 37 to 56, and means for detecting the amount of one or more of the polypeptides in a sample of body fluid taken from a subject.

The new markers used in the present invention are as follows: A-FABP (P15090), which has the sequence (SEQ ID NO.1):

```
  1 CDAFVGTWKLVSSENFDDYMKEVGVGFATRKVAGMAKPNMIISVNGDV
    ITIKSESTFKNTEISFILGQEFDEVTADDRKVKSTITLDGGVLVHVQKWD
  5 GKSTTIKRKREDDKLVVECVMKGVTSTRVYERA 131
```

E-FABP (Q01469), which has the sequence (SEQ ID NO.2):

```
  1 MATVQQLEGRWRLVDSKGFDEYMKELGVGIALRKMGAMAKPDCIITCD
    GKNLTIKTESTLKTTQFSCTLGEKFEETTADGRKTQTVCNFTDGALVQHQ
    EWDGKESTITRKLKDGKLVVECVMNNVTCTRIYEKVE 135
```

PGP 9.5 (P09936), which has the sequence (SEQ ID NO.3):

```
  1 MQLKPMEINP EMLNKVLSRL GVAGQWRFVD VLGLEEESLG SVPAPACALL LLFPLTAQHE

60 NFRKKQIEEL KGQEVSPKVY FMKQTIGNSC GTIGLIHAVA NNQDKLGFED GSVLKQFLSE

120 TEKMSPEDRA KCFEKNEAIQ AAHDAVAQEG QCRVDDKVNF HFILFNNVDG HLYELDGRMP

180 FPVNHGASSE DTLLKDAAKV CREFTEREQG EVRFSAVALC KAA

223
```

GFAP (P14136), which has the sequence (SEQ ID NO.4):

```
  1 MERRRITSAA RRSYVSSGEM MVGGLAPGRR LGPGTRLSLA RMPPPLPTRV DFSLAGALNA

60 GFKETRASER AEMMELNDRF ASYIEKVRFL EQQNKALAAE LNQLRAKEPT KLADVYQAEL

120 RELRLRLDQL TANSARLEVE RDNLAQDLAT VRQKLQDETN LRLEAENNLA AYRQEADEAT

180 LARLDLERKI ESLEEEIRFL RKIHEEEVRE LQEQLARQQV HVELDVAKPD LTAALKEIRT

240 QYEAMASSNM HEAEEWYRSK FADLTDAAAR NAELLRQAKH EANDYRRQLQ SLTCDLESLR

300 GTNESLERQM REQEERHVRE AASYQEALAR LEEEGQSLKD EMARHLQEYQ DLLNVKLALD

360 IEIATYRKLL EGEENRITIP VQTFSNLQIR ETSLDTKSVS EGHLKRNIVV KTVEMRDGEV

420 IKESKQEHKD VM

432
```

Prostaglandin D synthase (P41222), which has the sequence (SEQ ID NO.5):

```
 23 APEAQVSV QPNFQQDKFL GRWFSAGLAS NSSWLREKKA

60 ALSMCKSVVA PATDGGLNLT STFLRKNQCE TRTMLLQPAG SLGSYSYRSP HWGSTYSVSV

120 VETDYDQYAL LYSQGSKGPG EDFRMATLYS RTQTPRAELK EKFTAFCKAQ GFTEDTIVFL

180 PQTDKCMTEQ
```

Neuromodulin (P17677), which has the sequence (SEQ ID NO.6):

```
  1 MLCCMRRTKQ VEKNDDDQKI EQDGIKPEDK AHKAATKIQA SFRGHITRKK LKGEKKDDVQ

60 AAEAEANKKD EAPVADGVEK KGEGTTTAEA APATGSKPDE PGKAGETPSE EKKGEGDAAT

120 EQAAPQAPAS SEEKAGSAET ESATKASTDN SPSSKAEDAP AKEEPKQADV PAAVTAAAAT

180 TPAAEDAAAK ATAQPPTETG ESSQAEENIE AVDETKPKES ARQDEGKEEE PEADQEHA

238
```

Neurofilament L (P07196), which has the sequence (SEQ ID NO.7):

```
  1 SSFSYEPYYS TSYKRRYVET PRVHISVRSG YSTARSAYSS YSAPVSSSLS VRRSYSSSSG

60 SLMPSLENLD LSQVAAISND LKSIRTQEKA QLQDLNDRFA SFIERVHELE QQNKVLEAEL

120 LVLRQKHSEP SRFRALYEQE IRDLRLAAED ATTNEKQALR GEREEGLEET LRNLQARYEE

180 EVLSREDAEG RLMERRKGAD EAALARAELE KRIDSLMDEI SFLKKVHEEE IAELQAQIQY

240 AQISVEMDVT KPDLSAALKD IRAQYEKLAA KNMQNAEEWF KSRFTVLTES AAKNTDAVRA

300 AKDEVSESRR LLKAKTLEIE ACRGMNEALE KQLQELEDKQ NADISAMQDT INKLENELRT

360 TKSEMARYLK EYQDLLNVKM ALDIEIAAYR KLLEGEETRL SFTSVGSITS GYSQSSQVFG

420 RSAYGGLQTS SYLMSTRSFP SYYTSHVQEE QTEVEETIEA SKAEEAKDEP PSEGEAEEEE

480 KDKEEAEEEE AAEEEEAAKE ESEEAKEEEE GGEGEEGEET KEAEEEEKKV EGAGEEQAAK

540 KKD

543
```

Calcyphosine (Q13938), which has the sequence (SEQ ID NO.8):

```
  1 MDAVDATMEK LRAQCLSRGA SGIQGLARFF RQLDRDGSRS LDADEFRQGL AKLGLVLDQA

60 EAEGVCRKWD RNGSGTLDLE EFLRALRPPM SQAREAVIAA AFAKLDRSGD GVVTVDDLRG

120 VYSGRAHPKV RSGEWTEDEV LRRFLDNFDS SEKDGQVTLA EFQDYYSGVS ASMNTDEEFV

180 AMMTSAWQL

189
```

RNA binding regulatory subunit (O14805), also referred to as RNA-BP, which has the sequence (SEQ ID NO.9):

```
  1 MASKRALVIL AKGAEEMETV IPVDVMRRAG IKVTVAGLAG KDPVQCSRDV VICPDASLED

60 AKKEGPYDVV VLPGGNLGAQ NLSESAAVKE ILKEQENRKG LIAAICAGPT ALLAHEIGFG

120 SKVTTHPLAK DKMMNGGHYT YSENRVEKDG LILTSRGPGT SFEFALAIVE ALNGKEVAAQ

180 VKAPLVLKD

189
```

Ubiquitin fusion degradation protein 1 homolog (Q92890), also referred to as UFD1 or UFDP1, which has the sequence (SEQ ID NO.10):

```
  1 MFSFNMFDHP IPRVFQNRFS TQYRCFSVSM LAGPNDRSDV EKGGKIIMPP SALDQLSRLN

60 ITYPMLFKLT NKNSDRMTHC GVLEFVADEG ICYLPHWMMQ NLLLEEDGLV QLETVNLQVA

120 TYSKSKFCYL PHWMMQNLLL EEGGLVQVES VNLQVATYSK FQPQSPDFLD ITNPKAVLEN

180 ALRNFACLTT GDVIAINYNE KIYELRVMET KPDKAVSIIE CDMNVDFDAP LGYKEPERQV

240 QHEESTEGEA DHSGYAGELG FRAFSGSGNR LDGKKKGVEP SPSPIKPGDI KRGIPNYEFK

300 LGKITFIRNS RPLVKKVEED EAGGRFVAFS GEGQSLRKKG RKP

343
```

Nucleoside diphosphate kinase A (P15531), also referred to as NDK A, which has the sequence (SEQ ID NO.11):

```
  1 MANCERTFIA IKPDGVQRGL VGEIIKRFEQ KGFRLVGLKF MQASEDLLKE HYVDLKDRPF

60 FAGLVKYMHS GPVVAMVWEG LNVVKTGRVM LGETNPADSK PGTIRGDFCI QVGRNIIHGS

120 DSVESAEKEI GLWFHPEELV DYTSCAQNWI YE

152
```

Glutathione S tranferase P (P09211), which has the sequence (SEQ ID NO.12):

```
  1 PPYTVVYFPV RGRCAALRML LADQGQSWKE EVVTVETWQE GSLKASCLYG QLPKFQDGDL

60 TLYQSNTILR HLGRTLGLYG KDQQEAALVD MVNDGVEDLR CKYISLIYTN YEAGKDDYVK

120 ALPGQLKPFE TLLSQNQGGK TFIVGDQISF ADYNLLDLLL IHEVLAPGCL DAFPLLSAYV

180 GRLSARPKLK AFLASPEYVN LPINGNGKQ

209
```

Cathepsin D (P07339), which has the sequence (SEQ ID NO.13):

```
 65 GPIPEV LKNYMDAQYY GEIGIGTPPQ CFTVVFDTGS SNLWVPSIHC KLLDIACWIH

120 HKYNSDKSST YVKNGTSFDI HYGSGSLSGY LSQDTVSVPC QSASSASALG GVKVERQVFG

180 EATKQPGITF IAAKFDGILG MAYPRISVNN VLPVFDNLMQ QKLVDQNIFS FYLSRDPDAQ

240 PGGELMLGGT DSKYYKGSLS YLNVTRKAYW QVHLDQVEVA SGLTLCKEGC EAIVDTGTSL

300 MVGPVDEVRE LQKAIGAVPL IQGEYMIPCE KVSTLPAITL KLGGKGYKLS PEDYTLKVSQ

360 AGKTLCLSGF MGMDIPPPSG PLWILGDVFI GRYYTVFDRD NNRVGFAEAA RL

412
```

DJ-1 protein (Q99497), which has the sequence (SEQ ID NO.14):

```
  1 MASKRALVIL AKGAEEMETV IPVDVMRRAG IKVTVAGLAG KDPVQCSRDV VICPDASLED

60 AKKEGPYDVV VLPGGNLGAQ NLSESAAVKE ILKEQENRKG LIAAICAGPT ALLAHEIGCG

120 SKVTTHPLAK DKMMNGGHYT YSENRVEKDG LILTSRGPGT SFEFALAIVE ALNGKEVAAQ

180 VKAPLVLKD

189
```

Peroxiredoxin 5 (P30044), which has the sequence (SEQ ID NO.15):

```
  1 MGLAGVCALR RSAGYILVGG AGGQSAAAAA RRCSEGEWAS GGVRSFSRAA AAMAPIKVGD

60 AIPAVEVFEG EPGNKVNLAE LFKGKKGVLF GVPGAFTPGC SKTHLPGFVE QAEALKAKGV

120 QVVACLSVND AFVTGEWGRA HKAEGKVRLL ADPTGAFGKE TDLLLDDSLV SIFGNRRLKR

180 FSMVVQDGIV KALNVEPDGT GLTCSLAPNI ISQL
214
```

Peptidyl-prolyl cis-trans isomerase A (Cyclophilin A) (P05092), which has the sequence (SEQ ID NO.16):

```
  1 VNPTVFFDIA VDGEPLGRVS FELFADKVPK TAENFRALST GEKGFGYKGS CFHRIIPGFM

60 CQGGDFTRHN GTGGKSIYGE KFEDENFILK HTGPGILSMA NAGPNTNGSQ FFICTAKTEW

120 LDGKHVVFGK VKEGMNIVEA MERFGSRNGK TSKKITIADC GQLE
164
```

The polypeptides useful in the present invention are not restricted to the above sequences, and include variants and mutants thereof. A variant is defined as a naturally occurring variation in the sequence of a polypeptide which has a high degree of homology with the given sequence, and which has substantially the same functional and immunological properties. A mutant is defined as an artificially created variant. A high degree of homology is defined as at least 90%, preferably at least 95% and most preferably at least 99% homology. Variants may occur within a single species or between different species. The above sequences are of human origin, but the invention encompasses use of the corresponding polypeptides from other mammalian species, e.g. bovine animals.

Brain damage-related disorders in the context of the present invention include the following: head trauma, ischemic stroke, hemorrhagic stroke, subarachnoid hemorrhage, intra cranial hemorrhage, transient ischemic attack, vascular dementia, corticobasal ganglionic degeneration, encephalitis, epilepsy, Landau-Kleffner syndrome, hydrocephalus, pseudotumor cerebri, thalamic diseases, meningitis, myelitis, movement disorders, essential tremor, spinal cord diseases, syringomyelia, Alzheimer's disease (early onset), Alzheimer's disease (late onset), multi-infarct dementia, Pick's disease, Huntingdon's disease, Parkinson, Parkinson syndromes, frontotemporal dementia, corticobasal degeneration, multiple system atrophy, progressive supranuclear palsy, Lewy body disease, amyotrophic lateral sclerosis, Creutzfeldt-Jakob disease, Dandy-Walker syndrome, Friedreich ataxia, Machado-Joseph disease, migraine, schizophrenia, mood disorders and depression. Corresponding disorders in non-human mammals are also included, such as transmissible spongiform encephalopathies (TSEs), e.g. bovine spongiform encephalopathy (BSE) in cattle or scrapie in sheep.

H-FABP (P05413) and B-FABP (O15540) are also useful in the present invention for diagnosis of brain damage-related disorders or the possibility thereof, especially those other than stroke and CJD.

Other features and advantages of the present invention will become apparent from the following description of the invention which refers to the accompanying drawings.

BRIEF DESCRIPTION OF THE DRAWINGS

FIG. 6 shows ELISA intensity values for marker polypeptides obtained in a survey of stroke patients;

FIG. 7 shows UFD1 detection in plasma samples from said survey;

FIG. 8 is an ROC curve of UFD1 from the data in FIG. 7;

FIG. 9 shows UFD1 detection corresponding to FIG. 7;

FIG. 10 shows RNA-BP detection in plasma samples from said survey;

FIG. 11 is an ROC curve of RNA-BP from the data in FIG. 10;

FIG. 12 shows RNA-BP detection corresponding to FIG. 10;

FIG. 13 shows NDK A detection in plasma samples from said survey;

FIG. 14 is an ROC curve of NDK A from the data in FIG. 13;

FIG. 15 shows NDK A detection corresponding to FIG. 13;

FIG. 18 shows ELISA intensity values for H-FABP obtained in a survey of stroke patients and a control group;

FIG. 19 shows UFDP-1 spot intensities on mini-2-DE-gels prepared with CSF from a control and a deceased patient;

FIG. 20 shows UFDP1 plasma concentration measured by ELISA for two cohorts of stroke patients and controls from Geneva and from the USA;

FIG. 21 shows RNA-BP spot intensities on mini-2-DE-gels prepared with CSF from a control and a deceased patient;

FIG. 22 shows RNA-BP plasma concentration measured by ELISA for three studies of controls and stroke patients;

FIG. 23 shows NDKA spot intensities on mini-2-DE-gels prepared with CSF from a control and a deceased patient;

FIG. 24 shows NDKA plasma concentration measured by ELISA for two cohorts of stroke patients and controls from Geneva and from the USA;

FIG. 25a shows the time onset of symptoms, showing the stroke marker (SM) concentration for UFDP 1, RNA-BP and NDKA, in each case respectively for controls, stroke patients at less than 3 hours from the time of cerebrovascular accident, and stroke patients at more than 3 hours from the time of cerebrovascular accident;

FIG. 25b shows data for type of stroke, showing the stroke marker concentration for UFDP1, RNA-BP and NDKA, in each case respectively for controls, hemorrhagic stroke patients, transient ischemic attack(TIA) patients and ischemic stroke patients;

FIG. 26 is a summary of information for a panel of early plasmatic markers of stroke;

FIG. 27 shows ELISA intensity values for a mix of UFD1, RNA-BP, NDKA and H-FABP in the same well;

FIG. 28 is a graphic representation of combinations of two out of the four biomarkers from FIG. 27, showing selected cut-off values for diagnosis;

FIGS. 29A and 29B show information related to 37 stroke and 37 age/sex matched control plasma samples in a further study. Diagnosis (Diag) is shown as I (ischemic stroke), H (hemorrhagic stroke), TIA (transient ischemic attack) or ctrl (control). The concentrations determined by ELISA of UFD 1, RNA-BP and NDK A are also shown. ELISA was performed as previously described;

FIG. 30 shows the results from this further study for 37 stroke and 37 control plasma samples tested in Geneva for UFD1. USA-1 (non age sex matched controls) data for UFD1;

FIG. 31 shows the results from this further study for 37 stroke and 37 control plasma samples tested in Geneva for RNA-BP. USA-1 (non age sex matched controls) and USA-2 (age sex matched controls) data for RNA-BP;

FIG. 32 shows the results of a large scale study USA3 on 633 patients for RNA-BP;

FIG. 33 shows a statistical analysis (Kruskal-Wallis) on USA-3 for RNA-BP;

FIG. 34 shows results for 33 stroke and 33 control plasma samples tested in Geneva for NDKA. USA-1 (non age sex matched controls) data for NDK A;

FIG. 35 shows results of a large scale study USA3 on 622 patients for NDKA;

FIG. 36 shows a statistical analysis (Kruskal-Wallis) on USA-3 for NDK A;

FIG. 37 shows stroke marker concentration as a function of time onset of symptoms (Geneva data, new 37 stroke and 37 control plasma samples);

FIG. 38 shows stroke marker concentration as a function of type of stroke (hemorrhagic, ischemic, TIA) using USA-1 data.

DETAILED DESCRIPTION OF THE PREFERRED EMBODIMENTS

Figure 1:
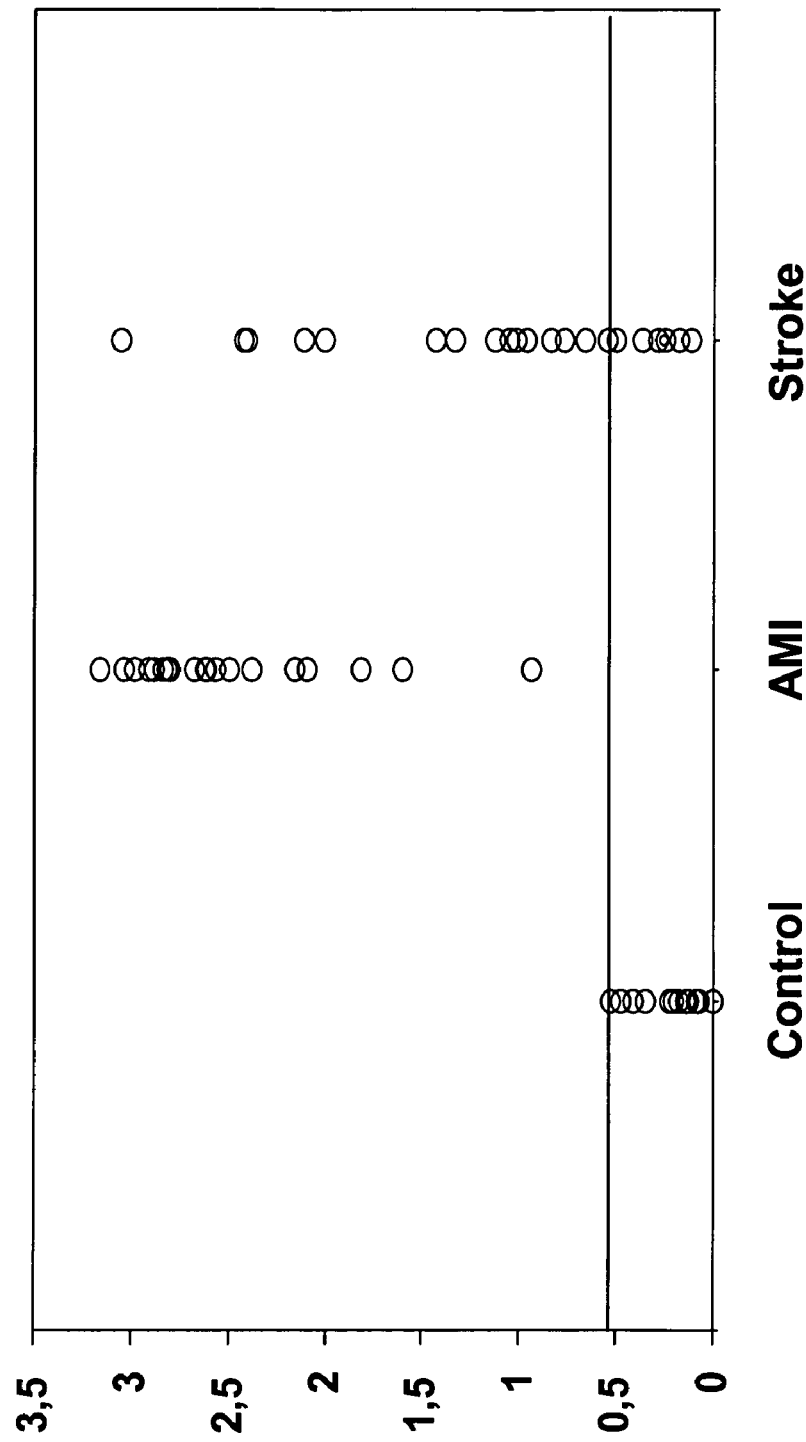
FIG. 1 shows results of an assay for H-FABP (measured in OD units on the vertical axis) for three groups of patients: a control group, a group with acute myocardial infarction (AMI), and a group with acute stroke.

The invention presented here is directed towards compositions and methods for detecting increasing or reducing polypeptides levels in body fluids including blood components (e.g. plasma or serum) or cerebrospinal fluid from patients affected by a brain damage-related disorder including cerebrovascular, dementia and neurodegenerative diseases. For this purpose, use can be made of antibodies or any specific polypeptide detection method.

Antibodies against brain damage protein markers, in particular their protein-binding domains, are suitable as detection tools. Molecular biological and biotechnological methods can be used to alter and optimize the antibody properties of the said molecules in a specific manner. In addition to this, the antibodies can be modified chemically, for example by means of acetylation, carbamoylation, formylation, biotinylation, acylation, or derivatization with polyethylene glycol or hydrophilic polymers, in order to increase their stability.

A specific polypeptide marker selected from A-FABP, E-FABP and any other FABP, i.e. H-FABP or B-FABP, PGP 9.5, GFAP, Prostaglandin D synthase, Neuromodulin, Neurofilament L, Calcyphosine, RNA binding regulatory subunit, Ubiquitin fusion degradation protein 1 homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A) is determined in a body fluid sample, for example by using an antibody thereto. The marker is preferably measured by an immunoassay, using a specific antibody to the polypeptide and measuring the extent of the antigen (polypeptide)/antibody interaction. The antibody may be a monoclonal antibody or an engineered (chimeric) antibody. Antibodies to the polypeptides are known and are commercially available. Also, the usual Kohler-Milstein method may be used to raise antibodies. Less preferably, the antibody may be polyclonal. In the context of the present invention, the term "antibodies" includes binding fragments of antibodies, such as single chain or Fab fragments.

Any known method of immunoassay may be used. In a sandwich assay an antibody (e.g. polyclonal) to the polypeptide is bound to the solid phase such as a well of a plastics microtitre plate, and incubated with the sample and with a labelled second antibody specific to the polypeptide to be detected. Alternatively, an antibody capture assay (also called "indirect immunoassay") can be used. Here, the test sample is allowed to bind to a solid phase, and the anti-polypeptide antibody (polyclonal or monoclonal) is then added and allowed to bind. If a polyclonal antibody is used in this context, it should desirably be one which exhibits a low cross-reactivity with other forms of polypeptide. After washing away unbound material, the amount of antibody bound to the solid phase is determined using a labelled second antibody, anti- to the first.

A direct assay can be performed by using a labelled anti-polypeptide antibody. The test sample is allowed to bind to the solid phase and the anti-polypeptide antibody is added. After washing away unbound material, the amount of antibody bound to the solid phase is determined. The antibody can be labelled directly rather than via a second antibody.

In another embodiment, a competition assay can be performed between the sample and a labelled polypeptide or a peptide derived therefrom, these two antigens being in competition for a limited amount of anti-polypeptide antibody bound to a solid support. The labelled polypeptide or peptide can be pre-incubated with the antibody on the solid phase, whereby the polypeptide in the sample displaces part of the polypeptide or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

Throughout, the label is preferably an enzyme. The substrate for the enzyme may be colour-forming, fluorescent, chemiluminescent or electrochemical, and can be soluble or precipitating. Alternatively, the label may be a radioisotope or fluorescent, e.g. using conjugated fluorescein.

The enzyme may, for example, be alkaline phosphatase or horseradish peroxidase and can conveniently be used colorimetrically, e.g. using p-nitrophenyl phosphate as a yellow-forming substrate with alkaline phosphatase.

For a chemiluminescent assay, the antibody can be labelled with an acridinium ester or horseradish peroxidase. The latter is used in enhanced chemiluminescent (ECL) assay. Here, the antibody, labelled with horseradish peroxidase, participates in a chemiluminescent reaction with luminol, a peroxide substrate and a compound, which enhances the intensity and duration of the emitted light, typically, 4-iodophenol or 4-hydroxycinnamic acid.

An amplified immunoassay such as immuno-PCR can be used. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 1995; 23, 522-529 (1995) or T. Sano et al., in "Molecular Biology and Biotechnology" ed. Robert A. Meyers, VCH Publishers, Inc. (1995), pages 458-460. The signal is read out as before.

In one procedure, an enzyme-linked immunosorbent assay (ELISA) can be used to detect the polypeptide.

The use of a rapid microparticle-enhanced turbidimetric immunoassay, developed for H-FABP in the case of AMI, M. Robers et al., "Development of a rapid microparticle-enhanced turbidimetric immunoassay for plasma fatty acid-binding protein, an early marker of acute myocardial infarction", Clin. Chem. 1998;44:1564-1567, significantly decreases the time of the assay. Thus, the full automation in a widely used clinical chemistry analyser such as the COBAST™ MIRA Plus system from Hoffmann-La Roche, described by M. Robers et al. supra, or the AxSYM™ system from Abbott Laboratories, should be possible and applied for routine clinical diagnosis of brain damage-related disorders.

The polypeptide concentrations can be measured by other means than immunoassay. For example, the sample can be subjected to 2D-gel electrophoresis and the amount of the polypeptide estimated by densitometric scanning of the gel or of a blot therefrom. However, it is desirable to carry out the assay in a rapid manner, so that the patient can be treated promptly.

In principle, any body fluid can be used to provide a sample for diagnosis, but preferably the body fluid is cerebrospinal fluid (CSF), plasma, serum, blood, urine, tears or saliva.

According to the invention, a diagnosis of brain damage-related disorders may be made from determination of a single polypeptide or any combination of two or more of the polypeptides.

The invention also relates to the use of one or more of the specified polypeptides which is differentially contained in a body fluid of brain damage-affected subjects and non-brain damage-affected subjects, for diagnostic, prognostic and therapeutic applications. This may involve the preparation and/or use of a material which recognizes, binds to or has some affinity to the above-mentioned polypeptide. Examples of such materials are antibodies and antibody chips. The term "antibody" as used herein includes polyclonal antiserum, monoclonal antibodies, fragments of antibodies such as Fab, and genetically engineered antibodies. The antibodies may be chimeric or of a single species. The above reference to "prognostic" applications includes making a determination of the likely course of a brain damage-related disorder by, for example, measuring the amount of the above-mentioned polypeptide in a sample of body fluid. The above reference to "therapeutic follow-up" applications includes making a determination of the likely course of a brain damage-related disorder by, for example, measuring the amount of the above-mentioned polypeptide in a sample of body fluid (and evaluating its level as a function of the treatment, the disability recovery or not, the size of the lesions etc.). The above reference to "therapeutic" applications includes, for example, preparing materials which recognize, bind to or have affinity to the above-mentioned polypeptides, and using such materials in therapy. The materials may in this case be modified, for example by combining an antibody with a drug, thereby to target the drug to a specific region of the patient.

The above reference to "presence or absence" of a polypeptide should be understood to mean simply that there is a significant difference in the amount of a polypeptide which is detected in the affected and non-affected sample. Thus, the "absence" of a polypeptide in a test sample may include the possibility that the polypeptide is actually present, but in a significantly lower amount than in a comparative test sample. According to the invention, a diagnosis can be made on the basis of the presence or absence of a polypeptide, and this includes the presence of a polypeptide in a significantly lower or significantly higher amount with reference to a comparative test sample.

The above references to "detecting" a polypeptide should be understood to include a reference to compositions and methods for detecting post-translational modifications of the polypeptides in addition to quantitative variations.

As an example, we detected differences in the post-translational modifications pattern of prostaglandin D synthase between post-mortem and control CSF. Similar differences were also detected between CSF from a patient suffering from Creutzfeldt-Jakob disease and control CSF. This is described in Example 5 below. The invention therefore encompasses the detection of post-translational modifications in general, and determining whether such modifications of a polypeptide are consistent with a diagnosis of a brain damage-related disorder.

Kits and assay devices for use in diagnosis of brain damage-related disorders are also within the scope of the invention. These may include one or more antibodies to a polypeptide selected from A-FABP, E-FABP and any other FABP, i.e. H-FABP or B-FABP, PGP 9.5, GFAP, Prostaglandin D synthase, Neuromodulin, Neurofilament L, Calcyphosine, RNA binding regulatory subunit, Ubiquitin fusion degradation protein I homolog, Nucleoside diphosphate kinase A, Glutathione S tranferase P, Cathepsin D, DJ-1 protein, Peroxiredoxin 5 and Peptidyl-prolyl cis-trans isomerase A (Cyclophilin A). The antibodies will bind to the appropriate polypeptides in a fluid sample taken from a patient. The antibodies may be immobilised on a solid support. Preferably, each antibody is placed in a unique addressable location, thereby to permit separated assay readout for each individual polypeptide in the sample, as well as readouts for any selected combination of polypeptides.

The following Examples illustrate the invention.

EXAMPLE 1

Using two-dimensional gel electrophoresis (2-DE) separation of cerebrospinal fluid (CSF) proteins and mass spectrometry techniques, 15 polypeptides named in Table 1 were found elevated or decreased in the CSF of deceased patients, used as a model of massive brain damage.

Study Population and Samples Handling

Eight CSF samples were used for the proteomics-based approach aiming at discovering brain damage-related disorder markers. Four of these samples were obtained at autopsy from deceased patients 6 hours after death with no pathology of the central nervous system. Four others were collected by lumbar puncture from living patients who had a neurological workup for benign conditions unrelated to brain damage (atypical headache and idiopathic peripheral facial nerve palsy). CSF samples were centrifuged immediately after collection, aliquoted, frozen at −80° C. and stored until analysis.

CSF 2-DE

All reagents and apparatus used have been described in detail elsewhere [9]. 250 μl of CSF were mixed with 500 μl of ice-cold acetone (−20° C.) and centrifuged at 10000 g at 4° C. for 10 minutes. The pellet was mixed with 10 μl of a solution containing 10% SDS (w/v) and 2.3% DTE (w/v). The sample was heated to 95° C. for 5 minutes and then diluted to 60 μl with a solution containing 8M urea, 4% CHAPS (w/v), 40 mM Tris, 65 mM DTE and a trace of bromophenol blue. The whole final diluted CSF sample corresponding to 45 μg was loaded in a cup at the cathodic end of the IPG strips. 2-DE was performed as described previously [10]. In brief, the first dimensional protein separation was performed using a commercial 18cm non-linear IPG going from pH 3.5 to 10 from Amersham Biosciences (Uppsala, Sweden). The second dimensional separation was performed onto in-house manufactured vertical gradient slab gels (9-16% T, 2.6% C). Analytical gels were then stained with ammoniacal silver staining [11]. Gels were scanned using a laser densitometer (Amersham Biosciences, Uppsala, Sweden). 2-DE computer image analysis was carried out with the MELANIE 3 software package [12].

Mass Spectrometry Identification

Differentially expressed spots were found through the comparison of analytical gels of deceased vs. healthy CSF (n=4). Spots of interest were analysed by peptide mass fingerprinting using a matrix-assisted laser desorption/ionization time-of-flight mass spectrometer (PerSeptive Biosystems Voyager STR MALDI-TOF-MS, Framingham, Mass., USA) [10] and identified through database using the Peptident tool (http://www.expasy.ch/sprot/peptident.html).

TABLE 1

| A-FABP | P15090 |
| E-FABP | Q01469 |
| PGP 9.5 | P09936 |
| GFAP | P14136 |
| Prostaglandin D synthase | P41222 |
| Neuromodulin | P17677 |
| Neurofilament L | P07196 |
| Calcyphosine | Q13938 |
| RNA binding regulatory subunit | O14805 |
| Ubiquitin fusion degradation protein 1 homolog | Q92890 |
| Nucleoside diphosphate kinase A | P15531 |
| Glutathione S tranferase P | P09211 |
| Cathepsin D | P07339 |
| H-FABP | P05413 |
| B-FABP | O15540 |

EXAMPLE 2

Using two-dimensional gel electrophoresis (2-DE) separation of cerebrospinal fluid (CSF) proteins and mass spectrometry techniques, FABP was found elevated in the CSF of deceased patients, used as a model of massive brain damage. Since H-FABP, a FABP form present in many organs, is also localised in the brain, an enzyme-linked immunosorbant assay (ELISA) was developed to detect H-FABP in stroke vs. control plasma samples. However, H-FABP being also a marker of acute myocardial infarction (AMI), Troponin-I and creatine kinase-MB (CK-MB) levels were assayed at the same time in order to exclude any concomitant heart damage. NSE and S100B levels were assayed simultaneously.

Study Population and Samples Handling

The population used for the assessment in plasma of the various markers detailed below included a total of 64 prospectively studied patients (Table 2) equally distributed into three groups: (1) a Control group including 14 men and 8 women aged 65 years (ranges: 34-86 years) with no known peripheral or central nervous system condition; (2) a group of patients with acute myocardial infarction (AMI group) including 14 men and 6 women aged 65 years (ranges: 29 to 90 years); the diagnosis of AMI was established in all cases by typical electrocardiography modifications and elevated levels of CK-MB (above a cut-off value of 9.3 ng/ml) and of Troponin-I (above a cut-off value of 2 ng/ml) ; (3) a group of patients with acute stroke (Stroke group) including 14 men and 8 women aged 65 years (ranges: 30 to 87 years); the diagnosis of stroke was established by a trained neurologist and was based on the sudden appearance of a focal neurological deficit and the subsequent delineation of a lesion consistent with the symptoms on brain CT or MRI images, with the exception of transient ischemic attacks (TIAs) where a visible lesion was not required for the diagnosis. The Stroke group was separated according to the type of stroke (ischemia or haemorrhage), the location of the lesion (brainstem or hemisphere) and the clinical evolution over time (TIA when complete recovery occurred within 24 hours, or established stroke when the neurological deficit was still present after 24 hours).

TABLE 2

| | Group | | |
|---|---|---|---|
| | Control | AMI | Stroke |
| Diagnosis | | | |
| Number | 22 | 20 | 22 |
| Stroke | | | 22 |
| H-FABP | | | |
| OD > 0.531 | 0 | 20 | 15 |
| OD < 0.531 | 22 | 0 | 7 |
| Troponin-1 | | | |
| >2 ng/ml | 0 | 20 | 1 |
| <2 ng/ml | 22 | 0 | 21 |

| Stroke | | | | | |
|---|---|---|---|---|---|
| Diagnosis | | Location | | Type | |
| Ischemia | Haemorrhage | Brainstem | Hemisphere | TIA | CVA |
| 11 | 4 | 3 | 12 | 3 | 12 |
| 5 | 2 | 1 | 6 | 2 | 5 |

For each patient of the three groups, a blood sample was collected at the time of admission in dry heparin-containing tubes. After centrifugation at 1500 g for 15 min at 4° C., plasma samples were aliquoted and stored at −20° C. until analysis. For the Stroke group, three additional blood samples were collected after the neurological event: <24 hours; <48 hours; and >48 hours. In this group, the time interval between the neurological event and the first blood draw was 185 minutes (ranging from 40 minutes to 3 days). This parameter was taken into account in the data analysis. Each patient or patient's relatives gave informed consent prior to enrollment.

FABP Measurement

H-FABP levels were measured in plasma by a sandwich ELISA. A 96-well polystyrene microtitre plate (NUNC, Polylabo, CH) was coated with 1 0011/well polyclonal goat anti human muscle FABP (Spectral Diagnosis HC, Ontario, USA), 20.4 µg/ml in carbonate buffer 0.1MpH 9.6, overnight at 4° C. The plate was automatically washed with PBS (15 mM $Na_2PO_4$-120 mM NaCl-2.7 mM KCl pH 7.4, Sigma) on a BioRad NOVAPATH™ WASHER (Hercules, Calif.). Every washing step was performed with fresh PBS. Non-specific binding sites were blocked with 200 µl/well 2% casein (w/v) in carbonate buffer for 2 h at 37° C. After the washing step, the samples were pipetted in duplicate at 100 µl/well. The plate was incubated 2 h at 37° C. After the washing step, 100 µl/well of mouse anti-human Heart FABP (clone 66E2, HyCult biotechnology b.v, Uden, Netherlands), 0.3 µg/ml in PBS-1% BSA (w/v), were incubated for 1 h at room temperature (R.T) with shaking. After the washing step, 100 µl/well of phosphatase labelled anti-mouse immunoglobulins (Dako, Denmark), 15 µg/ml in PBS, were incubated 1 h30 at R.T. with shaking. After the washing step, 50 µl/well of phosphatase substrate, 1.5 mg/ml paranitrophenylphosphate in diethanolamine, were incubated 30 min. Reaction was stopped with 100 µl/well NaOH 1M. Colour development was assessed with a microplate reader, Milenia™ kinetic analyzer (DPC, LA, USA), at a wavelength of 405 nm.

CK-MB and Troponin-I Measurement

Plasma samples were centrifuged at 1500 g for 15 min, and aliquots were stored at −20° C. Serum CK-MB and Troponin-I levels were determined using a fluorescent microparticle enzyme immunoassay (MEIA) with an automated chemical analyser AxSYM™ system (ABBOTT Laboratories, Abbott Park, Ill.). The formation rate of fluorescent products was directly proportional to the amount of Troponin-I in the sample. The detection limit for Troponin-I was 0.3 µg/l. CK-MB measurement is proportional to the amount of fluorescent probes and the detection limit was 0.7 µg/l.

NSE and S100 Measurement

Similar to H-FABP measurements, NSE and S100B were assayed in the four serial plasma samples of the Stroke group. The SMART S-100 and SMART-NSE ELISA kits were used. Both have been commercialised by Skye PharmaTech Inc. (Ontario, Calif.). The detection limits for NSE and S100B were 1 µg/l and 0.01 µg/l respectively.

Statistical Analysis

H-FABP levels were expressed in optical density (OD) values as mean ±SD. Because recombinant H-FABP was not available, external calibration could not be performed to express results as concentration units (ng/ml). Troponin-I and CK-MB levels, were expressed in ng/ml. Because plasma H-FABP, troponin-I and CK-MB concentrations did not fulfill the criteria for a gaussian distribution in neither of the normal, stroke and AMI populations according to the Kolmogorov-Smirnov test, comparisons between the three groups was carried out using the non-parametric Kruskall-Wallis test with post hoc Dunn's procedure. Comparisons between the stroke subgroups defined above were made by means of the Mann-Whitney U test and longitudinal assessment of H-FABP concentrations over time were analyzed using the repeated measures analysis of variance (ANOVA). Reference limits for H-FABP aiming at distinguishing stroke versus normal patients were delineated using receiver operating characteristic (ROC) curves (Analyse-It™ software for Microsoft Excel™) and, subsequently, sensitivity, specificity, positive and negative predictive values were calculated at each time point. Statistical significance was set at $p<0.05$.

Results

Individual results of the H-FABP assay in the three populations, expressed in OD units, are graphically shown in FIG. 1 and detailed in Table 3. Mean plasma H-FABP concentration was 0.221+0.134 OD in the Control group, 1.079±0.838 OD in the Stroke group and 2.340±0.763 OD in the AMI group. The coefficient of variation found for this ELISA was 5.8%±3.8. Using the Kruskall-Wallis test, all three concentrations were found significantly different (p<0.001) from each other. The best cut-off value to discriminate between the Control and the Stroke groups was set at OD>0.531 as determined by the ROC curves for H-FABP level (data not shown). Using this cut-off value, validity measures of H-FABP for the diagnosis of stroke were as follows: sensitivity was 68.2% with 15 out of 22 stroke patients above the cut-off, specificity was 100% with all of the 22 control subjects below the cut-off, positive predictive value was 100% and negative predictive value was 75.9%.

TABLE 3

| Group | | Control | AMI | Stroke |
|---|---|---|---|---|
| H-FABP | mean | 0.221 | 2.434 | 1.079 |
| | SD | 0.134 | 0.638 | 0.838 |
| | Significance | | <0.001 | <0.001 |
| Troponin-I | mean | 0.0 | 164.6 | 0.5 |
| | SD | 0.1 | 205.6 | 1.3 |
| | Significance | | <0.001 | ns |
| CK-MB | mean | 1.3 | 63.8 | 7.9 |
| | SD | 0.9 | 51.5 | 21.3 |
| | Significance | | <0.001 | ns |

To discriminate, at the biological level, between patients from the AMI and the Stroke groups, Troponin-I and CK-MB were further assayed in each group with cut-off values set at 2 ng/ml for the AxSYM Troponin-I assay and 3.8 ng/ml for the AxSYM CK-MB assay (Table 3). As expected, the concentrations of these AMI markers were significantly higher ($p<0.01$) in the AMI group as compared to both the Control and the Stroke groups. No difference was found between the last two groups, thus confirming that Troponin-I and CK-MB do not increase as a result of a brain insult and that stroke patients did not sustain a concomitant AMI at the time of their stroke. Taken together, H-FABP, Troponin-I and CK-MB concentrations allowed a correct discrimination between AMI (increase of all three markers) and stroke (increase of H-FABP with normal Troponin-I and CK-MB) in all the 20 AMI patients and in 15 stroke patients, with the exception of one stroke patient showing, along with increased H-FABP levels, moderately elevated levels of Troponin-I and CK-MB in the absence of EKG modifications, all of which being consistent with a concomitant non-AMI heart damage.

In the Stroke group, seven false negative results were found with H-FABP levels below the cut-off value of OD 0.531 at any time point following the neurological event. Of these seven patients, two had a rapid and complete recovery of their neurological deficits within 24 hours consistent with a transient ischemic attack (TIA), and two have had a lacunar stroke on MRI images, one located in the brainstem. While TIA and lacunar stroke may explain false negative results in a majority of patients, no explanation was consistently found for the three remaining stroke patients with low H-FABP levels.

Figure 2:
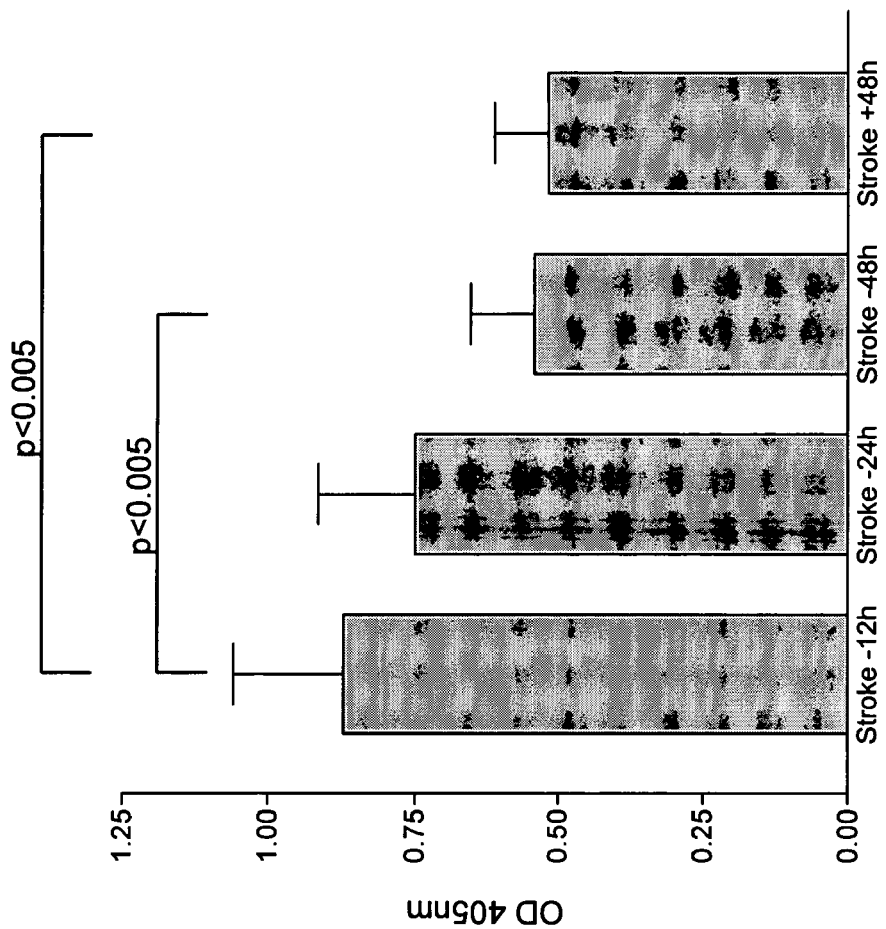
FIG. 2 shows the results of sequential determination of H-FABP levels (measured in OD units on the vertical axis) for the stroke group of patients at different time intervals after stroke.

Sequential determinations of H-FABP level after stroke showed that 10 out of 15 (67%) H-FABP positive stroke patients had a very early increase of H-FABP levels (<12 hours). Moreover, as shown in FIG. 2, when all stroke patients were considered, the mean H-FABP concentrations decreased steadily after the insult, the highest value being found before 12 hours. The differences between the initial measurement and the less than 48 hours and afterwards measurements were significant (ANOVA, $p<0.05$). When H-FABP levels were compared between the different subgroups of the Stroke group, no statistically significant differences were found. H-FABP levels were similar for ischemia ($0.955\pm0.668$, N=15) versus haemorrhage ($1.346\pm1.139$, N=7) strokes, and for hemispheric ($0.987\pm0.783$, N=18) versus brainstem ($1.493\pm1.080$) strokes, but the statistical power of the analyses was limited by the small size of the samples to be compared. However, when comparing established strokes versus TIAs, the former ($1.2002\pm0.892$) showed nearly twice as high H-FABP levels as the latter ($0.652\pm0.499$), although this difference failed to reach significance (Mann-Whitney U test, $p=0.24$).

Finally, NSE and S100B were assayed in the Control and the Stroke groups, and the results were compared with the H-FABP assay. The cut-off values using the SMART-NSE and SMART S100B protein ELISA tests for the diagnosis of stroke were 10 ng/ml for NSE and 0.02 ng/ml for S100B. NSE and S100B levels were slightly increased in the Stroke groups (14.12 ng/ml and 0.010 ng/ml, respectively) as compared to the Control group (15.88 ng/ml and 0.004 ng/ml, respectively). As shown on Table 4, specificity, sensitivity, PPV and NPV for the diagnosis of stroke were found much lower for NSE and S100B than for H-FABP. These differences are relevant since the three markers have been tested in the same samples.

TABLE 4

|  | H-FABP | NSE | S100B |
|---|---|---|---|
| Sensitivity | 68.2 | 55 | 15 |
| Specificity | 100 | 36.4 | 95.5 |
| Positive predictive | 100 | 44 | 75 |
| Negative predictive | 75.9 | 47.1 | 55.3 |

EXAMPLE 3

Three new proteins have been identified on 2-DE gels prepared with CSF samples from deceased patients. These proteins correspond to spots that have been previously shown increased in CSF samples from deceased patients relative to healthy controls. However, previous attempts to identify these proteins using MALDI-TOF mass spectrometry were unsuccessful. The current experiments were performed by μLC-MS-MS using ESI-Ion Trap device (DecaLCQ XP, ThermoFinnigan). Furthermore, the increasing amount of data in databases could lead to the successful identification of previously uncharacterized spots.

Figure 3:
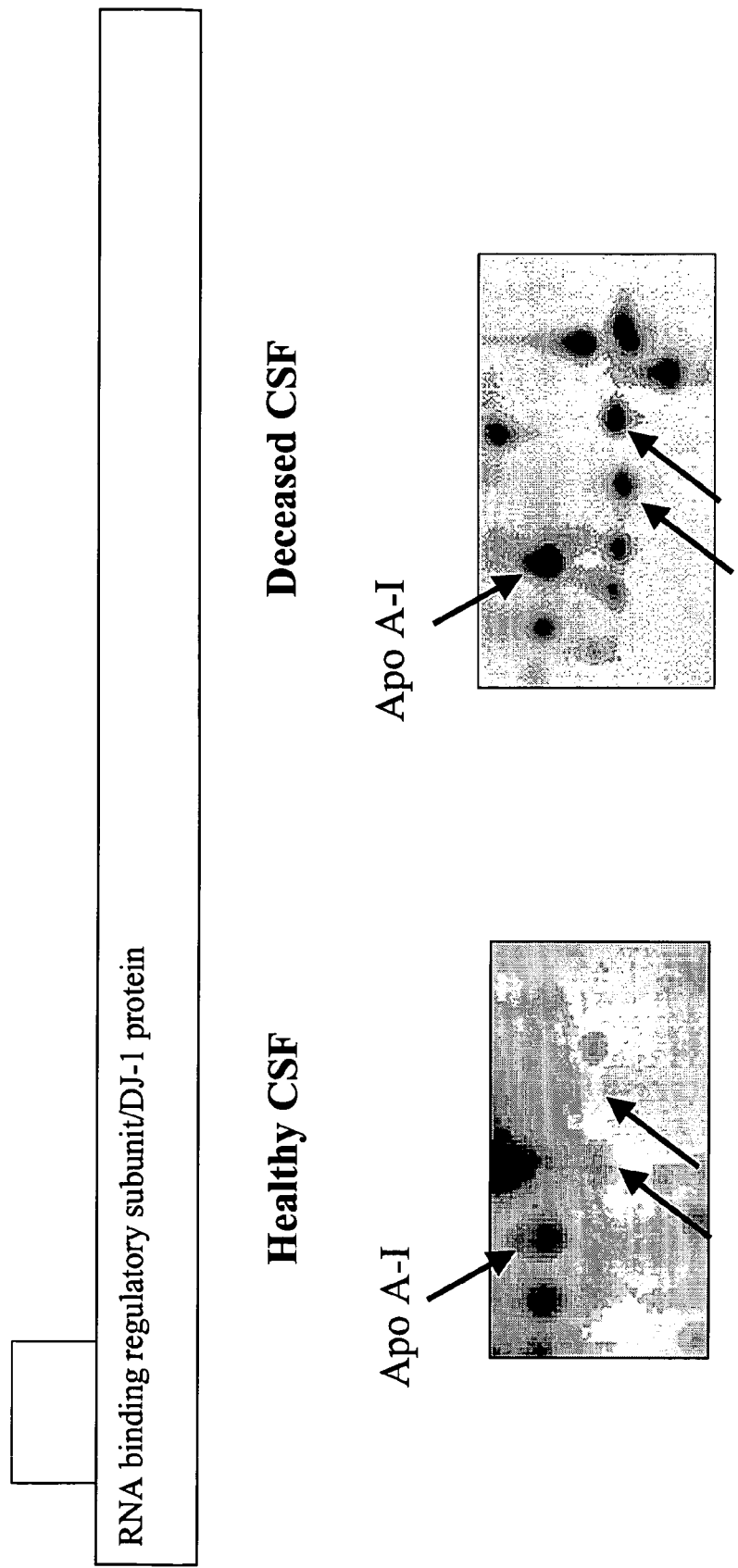
FIG. 3 shows portions of 2-DE maps for healthy and post-mortem CSF, with upward-directed arrows indicating spots corresponding to RNA binding regulatory subunit or DJ-1 protein. Enlargements of healthy CSF and deceased CSF 2-DE maps are shown. Forty five µg of protein was loaded on a IPG gel (pH 3.5-10 NL, 18 cm). Second dimension was a vertical gradient slab gel (9-16% T). Gel was silver stained. The spots corresponding to the RNA binding regulatory subunit or to the DJ-1 protein are indicated by upward-directed (red) arrows.

(1) RNA-binding protein regulatory subunit (O14805)/DJ-1 protein (Q99497): RNA-binding protein regulatory subunit has been previously described in deceased CSF samples (see Example 1 above). Here, we have obtained the same identification with an adjacent spot (FIG. 3). We also confirmed the previous identifications. FIG. 1 shows enlargements of healthy CSF and deceased CSF 2-DE maps. 270 μg of protein was loaded on a IPG gel (pH 3.5-10NL, 18 cm). The second dimension was a vertical slab gel (12% T). The gel was stained with a fluorescent dye. The upward-pointing arrows indicate the spots corresponding to the RNA binding regulatory subunit or to the DJ-1 protein.

Furthermore, our results indicate that these spots could correspond to another homologous protein called DJ-1. The RNA-binding protein regulatory subunit and DJ-1 sequences differ from one another only by one amino acid. The single peptide detected during the current experiments did not contain this specific residue.

DJ-1 gene mutations are associated with autosomal recessive early-onset parkinsonism (Bonifati et al., Science, 2003). Different results suggest that the DJ-1 protein could be involved in cellular oxidative stress response and neurodegenerative pathologies (Bonifati et al., Science, 2003; Wilson et al., PNAS, 2003).

Figure 4:
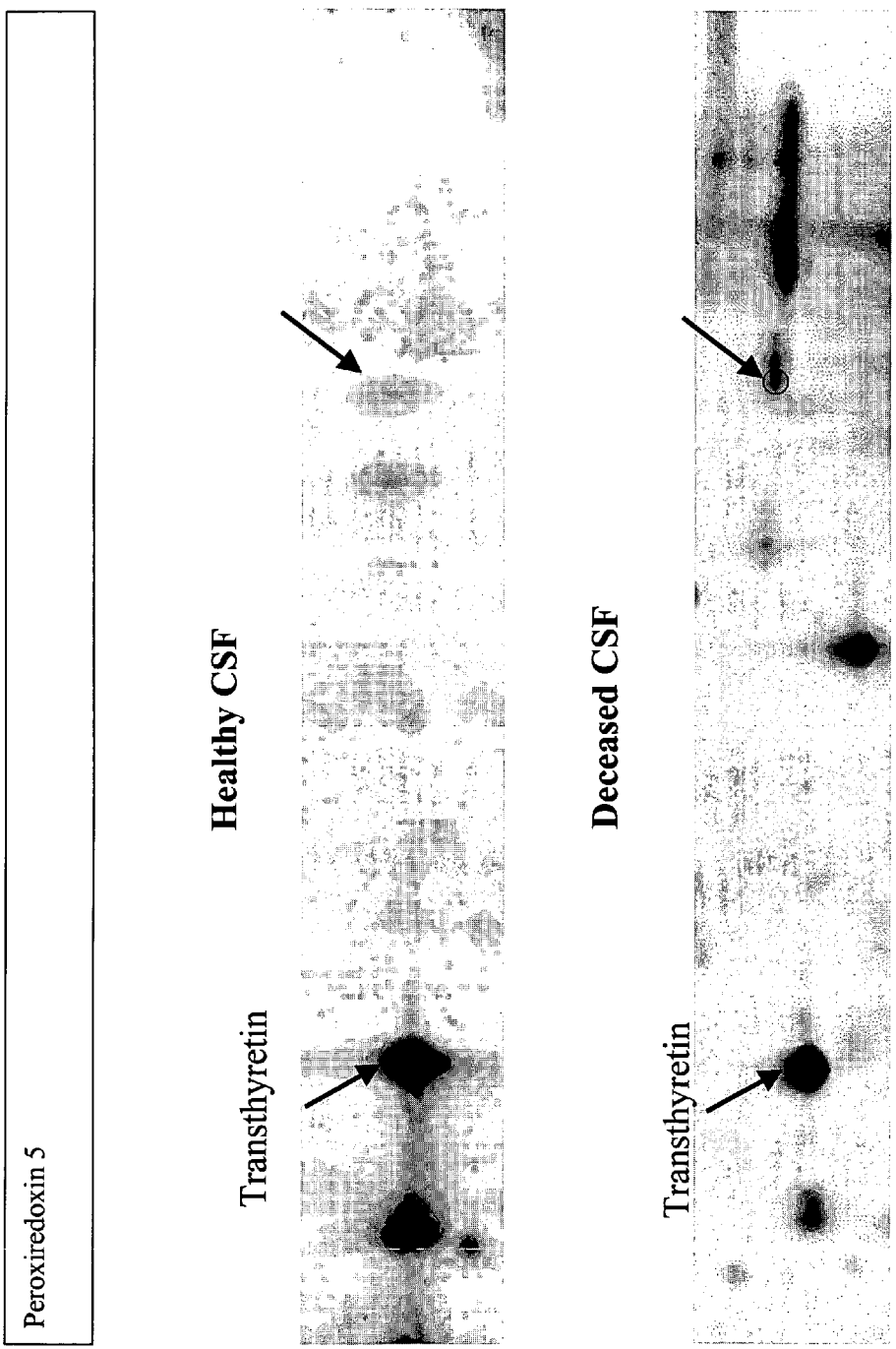
FIG. 4 shows portions of 2-DE maps for healthy and post-mortem CSF, with the right-hand arrows indicating spots corresponding to peroxiredoxin 5. Enlargements of healthy CSF and deceased CSF 2-DE maps are shown. Forty five µg of protein was loaded on a IPG gel (pH 3.5-10 NL, 18 cm). Second dimension was a vertical gradient slab gel (9-16% T). Gel was silver stained. The spot corresponding to Peroxiredoxin 5 is indicated by the right-hand (red) arrows.

(2) Peroxiredoxin 5 (P30044):

The 2-DE spot corresponding to Peroxiredoxin 5 is shown in FIG. 4. This is an enlargement of healthy CSF and deceased CSF 2-DE maps prepared in the same way as for FIG. 3. The spot corresponding to Peroxiredoxin 5 is shown by the arrows on the right-hand side.

Peroxiredoxin 5 is an antioxidant enzyme that could have a neuroprotective effect (Plaisant et al., Free Radic. Biol. Med., 2003). Aberrant expression pattern of proteins belonging to the Peroxiredoxin family was also described in brains of patients with different neurodegenerative diseases (Krapfenbauer et al., Electrophoresis, 2002; Krapfenbauer et al., Brain Res., 2003).

Figure 5:
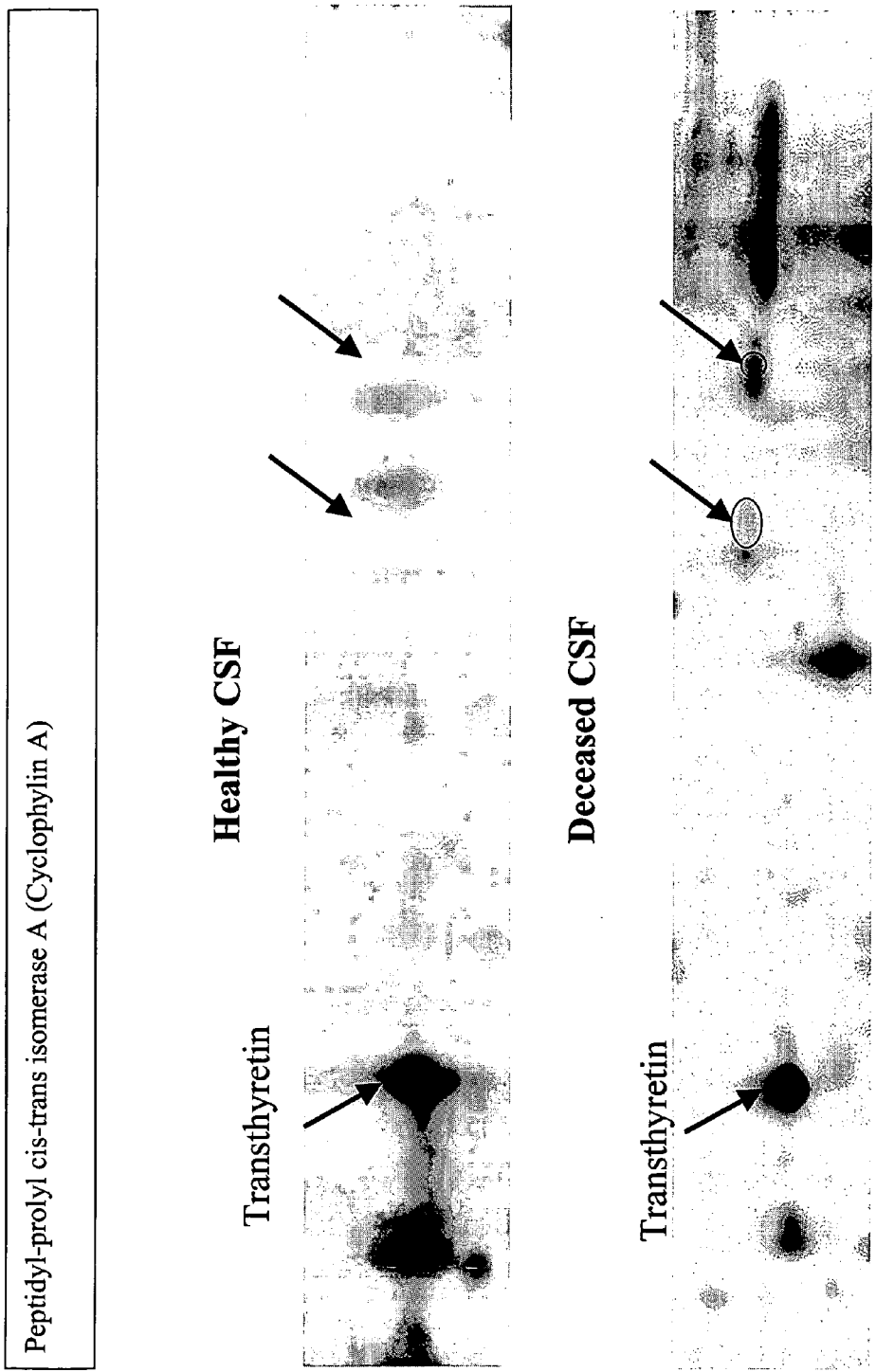
FIG. 5 shows portions of 2-DE maps for healthy and post-mortem CSF, with the right-hand pair of arrows indicating spots corresponding to peptidyl-prolyl cis-trans isomerase A (cyclophylin A). Enlargements of healthy CSF and deceased CSF 2-DE maps are shown. Forty five µg of protein was loaded on a IPG gel (pH 3.5-10 NL, 18 cm). Second dimension was a vertical gradient slab gel (9-16% T). Gel was silver stained. The spots corresponding to Cyclophylin A are indicated by the right-hand pair of (red) arrows.

(3) Peptidyl-prolyl cis-trans isomerase A or Cyclophilin A (P05092) Two spots were identified as being the Peptidyl-prolyl cis-trans isomerase A (FIG. 5). This is an enlargement of healthy CSF and deceased CSF 2-DE maps prepared in the same way as for FIG. 4. The basic spot corresponding to Cyclophilin A is just adjacent to the spot corresponding to the Peroxiredoxin 5.

Cyclophilin A was described as a protective factor against cellular oxidative stress (Doyle et al., Biochem J., 1999). It binds to Peroxiredoxin enzymes and could be involved in the peroxidase activity (Lee et al., J. Biol. Chem., 2001). Furthermore, a publication suggests that Cyclophilin A is secreted by vascular smooth muscle cells (VSMC) in response to oxidative stress and stimulate VSMC growth (Jin et al., Circ. Res., 2000). These results suggest the implication of Cyclophilin A in vascular diseases processes. A link was also described with a familial form of amyotrophic lateral sclerosis (a neurodegenerative pathology) associated with a mutation in the antioxidant enzyme Cu/Zn Superoxide Dismutase-1 (Lee at al., PNAS, 1999). Cyclophilin A seems to have a protective effect against the mutant SOD-induced apoptosis.

EXAMPLE 4

Introduction

A survey of stroke patients was carried out and the results are shown in FIGS. 6 to 15. An ELISA intensity signal was obtained for Ubiquitin fusion degradation protein 1 homolog (UFD1), RNA binding regulatory subunit (RNA-BP) and nucleotide diphosphate kinase A (NDK A) in plasma samples of the patients and of negative control patients. Plasma samples were taken from patients between 0-24 hours and/or after 72 hours of arrival at emergency hospital, and were matched for age/sex with samples from control patients.

Protocol

ELISA was performed using 96-well Reacti-Bind™ NeutrAvidin™ coated Black Plates (Pierce, Rockford, Ill.). Plates were first rinsed in Borate Buffer Saline pH 8.4 (BBS) (100 mM $H_3BO_3$, 25 mM $Na_2B_4O_7$ (Sigma, St Louis, Mo., USA), 75 mM NaCl (Merck, Darmastadt, Germany)) on a NOVAP-ATH washer (Bio-Rad, Hercules, Calif.). Then, 50 μl of antibody-biotin conjugated (2 μg/mL) prepared in the dilution buffer A at pH 7 (DB, Polyvinyl Alcohol, 80% hydrolyzed, Mol. Wt. 9000-10,000 (Aldrich, Milwaukee, Wis., USA), MOPS (3-[N-Morpholino] propane sulfonic acid) (Sigma), NaCl, $MgCl_2$ (Sigma), $ZnCl_2$ (Aldrich), pH6.90, BSA 30% Solution, Manufacturing Grade (Serological Proteins Inc., Kankakee, Ill.)), were added and incubated for one hour at 37° C. Plates were then washed 3 times in BBS in the plate washer. 50 μl of antigen was then added and incubated for one hour at 37° C. Recombinant proteins were diluted at 100, 50, 25, 12.5, 6.25 ng/ml in the dilution buffer A to establish a calibration curve. Plasma samples were diluted at the appropriate dilution in the dilution buffer A. After the washing step, 50 μl of alkaline phosphatase conjugated antibodies were added at the appropriate dilution in the dilution buffer A and incubated for one hour at 37° C. The 96-well plate was then washed 3 times with BBS in the plate washer and 50 μL of fluorescence Attophos® AP Fluorescent substrate (Promega, Madison, Wis.) were added. Plates were read immediately on a SpectraMax GEMINI-XS, (Molecular Devices Corporation, Sunnyvale, Calif., U.S.A.) fluorometer microtiter plate reader relative fluorescence units (RFU) ($\lambda_{excitation}$=444 nm and $\lambda_{emission}$=555 nm).

We read plates in fluorescence using a SpectraMax GEMINI-XS (Molecular Devices) fluorometer microplate reader ($\lambda_{excitation}$=444 nm and $\lambda_{emission}$=555 nm). Results are expressed in RFU and can be obtained in endpoint mode (only one reading) or in kinetic mode on 10 minutes. In kinetic mode, for each well we used 6 flashes (per well) which are integrated into an average and read each well 6 times using minimal interval time between each reading. This ends up being 2 minutes between readings. We determined a slope and this is what we used for our valuations. The best cut-off value to discriminate between the Control and the Stroke (Ischemic plus hemorrhagic or Ischemic vs. Hemorrhagic) groups was determined by the ROC curves using GraphPad Prism 4 software.

Conclusion

We can clearly see from FIGS. 7, 10 and 13 that UFD1, RNA-BP and NDK A respectively are overexpressed in stroke patients compared to control patients. Statistical analysis for each of the biomarker was performed and ROC curves (GraphPad Prism 4 software) indicating sensitivity of the test as a function of 1-specificity (FIGS. 8, 11 and 14 for UFD1, RNA-BP and NDK A respectively) were drawn. Best cutoff values to distinguish between stroke and control patients were deduced from these ROC curves. We obtained 94.4%, 94.4% and 100% sensitivity for UFD1, RNA-BP and NDK A respectively and 77.8%, 72.2% and 83.3% specificity for UFD1, RNA-BP and NDK A respectively. For each marker, a non parametric Mann Whitney test was performed to compare stroke and control groups. For the 3 biomarkers, we obtained very low p values (<0.0001 for UFD1 and NDK A and p=0.0003 for RNA-BP) meaning that differences between stroke and controls are very significant.

In FIG. 6, we can also notice that RNA-BP and NDK A can detect a stroke only 30 minutes after symptoms onset, meaning that these are very early markers of stroke. This result is confirmed by the decreasing signal observed between arrival at the hospital and after 72 hours. Patients 202 and 239 were tested at the arrival (between 0 and 24 hours) and after 72 hours and we can see that for all the markers, the signal significantly decreases.

These results demonstrate that Ubiquitin fusion degradation protein 1 homolog (UFD1), RNA binding regulatory subunit (RNA-BP) and nucleotide diphosphate kinase A (NDK A) are useful markers for early diagnosis of stroke, alone, in combination, or combined with other biomarkers.

EXAMPLE 5

This Example is concerned with post-translational modifications that can be induced in neurodegenerative disorders. The study population and samples handling, and the CSF 2-DE were as described in Example 1.

2-DE immunoblotting Assays

Proteins separated by 2-DE were electroblotted onto PVDF membranes essentially as described by Towbin et al. [22]. Membranes were stained with Amido Black, destained with water and dried. Proteins of interest were detected as previously described [29] using specific antibodies and ECL™ western blotting detection reagents (Amersham Biosciences, Uppsala, Sweden). We used the following antibody: anti-human Prostaglandin D synthase (lipocalin type) rabbit polyclonal antibody (Cayman chemical, Ann Arbor, Mich.) diluted 1/250.

Figure 16:
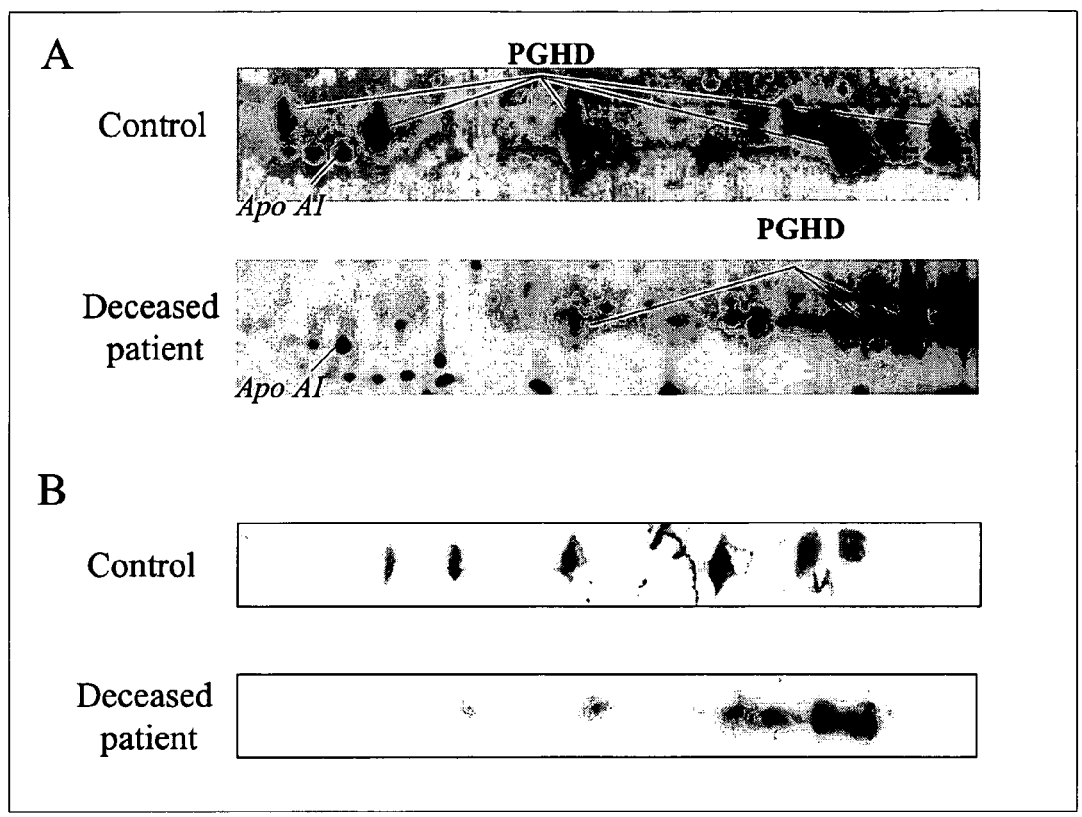
FIG. 16 shows portions of 2-DE maps for healthy and post-mortem CSF indicating prostaglandin D synthase levels.

FIG. 16(A) shows a comparison of PGHD spot intensities on 2-DE gels prepared with CSF of deceased or control patients. Forty-five μg of protein was loaded on an IPG strip (pH 3.5-10 NL, 18 cm). The second dimension was performed on a vertical gradient slab gel (9-16% T), stained with ammoniacal silver. Apolipoprotein AI labelled in italic showed similar levels in the two samples. PGHD spot locations in control gel were deduced from previous identifications [31]. In the gel from deceased patients, putative PGHD spot locations are given. FIG. 16(B) shows immunodetection of PGHD in 2-DE gels prepared with CSF from deceased and control patients. 2-DE was performed as indicated in A. Immunodetection was performed as previously described [29] using an anti-human Prostaglandin D synthase (lipocalin type) rabbit polyclonal antibody and ECL™ western blotting detection reagents.

Results

Prostaglandin D synthase (PGHD) is a basic protein (pI=8.37) known to be post-translationaly modified by N-glycosylation (Hoffmann A. et al., *J. Neurochem.* 1994, 63, 2185-2196). On CSF 2-D gels from healthy living patients, five spots were detected. On 2-D gels prepared with post-mortem CSF, the three acidic spots are strongly decreased with a concomitant increase of the two basic spots (FIG. 16A).

In order to confirm that these different spots correspond to PGHD, we performed immunoblot assays using a specific antibody (FIG. 16B). The results obtained confirmed that the acidic PGHD spots were not present in the CSF from deceased patients while the basic spots were still present. Furthermore, the measurement of the total PGHD spot volume in the two gels using the Melanie 3 software indicated that the PGHD level is similar in the two samples. This suggests, therefore, that there was a deglycosylation of PGHD in the CSF of deceased patients but the total PGHD amount remained constant.

Data From the Literature:

PGHD was found to be decreased in the CSF of patients suffering from AD (Puchades M. et al., *Brain Res. Mol. Brain Res.* 2003, 118, 140-146). However, the study was performed using 2-DE gels and only the acidic spots were analyzed. As shown by our results on CSF from deceased patients, it is possible that PGHD was deglycosylated in the samples analyzed, resulting in the disappearance of acidic spots but no decrease in the total protein level.

Using capillary isoelectric focusing, Hiraoka and colleagues have identified changes in the charge microheterogeneity of CSF PGHD associated with various neurological disorders (Hiraoka A. et al., *Electrophoresis* 2001, 22, 3433-3437). The ratio of basic forms/acidic forms was found to increase in AD, in PD with pathological brain atrophy, and in multiple sclerosis. It was speculated that these post-translational modifications were linked to changes in the N-glycosylation pattern.

PGHD Post-Translational Modifications (PTM) Pattern in CSF of a Creutzfeldt-Jakob (CJD) Disease Patient:

We compared the PTM pattern of PGHD in CSF samples collected from a CJD patient and a healthy control. The proteins were separated by 2-DE, electroblotted on a PVDF membrane and PGHD was detected using a specific antibody, as previously described. The CSF samples were collected by lumbar puncture. The control patient had a neurological workup for benign conditions unrelated to brain damage. CSF samples were centrifuged immediately after collection, aliquoted, frozen at −20° C. and stored until analysis.

Figure 17:
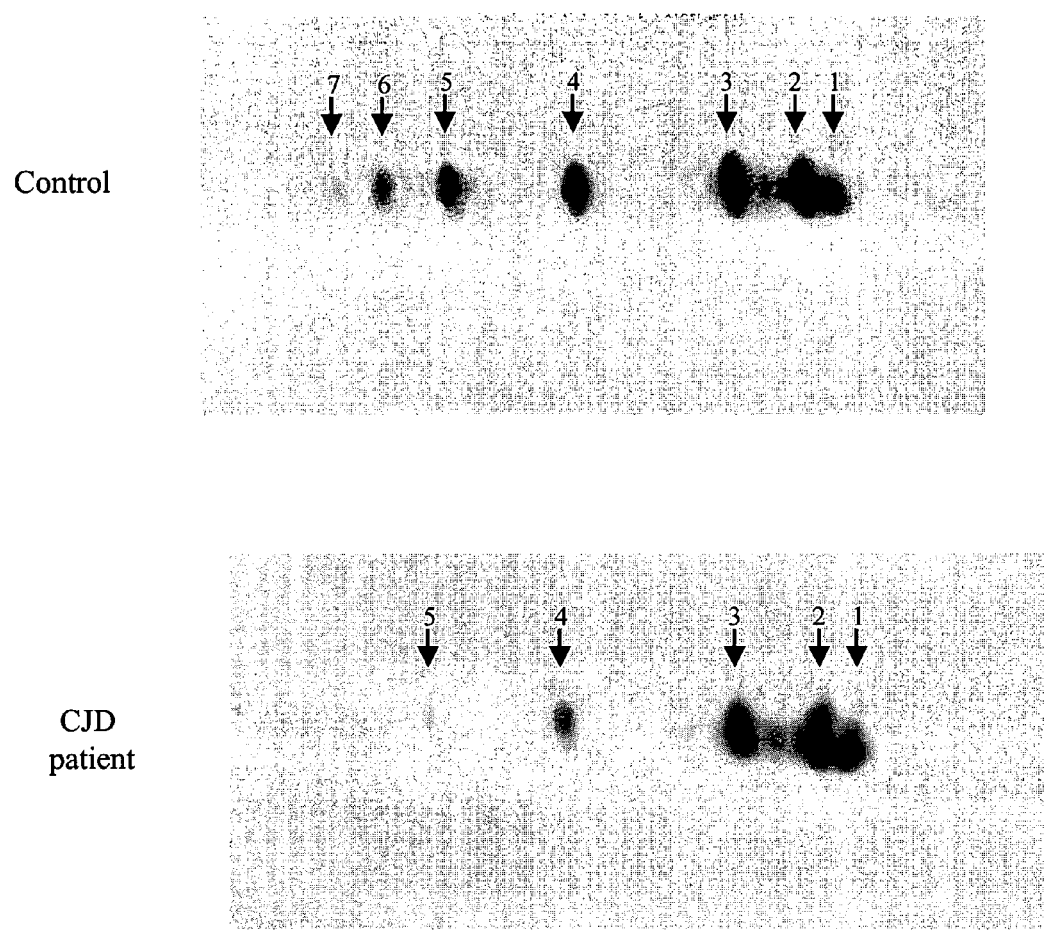
FIG. 17 shows prostaglandin D2 synthase spot intensities on mini-2-DE gels prepared with CSF of a CJD patient and a healthy patient as a control.

The results are shown in FIG. 17 which is a comparison of prostaglandin D2 synthase spot intensities on mini-2-DE gels prepared either with CSF of a patient suffering from the Creutzfeldt-Jakob disease or with a control CSF from a healthy patient. Forty-five µg of protein were loaded on a IPG gel (pH 3-10 NL, 7 cm). Second dimension was a vertical gradient slab gel (12% T). Immunodetection was performed using an anti-human PGHD (lipocalin type) rabbit polyclonal antibody (Cayman chemical, Ann Arbor, Mich.) and ECL™ western blotting detection reagents (Amersham Biosciences, Uppsala, Sweden).

The results showed that the PTM pattern of PGHD in the CSF from the CJD patient is clearly different from the control, with a strong decrease of the 4 most acidic spots (FIG. 17). The pattern of the CJD patient is similar to the one observed in post-mortem CSF. These data support the interest of changes in the PTM pattern of PGHD as marker of neurological disorders.

EXAMPLE 6

This Example provides additional data showing plasma levels of UFDP1 in stroke and control patients. FIG. 19 shows the levels of UFDP1 in CSF of a control and a deceased patient. Additional data has been obtained from two cohorts of patients and controls, the smaller from Geneva, and a more comprehensive panel from the US. The methodology for this Example and following Examples 7 and 8 is the same, save that the antibodies being used have different specificities for the protein in question. The method in each of the studies is similar to that given as Example 4:

ELISA was performed using 96-well Reacti-Bind™ NeutrAvidin™ coated Black Plates (Pierce, Rockford, Ill.). Plates were first rinsed in Borate Buffer Saline pH 8.4 (BBS) (100 mM H3BO3, 25 mM Na2B4O7 (Sigma, St Louis, Mo., USA), 75 mM NaCl (Merck, Darmstadt, Germany)) on a NOVAPATH™ washer (Bio-Rad, Hercules, Calif.). Then, 50 µl of relevant biomarker specific antibody-biotin conjugate (2 µg/mL) prepared in the dilution buffer A at pH 7 (DB, Polyvinyl Alcohol, 80% hydrolyzed, Mol. Wt. 9000-10,000 (Aldrich, Milwaukee, Wis., USA), MOPS (3-[N-Morpholino] propane sulfonic acid) (Sigma), NaCl, MgCl2 (Sigma), ZnCl2 (Aldrich), pH6.90, BSA 30% Solution, Manufacturing Grade (Serological Proteins Inc., Kankakee, Ill.), were added and incubated for one hour at 37° C. Plates were then washed 3 times in BBS in the plate washer. 50 µl of antigen or plasma was then added and incubated for one hour at 37° C. Recombinant protein antigens were diluted at 100, 50, 25, 12.5, 6.25, 3.125, 1.56 ng/ml in the dilution buffer A to establish a calibration curve. Plasma samples were diluted at the appropriate dilution in the dilution buffer A. After a further washing step, 50 µl of relevant biomarker specific alkaline phosphatase conjugated antibodies were added at the appropriate dilution in the dilution buffer A and incubated for one hour at 37° C. The 96-well plate was then washed 3 times with BBS in the plate washer and 50 µl of fluorescence Attophos® AP Fluorescent substrate (Promega, Madison, Wis.) were added. Plates were read immediately on a SpectraMax GEMINI-XS, (Molecular Devices Corporation, Sunnyvale, Calif., U.S.A.) fluorometer microtiter plate reader We read plates in fluorescence using a SpectraMax GEMINI-XS (Molecular Devices) fluorometer microplate reader ($\lambda_{excitation}$=444 nm and $\lambda_{emission}$=555 nm). Results are expressed in RFU and can be obtained in endpoint mode (only one reading) or in kinetic mode on 10 minutes. In kinetic mode, for each well we used 6 flashes (per well) which are integrated into an average and read each well 6 times using minimal interval time between each reading. This ends up being 2 minutes between readings. We determined a slope and this is what we used for our valuations. The best cut-off value to discriminate between the Control and the Stroke groups was determined by the ROC curves using GraphPad Prism 4 software.

The results are shown in FIG. 20.

EXAMPLE 7

This corresponds to Example 6, except that the polypeptide is RNA-BP. FIG. 21 shows the levels of RNA-BP in CSF of a control and a deceased patient. FIG. 22 shows RNA-BP plasma concentration by ELISA for three studies, each comprising stroke patients and controls.

EXAMPLE 8

This corresponds to Example 6, except that the polypeptide is NDKA. FIG. 23 shows the levels of NDKA in CSF of a control and a deceased patient. FIG. 24 shows NDKA plasma concentration by ELISA for the Geneva and US cohorts of stroke patients and controls as in Example 6.

EXAMPLE 9

In addition to simple discrimination between stroke and control patients, the data from each of Examples 6, 7 and 8 can be analysed in relation to the time between cerebrovascular accident and sample collection, or alternatively in relation to the type of stroke—ischaemic, haemorrhagic or transient ischaemic attack (TIA). These separate analyses are shown in FIG. 25a and FIG. 25b and demonstrate the utility of deceased CSF markers in the diagnosis of stroke. This is particularly relevant to clinical practice as it is essential to diagnose stroke within three hours of the event to allow administration of clot busting drugs such as TPA. It is also essential that tests can differentiate haemorrhagic stroke from ischaemic attack as TPA is only suitable for the treatment of ischaemia and can have catastrophic effects in patients with an haemorrhagic stroke.

EXAMPLE 10

Whilst each of the deceased CSF markers have good individual performance for the diagnosis of stroke, it is likely that a commercial product will require the measurement of levels of several proteins. This 'panel' approach can be achieved in two ways. In the simpler approach the antibodies for each separate marker are pooled and used to coat microtitre wells. The intensity of the signal will be the sum of that for each independent marker, though in this case it will be impossible to determine the individual levels of each of the markers. This may create challenges in setting meaningful cut-off values, however, this presents the most user friendly commercial product.

FIG. 26 summarises the markers which are used in this Example. Experimental results are shown in FIG. 27, in which antibodies against the deceased CSF proteins UFD1, RNA-BP, NDKA and H-FABP were used at the same concentrations as in Example 4. However, these antibody solutions were mixed in equal volumes, reducing the concentration of each antibody species to one quarter of the original level in the single analyte examples described above. The protocol used is as follows:

To overcome the problem of panel algorithm, we tested the four antibodies directly in mixture in each well. The protocol is exactly the same as previously described for separated antibodies (above), save that each of the biomarker specific biotin-antibody conjugates were used at 12.5 µL per well during the first antibody coating step. The standard curve was similarly constructed by using 12.5 µL per well of each of the four recombinant protein antigens UFDP1, RNA-BP, NDKA and H-FABP each prepared separately at initial concentrations of 100, 50, 25, 12.5, 6.25, 3.125, 1.56 ng/ml in the dilution buffer A to establish a calibration curve on the same plate. Plasma samples were used at the same dilution and volume (50 µL per well) as for the individual biomarker assays. Detection of captured antigens was performed using the same biomarker specific antibody-alkaline phosphatases conjugates as the individual assays, with equal volumes (12.5 µL) of the four biomarker specific antibody-alkaline phosphatases conjugates being added to each well for the standard curve and plasma samples. Measurement of fluorescence was performed as described for the single biomarker assays as described in the example above.

Ten stroke and ten control (non age/sex matched) plasma samples 2-fold diluted were tested (FIG. 27). This experiment led to 100% sensitivity and 80% specificity. The two false positives samples correspond to patient's control 368 and 450 that display prostate cancer and probable head trauma.

In this specific example the fluorescence signal obtained corresponds to the sum of the signal generated by each biomarker specific antibody sandwich and it is impossible to determine the relative contribution of each single biomarker to the whole when using alkaline-phosphatase conjugated antibodies for the detection side of the assay. It is also an aspect of the invention that each biomarker specific antibody can be labelled with a different fluorophore with sufficient difference between their excitation and emission wavelengths that the level of each antibody can be determined without interference. In this case it is possible to accurately quantify the levels of up to four different biomarkers in a sample in a single assay, providing benefits in reduced sample requirement and increased throughput.

EXAMPLE 11

In some circumstances it may not be desirable to measure levels of multiple analytes in a single well. For example the absolute levels of individual proteins, or the ratio between levels of multiple proteins may be necessary to make a specific diagnosis. In this situation it may be desirable to measure the levels of each analyte in a separate assay. A predictive algorithm is then used to interpret these multiparametric datasets to provide a unique diagnosis for each patient. In this Example we have used a statistical algorithm to predict the theoretical performance of different multi-analyte biomarker panels.

The datasets of individual biomarker levels generated in the various examples above were analysed using a proprietary algorithm to determine the true positive and true negative rates for each combination of the deceased CSF proteins UFDP1, RNA-BP, NDKA and H-FABP for the diagnosis of stroke. For the analysis a Sample set (18 controls and 18 stroke for UFD1, RNA-BP, NDK A and H-FABP) was divided into 2 random populations.

80% of the total samples for training of the thresholds was performed by the technique of naive bayes, and the remaining 20% of the total samples were then used to evaluate the thresholds (sensitivity and specificity) for each marker, or combination of markers made 1000 fold.

Where the algorithm was applied to single proteins it was possible to compare sensitivities and specificities values with those observed. The sensitivity and specificity for these data sets (figures in parentheses) were calculated based on the optimum cut-off determined from the ROC curve as described in the examples above. In the following data, the first value in parenthesis corresponds to standard deviation (e.g., 0.93±0.15). The second value in parenthesis for the "1 protein" data corresponds to sensitivity (SE) and specificity (SP) obtained without using the algorithm, but using simple ROC curve (GraphPad Prism). The SE and SP values are indicated just to compare the results with and without the algorithm.

The output of this algorithm analysis was as follows:

1 Protein

True positive rate of UFD1 on training set: 0.93 (0.15) (SE 94%)

True negative rate of UFD1 on training set: 0.74 (0.24) (SP 78%)

True positive rate of RNA-BP on training set: 0.85 (0.21) (SE 94%)

True negative rate of RNA-BP on training set: 0.73 (0.23) (SP 72%)

True positive rate of H-FABP on training set: 0.47 (0.29) (SE 39%)

True negative rate of H-FABP on training set: 0.80 (0.23) (SP 100%)

True positive rate of NDK A on training set: 0.79 (0.24) (SE 100%)

True negative rate of NDK A on training set: 0.89 (0.16) (SP 83%)

2 Proteins

True positive rate of UFD1/RNA-BP on training set: 0.90 (0.17)

True negative rate of UFD1/RNA-BP on training set: 0.69 (0.25)

True positive rate of UFD1/H-FABP on training set: 0.82 (0.22)

True negative rate of UFD1/H-FABP on training set: 0.83 (0.20)

True positive rate of UFD1/NDK A on training set: 0.92 (0.16)

True negative rate of UFD1/NDK A on training set: 0.79 (0.21)

True positive rate of RNA-BP/H-FABP on training set: 0.81 (0.24)

True negative rate of RNA-BP/H-FABP on training set: 0.73 (0.24)

True positive rate of RNA-BP/NDK A on training set: 0.91 (0.16)

True negative rate of RNA-BP/NDK A on training set: 0.83 (0.21)

True positive rate of H-FABP/NDK A on training set: 0.77 (0.27)

True negative rate of H-FABP/NDK A on training set: 0.84 (0.20)

3 Proteins

True positive rate of RNA-BP/NDK A/H-FABP on training set: 0.96 (0.11)

True negative rate of RNA-BP/NDK A/H-FABP on training set: 0.83 (0.20)

True positive rate of UFD1/NDK A/H-FABP on training set: 0.92 (0.17)

True negative rate of UFD1/NDK A/H-FABP on training set: 0.83 (0.21)

True positive rate of UFD1/RNA-BP/NDKA on training set: 0.95 (0.14)

True negative rate of UFD1/RNA-BP/NDKA on training set: 0.82 (0.20)

True positive rate of UFD1/RNA-BP/H-FABP on training set: 0.93 (0.15)

True negative rate of LFD1/RNA-BP/HFABP on training set: 0.75 (0.23)

The 4 Proteins

True positive rate of UFD1/RNA-BP/H-FABP/NDK A on training set: 0.93 (0.13)

True negative rate of UFD1/RNA-BP/H-FABP/NDK A on training set: 0.73 (0.23)

FIG. 28 is a graphical representation of combinations of two out of the four biomarkers used in this Example. It shows the cut-off points (horizontal and vertical lines) which we have determined for diagnosis.

EXAMPLE 12

Further large scale studies were performed in Geneva and USA on UFD1, RNA-BP and NDK A post mortem CSF markers. ELISA was carried out on samples as described in the previous Examples (both for the Geneva as well as the USA experiments). The results are shown in FIGS. 29-38.

REFERENCES

[1] Vaagenes P, Urdal P, Melvoll R, Valnes K: Enzyme level changes in the cerebrospinal fluid of patients with acute stroke. Arch Neurol 1986;43:357-362.

[2] Lampl Y, Paniri Y, Eshel Y, Sarova-Pinhas I: Cerebrospinal fluid lactate dehydrogenase levels in early stroke and transient ischemic attacks. Stroke 1990;21:854-857.

[3] Matias-Guiu J, Martinez-Vazquez J, Ruibal A, Colomer R, Boada M, Codina A: Myelin basic protein and creatine kinase BB isoenzyme as CSF markers of intracranial tumors and stroke. ActaNeurol Scand 1986;73:461-465.

[4] Persson L, Hardemark H G, Gustafsson J, Rundstrom G, Mendel-Hartvig I, Esscher T, Pahlman S: S-100 protein and neuron-specific enolase in cerebrospinal fluid and serum: markers of cell damage in human central nervous system. Stroke 1987;18:911-918.

[5] Cunningham R T, Young I S, Winder J, O'Kane M J, McKinstry S, Johnston C F, Dolan O M, Hawkins S A, Buchanan K D: Serum neurone specific enolase (NSE) levels as an indicator of neuronal damage in patients with cerebral infarction. Eur J Clin Invest 1991;21:497-500.

[6] Herrmann M, Vos P, Wunderlich M T, de Bruijn C H, Lamers K J: Release of glial tissue-specific proteins after acute stroke: A comparative analysis of serum concentrations of protein S-100B and glial fibrillary acidic protein. Stroke 2000;31:2670-2677.

[7] Bitsch A, Horn C, Kemmling Y, Seipelt M, Hellenbrand U, Stiefel M, Ciesielczyk B, Cepek L, Bahn E, Ratzka P, Prange H, Otto M: Serum tau protein level as a marker of axonal damage in acute ischemic stroke. Eur Neurol 2002; 47:45-51.

[8] Watson M A Scott M G: Clinical utility of biochemical analysis of cerebrospinal fluid. Clin Chem 1995;41:343-360.

[9] Hochstrasser D F, Frutiger S, Paquet N, Bairoch A, Ravier F, Pasquali C, Sanchez J C, Tissot J D, Bjellqvist B, Vargas R, et al.: Human liver protein map: a reference database established by microsequencing and gel comparison. Electrophoresis 1992;13:992-1001.

[10] Sanchez J-C, Chiappe D, Converset V, Hoogland C, Binz P-A, Paesano S, Appel R D, Wang S, Sennitt M, Nolan A, Cawthorne M A, Hochstrasser D F: The mouse SWISS-2D PAGE database: a tool for proteomics study of diabetes and obesity. Proteomics 2001;1:136-163.

[11] Hochstrasser DF Merril C R: 'Catalysts' for polyacrylamide gel polymerization and detection of proteins by silver staining. Appl Theor Electrophor 1988;1:35-40.

[12] Appel R D, Palagi P M, Walther D, Vargas J R, Sanchez J C, Ravier F, Pasquali C, Hochstrasser D F: Melanie II—a third-generation software package for analysis of two-dimensional electrophoresis images: I. Features and user interface. Electrophoresis 1997; 18:2724-2734.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

The invention claimed is:

1. A method of diagnosis of a brain damage-related disorder in a subject suspected of having a brain damage-related disorder, which comprises:
   detecting levels of two or more polypeptides comprising H-FABP and Glutathione S transferase P in a sample of body fluid taken from the subject suspected of having a brain damage-related disorder, wherein the body fluid is selected from the group consisting of cerebrospinal fluid, plasma, serum, and blood;
   detecting levels of the same two or more polypeptides comprising H-FABP and Glutathione S transferase P in a comparative sample of body fluid taken from a subject known not to have a brain damage-related disorder, wherein the body fluid is the same type of body fluid as the sample from the subject suspected of having a brain damage-related disorder;
   comparing the levels of the two or more polypeptides in the sample of body fluid taken from the subject suspected of having a brain damage-related disorder with the levels of the same two or more polypeptides in the comparative sample; and
   determining whether the subject suspected of having a brain damage-related disorder has a brain damage-related disorder based on said comparison, wherein each of the two or more polypeptides is detected in significantly higher amounts in the body fluid of brain damage-related disorder-affected subjects than are detected in the body fluid of non-brain damage-related disorder-affected subjects, whereby the detection of significantly higher amounts of the two or more polypeptides in the body fluid sample is indicative of a brain damage-related disorder.

2. The method according to claim 1, wherein antibodies are used to determine the amount of each of the two or more polypeptides.

3. A method of diagnosis of a brain damage-related disorder in a subject suspected of having a brain damage-related disorder, which comprises:
   detecting levels of two or more polypeptides comprising H-FABP and Glutathione S transferase P in a sample of body fluid taken from the subject suspected of having a brain damage-related disorder, wherein the body fluid is selected from the group consisting of cerebrospinal fluid, plasma, serum, and blood;
   detecting levels of the same two or more polypeptides comprising H-FABP and Glutathione S transferase P in a comparative sample of body fluid taken from a subject known to have a brain damage-related disorder, wherein the body fluid is the same type of body fluid as the sample from the subject suspected of having a brain damage-related disorder;
   comparing the levels of the detected two or more polypeptides in the sample of body fluid taken from the subject suspected of having a brain damage-related disorder with the levels of the same two or more polypeptides in the comparative sample; and
   determining whether the subject suspected of having a brain damage-related disorder has a brain damage-related disorder based on said comparison, wherein the levels of each of the two or more polypeptides detected in the body fluid of the subject suspected of having a brain damage-related disorder-affected are detected in amounts not significantly different from the levels of two or more polypeptides detected in the body fluid of a subject known to have a brain damage-related disorder, whereby the detection of levels of the two or more polypeptides in a body fluid sample that are not significantly different is indicative of a brain damage-related disorder.

4. The method according to claim 3, wherein antibodies are used to determine the amount of each of the two or more polypeptides.

\* \* \* \* \*

SEQUENCE LISTING

<160> NUMBER OF SEQ ID NOS: 16

<210> SEQ ID NO 1
<211> LENGTH: 131
<212> TYPE: PRT
<213> ORGANISM: Homo sapiens

<400> SEQUENCE: 1

Cys Asp Ala Phe Val Gly Thr Trp Lys Leu Val Ser Ser Glu Asn Phe
1               5                   10                  15

Asp Asp Tyr Met Lys Glu Val Gly Val Gly Phe Ala Thr Arg Lys Val
            20                  25                  30

Ala Gly Met Ala Lys Pro Asn Met Ile Ile Ser Val Asn Gly Asp Val
        35                  40                  45

Ile Thr Ile Lys Ser Glu Ser Thr Phe Lys Asn Thr Glu Ile Ser Phe
    50                  55                  60

Ile Leu Gly Gln Glu Phe Asp Glu Val Thr Ala Asp Asp Arg Lys Val
65                  70                  75                  80

Lys Ser Thr Ile Thr Leu Asp Gly Gly Val Leu Val His Val Gln Lys
                85                  90                  95

Trp Asp Gly Lys Ser Thr Thr Ile Lys Arg Lys Arg Glu Asp Asp Lys
            100                 105                 110

Leu Val Val Glu Cys Val Met Lys Gly Val Thr Ser Thr Arg Val Tyr
        115                 120                 125

Glu Arg Ala
    130

<210> SEQ ID NO 2
<211> LENGTH: 135
<212> TYPE: PRT
<213> ORGANISM: Homo sapiens

<400> SEQUENCE: 2

Met Ala Thr Val Gln Gln Leu Glu Gly Arg Trp Arg Leu Val Asp Ser
1               5                   10                  15

Lys Gly Phe Asp Glu Tyr Met Lys Glu Leu Gly Val Gly Ile Ala Leu
            20                  25                  30

Arg Lys Met Gly Ala Met Ala Lys Pro Asp Cys Ile Ile Thr Cys Asp
        35                  40                  45

Gly Lys Asn Leu Thr Ile Lys Thr Glu Ser Thr Leu Lys Thr Thr Gln
    50                  55                  60

Phe Ser Cys Thr Leu Gly Glu Lys Phe Glu Glu Thr Thr Ala Asp Gly
65                  70                  75                  80

Arg Lys Thr Gln Thr Val Cys Asn Phe Thr Asp Gly Ala Leu Val Gln
                85                  90                  95

His Gln Glu Trp Asp Gly Lys Glu Ser Thr Ile Thr Arg Lys Leu Lys
            100                 105                 110

Asp Gly Lys Leu Val Val Glu Cys Val Met Asn Asn Val Thr Cys Thr
        115                 120                 125

Arg Ile Tyr Glu Lys Val Glu
    130                 135

<210> SEQ ID NO 3
<211> LENGTH: 223
<212> TYPE: PRT
<213> ORGANISM: Homo sapiens

```
<400> SEQUENCE: 3

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
                35                  40                  45

Leu Leu Leu Leu Phe Pro Leu Thr Ala Gln His Glu Asn Phe Arg Lys
        50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
                100                 105                 110

Val Leu Lys Gln Phe Leu Ser Glu Thr Glu Lys Met Ser Pro Glu Asp
            115                 120                 125

Arg Ala Lys Cys Phe Glu Lys Asn Glu Ala Ile Gln Ala Ala His Asp
        130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
                180                 185                 190

Leu Leu Lys Asp Ala Ala Lys Val Cys Arg Glu Phe Thr Glu Arg Glu
            195                 200                 205

Gln Gly Glu Val Arg Phe Ser Ala Val Ala Leu Cys Lys Ala Ala
        210                 215                 220

<210> SEQ ID NO 4
<211> LENGTH: 432
<212> TYPE: PRT
<213> ORGANISM: Homo sapiens

<400> SEQUENCE: 4

Met Glu Arg Arg Arg Ile Thr Ser Ala Ala Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
                35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
                100                 105                 110

Ala Asp Val Tyr Gln Ala Glu Leu Arg Glu Leu Arg Leu Arg Leu Asp
            115                 120                 125

Gln Leu Thr Ala Asn Ser Ala Arg Leu Glu Val Glu Arg Asp Asn Leu
        130                 135                 140

Ala Gln Asp Leu Ala Thr Val Arg Gln Lys Leu Gln Asp Glu Thr Asn
```

```
                145                 150                 155                 160
Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
        355                 360                 365

Leu Leu Glu Gly Glu Glu Asn Arg Ile Thr Ile Pro Val Gln Thr Phe
    370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430

<210> SEQ ID NO 5
<211> LENGTH: 168
<212> TYPE: PRT
<213> ORGANISM: Homo sapiens

<400> SEQUENCE: 5

Ala Pro Glu Ala Gln Val Ser Val Gln Pro Asn Phe Gln Gln Asp Lys
1               5                   10                  15

Phe Leu Gly Arg Trp Phe Ser Ala Gly Leu Ala Ser Asn Ser Ser Trp
            20                  25                  30

Leu Arg Glu Lys Lys Ala Ala Leu Ser Met Cys Lys Ser Val Val Ala
        35                  40                  45

Pro Ala Thr Asp Gly Gly Leu Asn Leu Thr Ser Thr Phe Leu Arg Lys
    50                  55                  60

Asn Gln Cys Glu Thr Arg Thr Met Leu Leu Gln Pro Ala Gly Ser Leu
65                  70                  75                  80

Gly Ser Tyr Ser Tyr Arg Ser Pro His Trp Gly Ser Thr Tyr Ser Val
                85                  90                  95

Ser Val Val Glu Thr Asp Tyr Asp Gln Tyr Ala Leu Leu Tyr Ser Gln
```

```
                     100                 105                 110
Gly Ser Lys Gly Pro Gly Glu Asp Phe Arg Met Ala Thr Leu Tyr Ser
        115                 120                 125

Arg Thr Gln Thr Pro Arg Ala Glu Leu Lys Glu Lys Phe Thr Ala Phe
    130                 135                 140

Cys Lys Ala Gln Gly Phe Thr Glu Asp Thr Ile Val Phe Leu Pro Gln
145                 150                 155                 160

Thr Asp Lys Cys Met Thr Glu Gln
                165

<210> SEQ ID NO 6
<211> LENGTH: 238
<212> TYPE: PRT
<213> ORGANISM: Homo sapiens

<400> SEQUENCE: 6

Met Leu Cys Cys Met Arg Arg Thr Lys Gln Val Glu Lys Asn Asp Asp
1               5                   10                  15

Asp Gln Lys Ile Glu Gln Asp Gly Ile Lys Pro Glu Asp Lys Ala His
            20                  25                  30

Lys Ala Ala Thr Lys Ile Gln Ala Ser Phe Arg Gly His Ile Thr Arg
        35                  40                  45

Lys Lys Leu Lys Gly Glu Lys Lys Asp Asp Val Gln Ala Ala Glu Ala
    50                  55                  60

Glu Ala Asn Lys Lys Asp Glu Ala Pro Val Ala Asp Gly Val Glu Lys
65                  70                  75                  80

Lys Gly Glu Gly Thr Thr Thr Ala Glu Ala Ala Pro Ala Thr Gly Ser
                85                  90                  95

Lys Pro Asp Glu Pro Gly Lys Ala Gly Glu Thr Pro Ser Glu Glu Lys
            100                 105                 110

Lys Gly Glu Gly Asp Ala Ala Thr Glu Gln Ala Ala Pro Gln Ala Pro
        115                 120                 125

Ala Ser Ser Glu Glu Lys Ala Gly Ser Ala Glu Thr Glu Ser Ala Thr
    130                 135                 140

Lys Ala Ser Thr Asp Asn Ser Pro Ser Ser Lys Ala Glu Asp Ala Pro
145                 150                 155                 160

Ala Lys Glu Glu Pro Lys Gln Ala Asp Val Pro Ala Ala Val Thr Ala
                165                 170                 175

Ala Ala Ala Thr Thr Pro Ala Ala Glu Asp Ala Ala Lys Ala Thr
            180                 185                 190

Ala Gln Pro Pro Thr Glu Thr Gly Glu Ser Ser Gln Ala Glu Glu Asn
        195                 200                 205

Ile Glu Ala Val Asp Glu Thr Lys Pro Lys Glu Ser Ala Arg Gln Asp
    210                 215                 220

Glu Gly Lys Glu Glu Pro Glu Ala Asp Gln Glu His Ala
225                 230                 235

<210> SEQ ID NO 7
<211> LENGTH: 543
<212> TYPE: PRT
<213> ORGANISM: Homo sapiens

<400> SEQUENCE: 7

Ser Ser Phe Ser Tyr Glu Pro Tyr Tyr Ser Thr Ser Tyr Lys Arg Arg
1               5                   10                  15

Tyr Val Glu Thr Pro Arg Val His Ile Ser Val Arg Ser Gly Tyr Ser
            20                  25                  30
```

```
Thr Ala Arg Ser Ala Tyr Ser Ser Tyr Ser Ala Pro Val Ser Ser Ser
         35                  40                  45

Leu Ser Val Arg Arg Ser Tyr Ser Ser Ser Gly Ser Leu Met Pro
 50                  55                  60

Ser Leu Glu Asn Leu Asp Leu Ser Gln Val Ala Ile Ser Asn Asp
 65                  70                  75                  80

Leu Lys Ser Ile Arg Thr Gln Glu Lys Ala Gln Leu Gln Asp Leu Asn
                 85                  90                  95

Asp Arg Phe Ala Ser Phe Ile Glu Arg Val His Glu Leu Glu Gln Gln
                100                 105                 110

Asn Lys Val Leu Glu Ala Glu Leu Leu Val Leu Arg Gln Lys His Ser
             115                 120                 125

Glu Pro Ser Arg Phe Arg Ala Leu Tyr Glu Gln Glu Ile Arg Asp Leu
             130                 135                 140

Arg Leu Ala Ala Glu Asp Ala Thr Thr Asn Glu Lys Gln Ala Leu Arg
145                 150                 155                 160

Gly Glu Arg Glu Glu Gly Leu Glu Glu Thr Leu Arg Asn Leu Gln Ala
                 165                 170                 175

Arg Tyr Glu Glu Val Leu Ser Arg Glu Asp Ala Glu Gly Arg Leu
             180                 185                 190

Met Glu Arg Arg Lys Gly Ala Asp Glu Ala Ala Leu Ala Arg Ala Glu
             195                 200                 205

Leu Glu Lys Arg Ile Asp Ser Leu Met Asp Glu Ile Ser Phe Leu Lys
             210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                 245                 250                 255

Ala Leu Lys Asp Ile Arg Ala Gln Tyr Glu Lys Leu Ala Ala Lys Asn
             260                 265                 270

Met Gln Asn Ala Glu Glu Trp Phe Lys Ser Arg Phe Thr Val Leu Thr
             275                 280                 285

Glu Ser Ala Ala Lys Asn Thr Asp Ala Val Arg Ala Ala Lys Asp Glu
             290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                 325                 330                 335

Glu Asp Lys Gln Asn Ala Asp Ile Ser Ala Met Gln Asp Thr Ile Asn
             340                 345                 350

Lys Leu Glu Asn Glu Leu Arg Thr Thr Lys Ser Glu Met Ala Arg Tyr
             355                 360                 365

Leu Lys Glu Tyr Gln Asp Leu Leu Asn Val Lys Met Ala Leu Asp Ile
             370                 375                 380

Glu Ile Ala Ala Tyr Arg Lys Leu Leu Glu Gly Glu Glu Thr Arg Leu
385                 390                 395                 400

Ser Phe Thr Ser Val Gly Ser Ile Thr Ser Gly Tyr Ser Gln Ser Ser
                 405                 410                 415

Gln Val Phe Gly Arg Ser Ala Tyr Gly Gly Leu Gln Thr Ser Ser Tyr
             420                 425                 430

Leu Met Ser Thr Arg Ser Phe Pro Ser Tyr Tyr Thr Ser His Val Gln
             435                 440                 445

Glu Glu Gln Thr Glu Val Glu Glu Thr Ile Glu Ala Ser Lys Ala Glu
```

```
                450             455             460
Glu Ala Lys Asp Glu Pro Pro Ser Gly Glu Ala Glu Glu Glu
465                 470                 475                 480

Lys Asp Lys Glu Glu Ala Glu Glu Glu Ala Glu Glu Glu
                485                 490                 495

Ala Ala Lys Glu Glu Ser Glu Ala Lys Glu Glu Glu Gly Gly
            500                 505                 510

Glu Gly Glu Gly Glu Glu Thr Lys Glu Ala Glu Glu Glu Lys
        515                 520                 525

Lys Val Glu Gly Ala Gly Glu Glu Gln Ala Ala Lys Lys Asp
    530                 535                 540

<210> SEQ ID NO 8
<211> LENGTH: 189
<212> TYPE: PRT
<213> ORGANISM: Homo sapiens

<400> SEQUENCE: 8

Met Asp Ala Val Asp Ala Thr Met Glu Lys Leu Arg Ala Gln Cys Leu
1               5                   10                  15

Ser Arg Gly Ala Ser Gly Ile Gln Gly Leu Ala Arg Phe Phe Arg Gln
            20                  25                  30

Leu Asp Arg Asp Gly Ser Arg Ser Leu Asp Ala Asp Glu Phe Arg Gln
        35                  40                  45

Gly Leu Ala Lys Leu Gly Leu Val Leu Asp Gln Ala Glu Ala Glu Gly
    50                  55                  60

Val Cys Arg Lys Trp Asp Arg Asn Gly Ser Gly Thr Leu Asp Leu Glu
65              70                  75                  80

Glu Phe Leu Arg Ala Leu Arg Pro Pro Met Ser Gln Ala Arg Glu Ala
                85                  90                  95

Val Ile Ala Ala Ala Phe Ala Lys Leu Asp Arg Ser Gly Asp Gly Val
            100                 105                 110

Val Thr Val Asp Asp Leu Arg Gly Val Tyr Ser Gly Arg Ala His Pro
        115                 120                 125

Lys Val Arg Ser Gly Glu Trp Thr Glu Asp Glu Val Leu Arg Arg Phe
    130                 135                 140

Leu Asp Asn Phe Asp Ser Ser Glu Lys Asp Gly Gln Val Thr Leu Ala
145                 150                 155                 160

Glu Phe Gln Asp Tyr Tyr Ser Gly Val Ser Ala Ser Met Asn Thr Asp
                165                 170                 175

Glu Glu Phe Val Ala Met Met Thr Ser Ala Trp Gln Leu
            180                 185

<210> SEQ ID NO 9
<211> LENGTH: 189
<212> TYPE: PRT
<213> ORGANISM: Homo sapiens

<400> SEQUENCE: 9

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60
```

```
Gly Pro Tyr Asp Val Val Leu Pro Gly Gly Asn Leu Ala Gln
 65                  70                  75                  80

Asn Leu Ser Glu Ser Ala Ala Val Lys Glu Ile Leu Lys Glu Gln Glu
                 85                  90                  95

Asn Arg Lys Gly Leu Ile Ala Ala Ile Cys Ala Gly Pro Thr Ala Leu
                100                 105                 110

Leu Ala His Glu Ile Gly Phe Gly Ser Lys Val Thr Thr His Pro Leu
                115                 120                 125

Ala Lys Asp Lys Met Met Asn Gly Gly His Tyr Thr Tyr Ser Glu Asn
                130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
                180                 185

<210> SEQ ID NO 10
<211> LENGTH: 343
<212> TYPE: PRT
<213> ORGANISM: Homo sapiens

<400> SEQUENCE: 10

Met Phe Ser Phe Asn Met Phe Asp His Pro Ile Pro Arg Val Phe Gln
  1               5                  10                  15

Asn Arg Phe Ser Thr Gln Tyr Arg Cys Phe Ser Val Ser Met Leu Ala
                 20                  25                  30

Gly Pro Asn Asp Arg Ser Asp Val Glu Lys Gly Gly Lys Ile Ile Met
                 35                  40                  45

Pro Pro Ser Ala Leu Asp Gln Leu Ser Arg Leu Asn Ile Thr Tyr Pro
             50                  55                  60

Met Leu Phe Lys Leu Thr Asn Lys Asn Ser Asp Arg Met Thr His Cys
 65                  70                  75                  80

Gly Val Leu Glu Phe Val Ala Asp Glu Gly Ile Cys Tyr Leu Pro His
                 85                  90                  95

Trp Met Met Gln Asn Leu Leu Leu Glu Glu Asp Gly Leu Val Gln Leu
                100                 105                 110

Glu Thr Val Asn Leu Gln Val Ala Thr Tyr Ser Lys Ser Lys Phe Cys
                115                 120                 125

Tyr Leu Pro His Trp Met Met Gln Asn Leu Leu Leu Glu Glu Gly Gly
                130                 135                 140

Leu Val Gln Val Glu Ser Val Asn Leu Gln Val Ala Thr Tyr Ser Lys
145                 150                 155                 160

Phe Gln Pro Gln Ser Pro Asp Phe Leu Asp Ile Thr Asn Pro Lys Ala
                165                 170                 175

Val Leu Glu Asn Ala Leu Arg Asn Phe Ala Cys Leu Thr Thr Gly Asp
                180                 185                 190

Val Ile Ala Ile Asn Tyr Asn Glu Lys Ile Tyr Glu Leu Arg Val Met
                195                 200                 205

Glu Thr Lys Pro Asp Lys Ala Val Ser Ile Ile Glu Cys Asp Met Asn
                210                 215                 220

Val Asp Phe Asp Ala Pro Leu Gly Tyr Lys Glu Pro Glu Arg Gln Val
225                 230                 235                 240

Gln His Glu Glu Ser Thr Glu Gly Glu Ala Asp His Ser Gly Tyr Ala
                245                 250                 255
```

```
Gly Glu Leu Gly Phe Arg Ala Phe Ser Gly Ser Gly Asn Arg Leu Asp
                260                 265                 270

Gly Lys Lys Lys Gly Val Glu Pro Ser Pro Ser Pro Ile Lys Pro Gly
            275                 280                 285

Asp Ile Lys Arg Gly Ile Pro Asn Tyr Glu Phe Lys Leu Gly Lys Ile
        290                 295                 300

Thr Phe Ile Arg Asn Ser Arg Pro Leu Val Lys Val Glu Glu Asp
305                 310                 315                 320

Glu Ala Gly Gly Arg Phe Val Ala Phe Ser Gly Glu Gly Gln Ser Leu
                325                 330                 335

Arg Lys Lys Gly Arg Lys Pro
            340

<210> SEQ ID NO 11
<211> LENGTH: 152
<212> TYPE: PRT
<213> ORGANISM: Homo sapiens

<400> SEQUENCE: 11

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150

<210> SEQ ID NO 12
<211> LENGTH: 209
<212> TYPE: PRT
<213> ORGANISM: Homo sapiens

<400> SEQUENCE: 12

Pro Pro Tyr Thr Val Val Tyr Phe Pro Val Arg Gly Arg Cys Ala Ala
1               5                   10                  15

Leu Arg Met Leu Leu Ala Asp Gln Gly Gln Ser Trp Lys Glu Glu Val
            20                  25                  30

Val Thr Val Glu Thr Trp Gln Glu Gly Ser Leu Lys Ala Ser Cys Leu
        35                  40                  45

Tyr Gly Gln Leu Pro Lys Phe Gln Asp Gly Asp Leu Thr Leu Tyr Gln
    50                  55                  60

Ser Asn Thr Ile Leu Arg His Leu Gly Arg Thr Leu Gly Leu Tyr Gly
65                  70                  75                  80
```

```
Lys Asp Gln Gln Glu Ala Ala Leu Val Asp Met Val Asn Asp Gly Val
            85                  90                  95

Glu Asp Leu Arg Cys Lys Tyr Ile Ser Leu Ile Tyr Thr Asn Tyr Glu
                100                 105                 110

Ala Gly Lys Asp Asp Tyr Val Lys Ala Leu Pro Gly Gln Leu Lys Pro
            115                 120                 125

Phe Glu Thr Leu Leu Ser Gln Asn Gln Gly Gly Lys Thr Phe Ile Val
        130                 135                 140

Gly Asp Gln Ile Ser Phe Ala Asp Tyr Asn Leu Leu Asp Leu Leu Leu
145                 150                 155                 160

Ile His Glu Val Leu Ala Pro Gly Cys Leu Asp Ala Phe Pro Leu Leu
                165                 170                 175

Ser Ala Tyr Val Gly Arg Leu Ser Ala Arg Pro Lys Leu Lys Ala Phe
            180                 185                 190

Leu Ala Ser Pro Glu Tyr Val Asn Leu Pro Ile Asn Gly Asn Gly Lys
        195                 200                 205

Gln

<210> SEQ ID NO 13
<211> LENGTH: 348
<212> TYPE: PRT
<213> ORGANISM: Homo sapiens

<400> SEQUENCE: 13

Gly Pro Ile Pro Glu Val Leu Lys Asn Tyr Met Asp Ala Gln Tyr Tyr
1               5                   10                  15

Gly Glu Ile Gly Ile Gly Thr Pro Pro Gln Cys Phe Thr Val Val Phe
                20                  25                  30

Asp Thr Gly Ser Ser Asn Leu Trp Val Pro Ser Ile His Cys Lys Leu
            35                  40                  45

Leu Asp Ile Ala Cys Trp Ile His His Lys Tyr Asn Ser Asp Lys Ser
        50                  55                  60

Ser Thr Tyr Val Lys Asn Gly Thr Ser Phe Asp Ile His Tyr Gly Ser
65                  70                  75                  80

Gly Ser Leu Ser Gly Tyr Leu Ser Gln Asp Thr Val Ser Val Pro Cys
                85                  90                  95

Gln Ser Ala Ser Ser Ala Ser Ala Leu Gly Gly Val Lys Val Glu Arg
            100                 105                 110

Gln Val Phe Gly Glu Ala Thr Lys Gln Pro Gly Ile Thr Phe Ile Ala
        115                 120                 125

Ala Lys Phe Asp Gly Ile Leu Gly Met Ala Tyr Pro Arg Ile Ser Val
130                 135                 140

Asn Asn Val Leu Pro Val Phe Asp Asn Leu Met Gln Gln Lys Leu Val
145                 150                 155                 160

Asp Gln Asn Ile Phe Ser Phe Tyr Leu Ser Arg Asp Pro Asp Ala Gln
                165                 170                 175

Pro Gly Gly Glu Leu Met Leu Gly Gly Thr Asp Ser Lys Tyr Tyr Lys
            180                 185                 190

Gly Ser Leu Ser Tyr Leu Asn Val Thr Arg Lys Ala Tyr Trp Gln Val
        195                 200                 205

His Leu Asp Gln Val Glu Val Ala Ser Gly Leu Thr Leu Cys Lys Glu
210                 215                 220

Gly Cys Glu Ala Ile Val Asp Thr Gly Thr Ser Leu Met Val Gly Pro
225                 230                 235                 240

Val Asp Glu Val Arg Glu Leu Gln Lys Ala Ile Gly Ala Val Pro Leu
```

```
                245                 250                 255
Ile Gln Gly Glu Tyr Met Ile Pro Cys Glu Lys Val Ser Thr Leu Pro
            260                 265                 270

Ala Ile Thr Leu Lys Leu Gly Gly Lys Gly Tyr Lys Leu Ser Pro Glu
            275                 280                 285

Asp Tyr Thr Leu Lys Val Ser Gln Ala Gly Lys Thr Leu Cys Leu Ser
            290                 295                 300

Gly Phe Met Gly Met Asp Ile Pro Pro Ser Gly Pro Leu Trp Ile
305                 310                 315                 320

Leu Gly Asp Val Phe Ile Gly Arg Tyr Tyr Thr Val Phe Asp Arg Asp
                325                 330                 335

Asn Asn Arg Val Gly Phe Ala Glu Ala Ala Arg Leu
            340                 345

<210> SEQ ID NO 14
<211> LENGTH: 189
<212> TYPE: PRT
<213> ORGANISM: Homo sapiens

<400> SEQUENCE: 14

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
                20                  25                  30

Val Thr Val Ala Gly Leu Ala Gly Lys Asp Pro Val Gln Cys Ser Arg
            35                  40                  45

Asp Val Val Ile Cys Pro Asp Ala Ser Leu Glu Asp Ala Lys Lys Glu
        50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Cys Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185

<210> SEQ ID NO 15
<211> LENGTH: 214
<212> TYPE: PRT
<213> ORGANISM: Homo sapiens

<400> SEQUENCE: 15

Met Gly Leu Ala Gly Val Cys Ala Leu Arg Arg Ser Ala Gly Tyr Ile
1               5                   10                  15

Leu Val Gly Gly Ala Gly Gly Gln Ser Ala Ala Ala Ala Arg Arg
                20                  25                  30

Cys Ser Glu Gly Glu Trp Ala Ser Gly Gly Val Arg Ser Phe Ser Arg
            35                  40                  45
```

```
Ala Ala Ala Ala Met Ala Pro Ile Lys Val Gly Asp Ala Ile Pro Ala
            50                  55                  60

Val Glu Val Phe Glu Gly Glu Pro Gly Asn Lys Val Asn Leu Ala Glu
 65                  70                  75                  80

Leu Phe Lys Gly Lys Lys Gly Val Leu Phe Gly Val Pro Gly Ala Phe
                 85                  90                  95

Thr Pro Gly Cys Ser Lys Thr His Leu Pro Gly Phe Val Glu Gln Ala
            100                 105                 110

Glu Ala Leu Lys Ala Lys Gly Val Gln Val Val Ala Cys Leu Ser Val
            115                 120                 125

Asn Asp Ala Phe Val Thr Gly Glu Trp Gly Arg Ala His Lys Ala Glu
130                 135                 140

Gly Lys Val Arg Leu Leu Ala Asp Pro Thr Gly Ala Phe Gly Lys Glu
145                 150                 155                 160

Thr Asp Leu Leu Leu Asp Asp Ser Leu Val Ser Ile Phe Gly Asn Arg
                165                 170                 175

Arg Leu Lys Arg Phe Ser Met Val Val Gln Asp Gly Ile Val Lys Ala
            180                 185                 190

Leu Asn Val Glu Pro Asp Gly Thr Gly Leu Thr Cys Ser Leu Ala Pro
            195                 200                 205

Asn Ile Ile Ser Gln Leu
            210

<210> SEQ ID NO 16
<211> LENGTH: 164
<212> TYPE: PRT
<213> ORGANISM: Homo sapiens

<400> SEQUENCE: 16

Val Asn Pro Thr Val Phe Phe Asp Ile Ala Val Asp Gly Glu Pro Leu
 1               5                  10                  15

Gly Arg Val Ser Phe Glu Leu Phe Ala Asp Lys Val Pro Lys Thr Ala
                 20                  25                  30

Glu Asn Phe Arg Ala Leu Ser Thr Gly Glu Lys Gly Phe Gly Tyr Lys
             35                  40                  45

Gly Ser Cys Phe His Arg Ile Ile Pro Gly Phe Met Cys Gln Gly Gly
         50                  55                  60

Asp Phe Thr Arg His Asn Gly Thr Gly Gly Lys Ser Ile Tyr Gly Glu
 65                  70                  75                  80

Lys Phe Glu Asp Glu Asn Phe Ile Leu Lys His Thr Gly Pro Gly Ile
                 85                  90                  95

Leu Ser Met Ala Asn Ala Gly Pro Asn Thr Asn Gly Ser Gln Phe Phe
            100                 105                 110

Ile Cys Thr Ala Lys Thr Glu Trp Leu Asp Gly Lys His Val Val Phe
            115                 120                 125

Gly Lys Val Lys Glu Gly Met Asn Ile Val Glu Ala Met Glu Arg Phe
130                 135                 140

Gly Ser Arg Asn Gly Lys Thr Ser Lys Lys Ile Thr Ile Ala Asp Cys
145                 150                 155                 160

Gly Gln Leu Glu
```